US011174485B2

United States Patent
Martínez Costas et al.

(10) Patent No.: US 11,174,485 B2
(45) Date of Patent: Nov. 16, 2021

(54) PROTEIN MUNS THAT CAN FORM INCLUSIONS IN THE ENDOPLASMIC RETICULUM, METHODS FOR THE USE THEREOF AND USES OF SAME

(71) Applicant: UNIVERSIDADE DE SANTIAGO DE COMPOSTELA, Santiago de Compostela (ES)

(72) Inventors: José Manuel Martínez Costas, Santiago de Compostela (ES); Natalia Barreiro Piñeiro, Santiago de Compostela (ES); Francisco Javier Benavente Martínez, Santiago de Compostela (ES)

(73) Assignee: UNIVERSID ADE DE SANTIAGO DE COMPOSTELA, Santiago de Compostela (ES)

( * ) Notice: Subject to any disclaimer, the term of this patent is extended or adjusted under 35 U.S.C. 154(b) by 443 days.

(21) Appl. No.: 15/513,148

(22) PCT Filed: Sep. 1, 2015

(86) PCT No.: PCT/ES2015/070639
§ 371 (c)(1),
(2) Date: Mar. 21, 2017

(87) PCT Pub. No.: WO2016/046431
PCT Pub. Date: Mar. 31, 2016

(65) Prior Publication Data
US 2017/0298365 A1    Oct. 19, 2017

(30) Foreign Application Priority Data
Sep. 22, 2014   (ES) ............... ES201431378

(51) Int. Cl.
| | | |
|---|---|---|
| *C12N 15/62* | (2006.01) | |
| *C07K 19/00* | (2006.01) | |
| *C07K 14/14* | (2006.01) | |
| *C12N 5/10* | (2006.01) | |
| *C07K 14/005* | (2006.01) | |
| *C12N 7/00* | (2006.01) | |
| *G01N 33/50* | (2006.01) | |
| *A61K 39/00* | (2006.01) | |

(52) U.S. Cl.
CPC .......... *C12N 15/625* (2013.01); *C07K 14/005* (2013.01); *C07K 14/14* (2013.01); *C07K 19/00* (2013.01); *C12N 5/10* (2013.01); *C12N 7/00* (2013.01); *C12N 15/62* (2013.01); *G01N 33/5076* (2013.01); *A61K 39/00* (2013.01); *C07K 2319/04* (2013.01); *C12N 2720/12222* (2013.01); *C12N 2760/20234* (2013.01)

(58) Field of Classification Search
None
See application file for complete search history.

(56) References Cited

U.S. PATENT DOCUMENTS

2012/0301493 A1* 11/2012 Brandariz Nunez .................
C07K 14/005
424/186.1

FOREIGN PATENT DOCUMENTS

| ES | 2364182 A1 | 8/2011 |
| WO | 2011098652 A1 | 8/2011 |
| WO | 2012070008 A2 | 5/2012 |

OTHER PUBLICATIONS

GenBank MuNS protein. Q6W8S7_9REOV. 2006. GenBank. p. 1 (Year: 2006).*
Altschul, Stephen F., et al., "Basic Local Alignment Search Tool", "Journal of Molecular Biology", Oct. 5, 1990, pp. 403-410, vol. 215, No. 3.
Brandariz-Nunez, A., et al., "A Versatile Molecular Tagging Method for Targeting Proteins to Avian Reovirus muNS Inclusions. Use in Protein Immobilization and Purification", "PLoS ONE", Nov. 12, 2010, pp. 1-14, e13961, vol. 5, No. 11.
Hetz, C., et al., "Targeting the unfolded protein response in disease", "Nature Reviews Drug Discovery", Sep. 2013, pp. 703-719, vol. 12.
Matus, S., et al., "Protein folding stress in neurodegenerative diseases: a glimpse into the ER", "Current Opinion in Cell Biology", Jan. 31, 2011, pp. 239-252, vol. 23.
Mori, H., et al., "The Sec protein-translocation pathway", "Trends in Microbiology", Oct. 2001, pp. 494-500, vol. 9, No. 10.
Needleman, S., et al., "A General Method Applicable to the Search for Similarities in the Amino Acid Sequence of Two Proteins", "Journal of Molecular Biology", Mar. 1970, pp. 443-453, vol. 48.
Pearson, W. R., et al., "Improved tools for biological sequence comparison", "Proceedings of the National Academy of Sciences USA", Apr. 1988, pp. 2444-2448, vol. 85.
Smith, T., et al., "Comparison of Biosequences", "Advances in Applied Mathematice", Dec. 1981, pp. 482-489, vol. 2, No. 4.
Touris-Otero, F., et al., "Avian reovirus nonstructural protein ANS forms viroplasm-like inclusions and recruits protein σNS to these structures", "Virology", Feb. 5, 2004, pp. 94-106, vol. 319.
Teng, L., et al., "Database Accession No. A0A0A0QRX6", "Database UniProt", Feb. 4, 2015.

* cited by examiner

*Primary Examiner* — Paul J Holland
(74) *Attorney, Agent, or Firm* — Hultquist, PLLC; Steven J. Hultquist

(57) ABSTRACT

The invention relates to a polynucleotide encoding a polypeptide based on the minimum region of the Orthoreovirus muNS protein that can form inclusions in the endoplasmic reticulum, and to said polypeptide. The invention also relates to a purification method and a method for detecting interaction between two polypeptides based on the capacity of some regions of the Orthoreovirus muNS protein to incorporate themselves into the inclusions, together with a peptide of interest.

13 Claims, 7 Drawing Sheets
(5 of 7 Drawing Sheet(s) Filed in Color)
Specification includes a Sequence Listing.

SEQUENCE LISTING

<160> NUMBER OF SEQ ID NOS: 37

<210> SEQ ID NO 1
<211> LENGTH: 20
<212> TYPE: PRT
<213> ORGANISM: Artificial Sequence
<220> FEATURE:
<223> OTHER INFORMATION: signal peptide

<400> SEQUENCE: 1

Met Gly Trp Ser Leu Ile Leu Leu Phe Leu Val Ala Val Ala Thr Gly
1               5                   10                  15

Val His Ser Gln
            20

<210> SEQ ID NO 2
<211> LENGTH: 29
<212> TYPE: PRT
<213> ORGANISM: Artificial Sequence
<220> FEATURE:
<223> OTHER INFORMATION: signal peptide

<400> SEQUENCE: 2

Met Met Ser Phe Val Ser Leu Leu Leu Val Gly Ile Leu Phe Trp Ala
1               5                   10                  15

Thr Glu Ala Glu Gln Leu Thr Lys Cys Glu Val Phe Gln
            20                  25

<210> SEQ ID NO 3
<211> LENGTH: 25
<212> TYPE: PRT
<213> ORGANISM: Homo sapiens

<400> SEQUENCE: 3

Met Gly Thr Ala Arg Ile Ala Pro Gly Leu Ala Leu Leu Cys Cys
1               5                   10                  15

Pro Val Leu Ser Ser Ala Tyr Ala Leu
            20                  25

<210> SEQ ID NO 4
<211> LENGTH: 25
<212> TYPE: PRT
<213> ORGANISM: Homo sapiens

<400> SEQUENCE: 4

Met Ser Val Leu Thr Pro Leu Leu Leu Arg Gly Leu Thr Gly Ser Ala
1               5                   10                  15

Arg Arg Leu Pro Val Pro Arg Ala Lys
            20                  25

<210> SEQ ID NO 5
<211> LENGTH: 20
<212> TYPE: PRT
<213> ORGANISM: Homo sapiens

<400> SEQUENCE: 5

Met Val Leu Leu Leu Ile Leu Ser Val Leu Leu Leu Lys Glu Asp Val
1               5                   10                  15

Arg Gly Ser Ala
            20

<210> SEQ ID NO 6
<211> LENGTH: 38
<212> TYPE: PRT
<213> ORGANISM: Homo sapiens

<400> SEQUENCE: 6

Met Ala Ser Pro Arg Ser Ser Gly Gln Pro Gly Pro Pro Pro Pro Pro
1               5                   10                  15

Pro Pro Pro Pro Ala Arg Leu Leu Leu Leu Leu Leu Leu Pro Leu Leu
            20                  25                  30

Leu Pro Leu Ala Pro Gly
            35

<210> SEQ ID NO 7
<211> LENGTH: 17

```
<212> TYPE: PRT
<213> ORGANISM: Homo sapiens

<400> SEQUENCE: 7

Met Leu Leu Ser Val Pro Leu Leu Gly Leu Leu Gly Leu Ala Val
1               5                   10                  15

Ala

<210> SEQ ID NO 8
<211> LENGTH: 31
<212> TYPE: PRT
<213> ORGANISM: Homo sapiens

<400> SEQUENCE: 8

Met Gly Trp Ser Cys Ile Ile Leu Phe Leu Val Ala Thr Ala Thr Gly
1               5                   10                  15

Lys Gly Leu Thr Val Ala Gly Leu Arg Ser Gly His Ile Tyr Gly
            20                  25                  30

<210> SEQ ID NO 9
<211> LENGTH: 635
<212> TYPE: PRT
<213> ORGANISM: Avian Orthoreovirus

<400> SEQUENCE: 9

Met Ala Ser Thr Lys Trp Gly Asp Lys Pro Met Ser Leu Ser Met Ser
1               5                   10                  15

His Asp Gly Ser Ser Ile Arg Ser Ala Ala Ser Gln Phe Leu Ser Val
            20                  25                  30

Pro Leu Ser His Ser Thr Pro Ile Pro Pro Gln Arg Lys Thr Val Leu
        35                  40                  45

Leu Lys Phe Met Ile Gly Asp Glu Leu Ile Thr Val Gln Gly Ala Leu
    50                  55                  60

Ala Pro Phe Asp Glu Tyr Trp Tyr Asp Asn Gln Pro Leu Leu Ala Gln
65                  70                  75                  80

Ala Val Glu Met Leu Ala Ser Ala Asp Arg Leu Arg Gln Phe Glu His
                85                  90                  95

Tyr Glu Lys Phe Leu Leu Lys Lys Gly His Gln Ile Thr Glu Ile Met
            100                 105                 110

Asn Arg Leu Arg Leu Phe Phe Thr Asp Val Leu Lys Val Lys Met Glu
        115                 120                 125

Ala Asp Ala Leu Pro Ala Leu Ala Gln Tyr Leu Met Val Gly Thr Leu
    130                 135                 140

Glu Ala Val Ser Thr Ala Asp Ser Pro Asp Ala Cys Ala Pro Val Thr
145                 150                 155                 160

Ser Lys Ile Leu Ala Lys Gln Gln Thr Ile Ala Lys Ser Pro Gly Arg
                165                 170                 175

Leu Asp Glu Glu Glu Tyr Asn Val Ile Arg Ser Arg Phe Leu Thr His
            180                 185                 190

Glu Val Phe Asp Leu Thr Ser Asp Leu Pro Gly Val Gln Pro Phe Met
        195                 200                 205

Asp Met Tyr Tyr Ala Thr Val Pro Arg Ala Asp Ser Thr Gly Trp Cys
    210                 215                 220

Val Tyr Arg Arg Lys Gly Leu Leu Ile Tyr Ala Pro Asp Glu Gln Phe
225                 230                 235                 240

Ser Asp Leu Thr Ile Phe Ser Thr Arg Leu Thr Ala Ser Arg Glu Leu
                245                 250                 255
```

```
Gln Leu Val Ala Gly Asp Val Val Ala Cys Phe Asp Leu Met Asp
            260                 265                 270

Val Ser Asp Ile Ala Pro Ser His Ala Ser Val Gln Glu Glu Arg
        275                 280                 285

Thr Leu Gly Thr Ser Lys Tyr Ser Asn Val Thr Ala Asn Asp His Pro
    290                 295                 300

Leu Val Phe Phe Ser Pro Ser Ala Leu Arg Trp Ala Ile Asp His Ala
305                 310                 315                 320

Cys Thr Asp Ser Leu Val Ser Thr Arg Asn Ile Arg Val Cys Val Gly
                325                 330                 335

Ile Asp Pro Leu Val Thr Arg Trp Thr Arg Asp Gly Val Gln Glu Ala
            340                 345                 350

Ala Ile Leu Met Asp Asp Lys Leu Pro Ser Ala Gly Arg Ala Arg Met
        355                 360                 365

Ala Leu Arg Thr Leu Leu Leu Ala Arg Arg Ser Pro Met Pro Ser Phe
    370                 375                 380

Leu Leu Gly Ala Leu Lys Gln Ser Gly Gly Gln Leu Leu Glu His Tyr
385                 390                 395                 400

Arg Cys Asp Ala Ala Asn Arg Tyr Gly Ser Pro Thr Val Pro Ile Ser
                405                 410                 415

His Pro Pro Pro Cys Ser Lys Cys Pro Glu Leu Lys Glu Gln Ile Ala
            420                 425                 430

Lys Leu Ser Ser Ser Pro Ile Pro Lys Val Asp Ser Ser Val Gly Pro
        435                 440                 445

Ala Ala Leu Leu Ser Lys Ile Ala Asp Leu Gln Arg Ala Asn Arg Glu
    450                 455                 460

Leu Ser Leu Lys Leu Val Asp Val Gln Pro Ala Arg Glu Asp His Leu
465                 470                 475                 480

Leu Ala Tyr Leu Asn Glu His Val Cys Val Asn Ala Lys Asp His Glu
                485                 490                 495

Lys Gly Leu Leu Ala Arg Cys Asn Val Ser Gly Asp Ser Ile Ser Ser
            500                 505                 510

Ile Leu Gly Gln Arg Met Lys Asn Arg Glu Arg Phe Glu Thr Arg Leu
        515                 520                 525

Arg His Glu Ala Ser Ala Glu Trp Glu Pro Arg Val Glu Ala Leu Asn
    530                 535                 540

Gln Glu Leu Ala Lys Ala Arg Val Glu Gln Gln Asp Met Met Thr Gln
545                 550                 555                 560

Ser Leu Gln Tyr Leu Asn Glu Arg Asp Glu Leu Leu Gln Glu Val Asp
                565                 570                 575

Glu Leu Lys Arg Glu Leu Thr Thr Leu Arg Ser Ala Asn Val Arg Leu
            580                 585                 590

Asn Ala Asp Asn His Arg Met Ser Arg Ala Thr Arg Val Gly Asp Ala
        595                 600                 605

Phe Val Ser Asp Val Glu Pro Leu Pro Ser Gly Ile Pro Gly Glu Ser
    610                 615                 620

Lys Pro Ser Met Glu Glu Leu Val Asp Asp Leu
625                 630                 635

<210> SEQ ID NO 10
<211> LENGTH: 721
<212> TYPE: PRT
<213> ORGANISM: Mammalian Orthoreovirus
```

<400> SEQUENCE: 10

```
Met Ala Ser Phe Lys Gly Phe Ser Ala Asn Thr Val Pro Val Ser Lys
1               5                   10                  15

Ala Lys Arg Asp Ile Ser Ser Leu Ala Ala Thr Pro Gly Leu Arg Ser
            20                  25                  30

Gln Ser Phe Thr Pro Ser Val Asp Met Ser Gln Ser Arg Glu Phe Leu
        35                  40                  45

Thr Lys Ala Ile Glu Gln Gly Ser Met Ser Ile Pro Tyr Gln His Val
    50                  55                  60

Asn Val Pro Lys Val Asp Arg Lys Val Val Ser Leu Val Arg Pro
65                  70                  75                  80

Phe Ser Ser Gly Ala Phe Ser Ile Ser Gly Val Ile Ser Pro Ala His
                85                  90                  95

Ala Tyr Leu Leu Glu Cys Leu Pro Gln Leu Glu Gln Ala Met Ala Phe
            100                 105                 110

Val Ala Ser Pro Glu Ser Phe Gln Ala Ser Asp Val Ala Lys Arg Phe
            115                 120                 125

Ala Ile Lys Pro Gly Met Ser Leu Gln Asp Ala Ile Thr Ala Phe Ile
        130                 135                 140

Asn Phe Val Ser Ala Met Leu Lys Met Thr Val Thr Arg Gln Asn Phe
145                 150                 155                 160

Asp Val Ile Val Ala Glu Ile Glu Arg Leu Ala Ser Thr Ser Val Ser
                165                 170                 175

Val Arg Thr Lys Glu Ala Lys Val Ala Asp Glu Glu Leu Met Leu Phe
            180                 185                 190

Gly Leu Asp His Arg Gly Pro Gln Gln Leu Asp Val Ser Asp Ala Lys
        195                 200                 205

Gly Ile Met Lys Ala Ala Asp Ile Gln Thr Thr His Asp Val His Leu
    210                 215                 220

Ala Pro Gly Val Gly Asn Ile Asp Pro Glu Ile Tyr Asn Glu Gly Arg
225                 230                 235                 240

Phe Met Phe Met Gln His Lys Pro Leu Ala Ala Asp Gln Ser Tyr Phe
                245                 250                 255

Thr Leu Glu Thr Ala Asp Tyr Phe Lys Ile Tyr Pro Thr Tyr Asp Glu
            260                 265                 270

His Asp Gly Arg Met Ala Asp Gln Lys Gln Ser Gly Leu Ile Leu Cys
        275                 280                 285

Thr Lys Asp Glu Val Leu Ala Glu Gln Thr Ile Phe Lys Leu Asp Ala
    290                 295                 300

Pro Asp Asp Lys Thr Val His Leu Leu Asp Arg Asp Asp His Val
305                 310                 315                 320

Val Ala Arg Phe Thr Lys Val Phe Ile Glu Asp Val Ala Pro Gly His
                325                 330                 335

His Ala Ala Gln Arg Ser Gly Gln Arg Ser Val Leu Asp Asp Leu Tyr
            340                 345                 350

Ala Asn Thr Gln Val Ile Ser Ile Thr Ser Ala Ala Leu Lys Trp Val
        355                 360                 365

Val Lys His Gly Val Ser Asp Gly Ile Val Asn Arg Lys Asn Val Lys
    370                 375                 380

Val Cys Val Gly Phe Asp Pro Leu Tyr Thr Leu Ser Thr His Asn Gly
385                 390                 395                 400

Val Ser Leu Cys Ala Leu Leu Met Asp Glu Lys Leu Ser Val Leu Asn
                405                 410                 415
```

Ser Ala Cys Arg Met Thr Leu Arg Ser Leu Met Lys Thr Gly Arg Asp
            420                 425                 430

Val Asp Ala His Arg Ala Phe Gln Arg Val Leu Ser Gln Gly Tyr Thr
            435                 440                 445

Ser Leu Met Cys Tyr Tyr His Pro Ser Arg Lys Leu Ala Tyr Gly Glu
    450                 455                 460

Val Leu Phe Leu Glu Arg Ser Asn Asp Val Thr Asp Gly Ile Lys Leu
465                 470                 475                 480

Gln Leu Asp Ala Ser Arg Gln Cys His Glu Cys Pro Val Leu Gln Gln
                485                 490                 495

Lys Val Val Glu Leu Glu Lys Gln Ile Ile Met Gln Lys Ser Ile Gln
                500                 505                 510

Ser Asp Pro Thr Pro Val Ala Leu Gln Pro Leu Leu Ser Gln Leu Arg
            515                 520                 525

Glu Leu Ser Ser Glu Val Thr Arg Leu Gln Met Glu Leu Ser Arg Ala
530                 535                 540

Gln Ser Leu Asn Ala Gln Leu Glu Ala Asp Val Lys Ser Ala Gln Ser
545                 550                 555                 560

Cys Ser Leu Asp Met Tyr Leu Arg His His Thr Cys Ile Asn Gly His
                565                 570                 575

Ala Lys Glu Asp Glu Leu Leu Asp Ala Val Arg Val Ala Pro Asp Val
            580                 585                 590

Arg Arg Glu Ile Met Glu Lys Arg Ser Glu Val Arg Gln Gly Trp Cys
            595                 600                 605

Glu Arg Ile Ser Lys Glu Ala Ala Lys Cys Gln Thr Val Ile Asp
            610                 615                 620

Asp Leu Thr Leu Met Asn Gly Lys Gln Ala Gln Glu Ile Thr Glu Leu
625                 630                 635                 640

Arg Asp Ser Ala Glu Lys Tyr Glu Lys Gln Ile Ala Glu Leu Val Ser
                645                 650                 655

Thr Ile Thr Gln Asn Gln Ile Thr Tyr Gln Gln Glu Leu Gln Ala Leu
            660                 665                 670

Val Ala Lys Asn Val Glu Leu Asp Ala Leu Asn Gln Arg Gln Ala Lys
            675                 680                 685

Ser Leu Arg Ile Thr Pro Ser Leu Leu Ser Ala Thr Pro Ile Asp Ser
    690                 695                 700

Ala Asp Gly Val Ala Asp Leu Ile Asp Phe Ser Val Pro Thr Asp Glu
705                 710                 715                 720

Leu

<210> SEQ ID NO 11
<211> LENGTH: 188
<212> TYPE: PRT
<213> ORGANISM: Avian Orthoreovirus

<400> SEQUENCE: 11

Pro Ala Val Leu Leu Ser Lys Ile Ala Asp Leu Gln Arg Ala Asn Arg
1               5                   10                  15

Glu Leu Ser Leu Lys Leu Val Asp Val Gln Pro Ala Arg Glu Asp His
            20                  25                  30

Leu Leu Ala Tyr Leu Asn Glu His Val Cys Val Asn Ala Lys Asp His
        35                  40                  45

Glu Lys Gly Leu Leu Ala Arg Cys Asn Val Ser Gly Asp Ser Ile Ser
    50                  55                  60

Ser Ile Leu Gly Gln Arg Met Lys Asn Arg Glu Arg Phe Glu Thr Arg
65                  70                  75                  80

Leu Arg His Glu Ala Ser Ala Glu Trp Glu Pro Arg Val Glu Ala Leu
            85                  90                  95

Asn Gln Glu Leu Ala Lys Ala Arg Val Glu Gln Asp Met Met Thr
        100                 105                 110

Gln Ser Leu Gln Tyr Leu Asn Glu Arg Asp Glu Leu Leu Gln Glu Val
            115                 120                 125

Asp Glu Leu Lys Arg Glu Leu Thr Thr Leu Arg Ser Ala Asn Val Arg
        130                 135                 140

Leu Asn Ala Asp Asn His Arg Met Ser Arg Ala Thr Arg Val Gly Asp
145                 150                 155                 160

Ala Phe Val Ser Asp Val Glu Pro Leu Pro Ser Gly Ile Pro Gly Glu
            165                 170                 175

Ser Lys Pro Ser Met Glu Glu Leu Val Asp Asp Leu
            180                 185

<210> SEQ ID NO 12
<211> LENGTH: 251
<212> TYPE: PRT
<213> ORGANISM: Mammalian Orthoreovirus

<400> SEQUENCE: 12

Ser Asn Asp Val Thr Asp Gly Ile Lys Leu Gln Leu Asp Ala Ser Arg
1               5                   10                  15

Gln Cys His Glu Cys Pro Val Leu Gln Gln Lys Val Val Glu Leu Glu
            20                  25                  30

Lys Gln Ile Ile Met Gln Lys Ser Ile Gln Ser Asp Pro Thr Pro Val
        35                  40                  45

Ala Leu Gln Pro Leu Leu Ser Gln Leu Arg Glu Leu Ser Ser Glu Val
    50                  55                  60

Thr Arg Leu Gln Met Glu Leu Ser Arg Ala Gln Ser Leu Asn Ala Gln
65                  70                  75                  80

Leu Glu Ala Asp Val Lys Ser Ala Gln Ser Cys Ser Leu Asp Met Tyr
            85                  90                  95

Leu Arg His His Thr Cys Ile Asn Gly His Ala Lys Glu Asp Glu Leu
        100                 105                 110

Leu Asp Ala Val Arg Val Ala Pro Asp Val Arg Arg Glu Ile Met Glu
    115                 120                 125

Lys Arg Ser Glu Val Arg Gln Gly Trp Cys Arg Ile Ser Lys Glu
130                 135                 140

Ala Ala Ala Lys Cys Gln Thr Val Ile Asp Asp Leu Thr Leu Met Asn
145                 150                 155                 160

Gly Lys Gln Ala Gln Glu Ile Thr Glu Leu Arg Asp Ser Ala Glu Lys
            165                 170                 175

Tyr Glu Lys Gln Ile Ala Glu Leu Val Ser Thr Ile Thr Gln Asn Gln
        180                 185                 190

Ile Thr Tyr Gln Gln Glu Leu Gln Ala Leu Val Ala Lys Asn Val Glu
    195                 200                 205

Leu Asp Ala Leu Asn Gln Arg Gln Ala Lys Ser Leu Arg Ile Thr Pro
210                 215                 220

Ser Leu Leu Ser Ala Thr Pro Ile Asp Ser Val Asp Val Ala Asp
225                 230                 235                 240

Leu Ile Asp Phe Ser Val Pro Thr Asp Glu Leu

<210> SEQ ID NO 13
<211> LENGTH: 188
<212> TYPE: PRT
<213> ORGANISM: Artificial Sequence
<220> FEATURE:
<223> OTHER INFORMATION: variant of the minimum region of the avian
      Orthoreovirus muNS protein having the capacity to form inclusions
      when expressed in a cell

<400> SEQUENCE: 13

Pro Ala Val Leu Leu Ser Lys Ile Ala Asp Leu Gln Arg Ala Asn Arg
1               5                   10                  15

Glu Leu Ser Leu Lys Leu Val Asp Val Gln Pro Ala Arg Glu Asp His
            20                  25                  30

Leu Leu Ala Tyr Leu Asn Glu His Val Cys Val Asn Ala Lys Asp His
        35                  40                  45

Glu Lys Gly Leu Leu Ala Arg Cys Ser Val Ser Gly Asp Ser Ile Ser
    50                  55                  60

Ser Ile Leu Gly Gln Arg Met Lys Asn Arg Glu Arg Phe Glu Thr Arg
65                  70                  75                  80

Leu Arg His Glu Ala Ser Ala Glu Trp Glu Pro Arg Val Glu Ala Leu
                85                  90                  95

Asn Gln Glu Leu Ala Lys Ala Arg Val Glu Gln Asp Met Met Thr
            100                 105                 110

Gln Ser Leu Gln Tyr Leu Asn Glu Arg Asp Glu Leu Leu Gln Glu Val
        115                 120                 125

Asp Glu Leu Lys Arg Glu Leu Thr Thr Leu Arg Ser Ala Asn Val Arg
    130                 135                 140

Leu Asn Ala Asp Asn His Arg Met Ser Arg Ala Thr Arg Val Gly Asp
145                 150                 155                 160

Ala Phe Val Ser Asp Val Glu Pro Leu Pro Ser Gly Ile Pro Gly Glu
                165                 170                 175

Ser Lys Pro Ser Met Glu Glu Leu Val Asp Asp Leu
            180                 185

<210> SEQ ID NO 14
<211> LENGTH: 251
<212> TYPE: PRT
<213> ORGANISM: Artificial Sequence
<220> FEATURE:
<223> OTHER INFORMATION: variant of the minimum region of the mammalian
      Orthoreovirus muNS protein having the capacity to form inclusions
      when expressed in a cell

<400> SEQUENCE: 14

Ser Asn Asp Val Thr Asp Gly Ile Lys Leu Gln Leu Asp Ala Ser Arg
1               5                   10                  15

Gln Cys His Glu Cys Pro Val Leu Gln Gln Lys Val Val Glu Leu Glu
            20                  25                  30

Lys Gln Ile Ile Met Gln Lys Ser Ile Gln Ser Asp Pro Thr Pro Val
        35                  40                  45

Ala Leu Gln Pro Leu Leu Ser Gln Leu Arg Glu Leu Ser Ser Glu Val
    50                  55                  60

Thr Arg Leu Gln Met Glu Leu Ser Arg Ala Gln Ser Leu Asn Ala Gln
65                  70                  75                  80

Leu Glu Ala Asp Val Lys Ser Ala Gln Ser Cys Ser Leu Asp Met Tyr
                85                  90                  95

```
Leu Arg His His Thr Cys Ile Ser Gly His Ala Lys Glu Asp Glu Leu
            100                 105                 110

Leu Asp Ala Val Arg Val Ala Pro Asp Val Arg Arg Glu Ile Met Glu
        115                 120                 125

Lys Arg Ser Glu Val Arg Gln Gly Trp Cys Glu Arg Ile Ser Lys Glu
130                 135                 140

Ala Ala Ala Lys Cys Gln Thr Val Ile Asp Asp Leu Thr Leu Met Asn
145                 150                 155                 160

Gly Lys Gln Ala Gln Glu Ile Thr Glu Leu Arg Asp Ser Ala Glu Lys
                165                 170                 175

Tyr Glu Lys Gln Ile Ala Glu Leu Val Ser Thr Ile Thr Gln Asn Gln
            180                 185                 190

Ile Thr Tyr Gln Gln Glu Leu Gln Ala Leu Val Ala Lys Asn Val Glu
        195                 200                 205

Leu Asp Ala Leu Asn Gln Arg Gln Ala Lys Ser Leu Arg Ile Thr Pro
    210                 215                 220

Ser Leu Leu Ser Ala Thr Pro Ile Asp Ser Val Asp Val Ala Asp
225                 230                 235                 240

Leu Ile Asp Phe Ser Val Pro Thr Asp Glu Leu
                245                 250

<210> SEQ ID NO 15
<211> LENGTH: 251
<212> TYPE: PRT
<213> ORGANISM: Artificial Sequence
<220> FEATURE:
<223> OTHER INFORMATION: variant of the minimum region of the mammalian
      Orthoreovirus muNS protein having the capacity to form inclusions
      when expressed in a cell

<400> SEQUENCE: 15

Ser Asn Asp Val Thr Asp Gly Ile Lys Leu Gln Leu Asp Ala Ser Arg
1               5                   10                  15

Gln Cys His Glu Cys Pro Val Leu Gln Gln Lys Val Val Glu Leu Glu
            20                  25                  30

Lys Gln Ile Ile Met Gln Lys Ser Ile Gln Ser Asp Pro Thr Pro Val
        35                  40                  45

Ala Leu Gln Pro Leu Leu Ser Gln Leu Arg Glu Leu Ser Ser Glu Val
    50                  55                  60

Thr Arg Leu Gln Met Glu Leu Ser Arg Ala Gln Ser Leu Asn Ala Gln
65                  70                  75                  80

Leu Glu Ala Asp Val Lys Ser Ala Gln Ser Cys Ser Leu Asp Met Tyr
                85                  90                  95

Leu Arg His His Thr Cys Ile Asn Gly His Ala Lys Glu Asp Glu Leu
            100                 105                 110

Leu Asp Ala Val Arg Val Ala Pro Asp Val Arg Arg Glu Ile Met Glu
        115                 120                 125

Lys Arg Ser Glu Val Arg Gln Gly Trp Cys Glu Arg Ile Ser Lys Glu
130                 135                 140

Ala Ala Ala Lys Cys Gln Thr Val Ile Asp Asp Leu Thr Leu Met Ser
145                 150                 155                 160

Gly Lys Gln Ala Gln Glu Ile Thr Glu Leu Arg Asp Ser Ala Glu Lys
                165                 170                 175

Tyr Glu Lys Gln Ile Ala Glu Leu Val Ser Thr Ile Thr Gln Asn Gln
            180                 185                 190
```

```
Ile Thr Tyr Gln Gln Glu Leu Gln Ala Leu Val Ala Lys Asn Val Glu
            195                 200                 205

Leu Asp Ala Leu Asn Gln Arg Gln Ala Lys Ser Leu Arg Ile Thr Pro
    210                 215                 220

Ser Leu Leu Ser Ala Thr Pro Ile Asp Ser Val Asp Asp Val Ala Asp
225                 230                 235                 240

Leu Ile Asp Phe Ser Val Pro Thr Asp Glu Leu
                245                 250
```

<210> SEQ ID NO 16
<211> LENGTH: 251
<212> TYPE: PRT
<213> ORGANISM: Artificial Sequence
<220> FEATURE:
<223> OTHER INFORMATION: variant of the minimum region of the mammalian
      Orthoreovirus muNS protein having the capacity to form inclusions
      when expressed in a cell

<400> SEQUENCE: 16

```
Ser Asn Asp Val Thr Asp Gly Ile Lys Leu Gln Leu Asp Ala Ser Arg
1               5                   10                  15

Gln Cys His Glu Cys Pro Val Leu Gln Gln Lys Val Val Glu Leu Glu
            20                  25                  30

Lys Gln Ile Ile Met Gln Lys Ser Ile Gln Ser Asp Pro Thr Pro Val
        35                  40                  45

Ala Leu Gln Pro Leu Leu Ser Gln Leu Arg Glu Leu Ser Ser Glu Val
    50                  55                  60

Thr Arg Leu Gln Met Glu Leu Ser Arg Ala Gln Ser Leu Asn Ala Gln
65                  70                  75                  80

Leu Glu Ala Asp Val Lys Ser Ala Gln Ser Cys Ser Leu Asp Met Tyr
                85                  90                  95

Leu Arg His His Thr Cys Ile Ser Gly His Ala Lys Glu Asp Glu Leu
            100                 105                 110

Leu Asp Ala Val Arg Val Ala Pro Asp Val Arg Arg Glu Ile Met Glu
        115                 120                 125

Lys Arg Ser Glu Val Arg Gln Gly Trp Cys Glu Arg Ile Ser Lys Glu
    130                 135                 140

Ala Ala Ala Lys Cys Gln Thr Val Ile Asp Asp Leu Thr Leu Met Ser
145                 150                 155                 160

Gly Lys Gln Ala Gln Glu Ile Thr Glu Leu Arg Asp Ser Ala Glu Lys
                165                 170                 175

Tyr Glu Lys Gln Ile Ala Glu Leu Val Ser Thr Ile Thr Gln Asn Gln
            180                 185                 190

Ile Thr Tyr Gln Gln Glu Leu Gln Ala Leu Val Ala Lys Asn Val Glu
        195                 200                 205

Leu Asp Ala Leu Asn Gln Arg Gln Ala Lys Ser Leu Arg Ile Thr Pro
    210                 215                 220

Ser Leu Leu Ser Ala Thr Pro Ile Asp Ser Val Asp Asp Val Ala Asp
225                 230                 235                 240

Leu Ile Asp Phe Ser Val Pro Thr Asp Glu Leu
                245                 250
```

<210> SEQ ID NO 17
<211> LENGTH: 5
<212> TYPE: PRT
<213> ORGANISM: Artificial Sequence
<220> FEATURE:
<223> OTHER INFORMATION: enterokinase cleavage site

```
<400> SEQUENCE: 17

Asp Asp Asp Asp Lys
1               5

<210> SEQ ID NO 18
<211> LENGTH: 5
<212> TYPE: PRT
<213> ORGANISM: Artificial Sequence
<220> FEATURE:
<223> OTHER INFORMATION: factor Xa cleavage site

<400> SEQUENCE: 18

Ile Glu Asp Gly Arg
1               5

<210> SEQ ID NO 19
<211> LENGTH: 6
<212> TYPE: PRT
<213> ORGANISM: Artificial Sequence
<220> FEATURE:
<223> OTHER INFORMATION: thrombin cleavage site

<400> SEQUENCE: 19

Leu Val Pro Arg Gly Ser
1               5

<210> SEQ ID NO 20
<211> LENGTH: 7
<212> TYPE: PRT
<213> ORGANISM: Artificial Sequence
<220> FEATURE:
<223> OTHER INFORMATION: TEV proteases cleavage site

<400> SEQUENCE: 20

Glu Asn Leu Tyr Phe Gln Gly
1               5

<210> SEQ ID NO 21
<211> LENGTH: 68
<212> TYPE: PRT
<213> ORGANISM: Avian Orthoreovirus

<400> SEQUENCE: 21

Met Pro Ser Phe Leu Leu Gly Ala Leu Lys Gln Ser Gly Gly Gln Leu
1               5                   10                  15

Leu Glu His Tyr Arg Cys Asp Ala Ala Asn Arg Tyr Gly Ser Pro Thr
            20                  25                  30

Val Pro Ile Ser His Pro Pro Cys Ser Lys Cys Pro Glu Leu Lys
        35                  40                  45

Glu Gln Ile Ala Lys Leu Ser Ser Ser Pro Ile Pro Lys Val Asp Ser
    50                  55                  60

Ser Val Gly Pro
65

<210> SEQ ID NO 22
<211> LENGTH: 30
<212> TYPE: PRT
<213> ORGANISM: Avian Orthoreovirus

<400> SEQUENCE: 22

Pro Ala Ala Leu Leu Ser Lys Ile Ala Asp Leu Gln Arg Ala Asn Arg
1               5                   10                  15
```

```
Glu Leu Ser Leu Lys Leu Val Asp Val Gln Pro Ala Arg Glu
            20                  25                  30

<210> SEQ ID NO 23
<211> LENGTH: 66
<212> TYPE: PRT
<213> ORGANISM: Avian Orthoreovirus

<400> SEQUENCE: 23

Glu Asp His Leu Leu Ala Tyr Leu Asn Glu His Val Cys Val Asn Ala
1               5                   10                  15

Lys Asp His Glu Lys Gly Leu Leu Ala Arg Cys Asn Val Ser Gly Asp
            20                  25                  30

Ser Ile Ser Ser Ile Leu Gly Gln Arg Met Lys Asn Arg Glu Arg Phe
        35                  40                  45

Glu Thr Arg Leu Arg His Glu Ala Ser Ala Glu Trp Glu Pro Arg Val
    50                  55                  60

Glu Ala
65

<210> SEQ ID NO 24
<211> LENGTH: 67
<212> TYPE: PRT
<213> ORGANISM: Avian Orthoreovirus

<400> SEQUENCE: 24

Arg Val Glu Ala Leu Asn Gln Glu Leu Ala Lys Ala Arg Val Glu Gln
1               5                   10                  15

Gln Asp Met Met Thr Gln Ser Leu Gln Tyr Leu Asn Glu Arg Asp Glu
            20                  25                  30

Leu Leu Gln Glu Val Asp Glu Leu Lys Arg Glu Leu Thr Thr Leu Arg
        35                  40                  45

Ser Ala Asn Val Arg Leu Asn Ala Asp Asn His Arg Met Ser Arg Ala
    50                  55                  60

Thr Arg Val
65

<210> SEQ ID NO 25
<211> LENGTH: 66
<212> TYPE: PRT
<213> ORGANISM: Artificial Sequence
<220> FEATURE:
<223> OTHER INFORMATION: variant of the minimum region of the
      Orthoreovirus muNS protein with the capacity to incorporate itself
      into inclusions formed by a protein comprising an Orthoreovirus
      muNS-Mi having the capacity to form inclusions when
<220> FEATURE:
<221> NAME/KEY: SITE
<222> LOCATION: (28)..(28)
<223> OTHER INFORMATION: any amino acid except Asn

<400> SEQUENCE: 25

Glu Asp His Leu Leu Ala Tyr Leu Asn Glu His Val Cys Val Asn Ala
1               5                   10                  15

Lys Asp His Glu Lys Gly Leu Leu Ala Arg Cys Xaa Val Ser Gly Asp
            20                  25                  30

Ser Ile Ser Ser Ile Leu Gly Gln Arg Met Lys Asn Arg Glu Arg Phe
        35                  40                  45

Glu Thr Arg Leu Arg His Glu Ala Ser Ala Glu Trp Glu Pro Arg Val
    50                  55                  60

Glu Ala
```

```
<210> SEQ ID NO 26
<211> LENGTH: 66
<212> TYPE: PRT
<213> ORGANISM: Artificial Sequence
<220> FEATURE:
<223> OTHER INFORMATION: variant of the minimum region of the
      Orthoreovirus muNS protein with the capacity to incorporate itself
      into inclusions formed by a protein comprising an Orthoreovirus
      muNS-Mi having the capacity to form inclusions when

<400> SEQUENCE: 26

Glu Asp His Leu Leu Ala Tyr Leu Asn Glu His Val Cys Val Asn Ala
1               5                   10                  15

Lys Asp His Glu Lys Gly Leu Leu Ala Arg Cys Ser Val Ser Gly Asp
                20                  25                  30

Ser Ile Ser Ser Ile Leu Gly Gln Arg Met Lys Asn Arg Glu Arg Phe
            35                  40                  45

Glu Thr Arg Leu Arg His Glu Ala Ser Ala Glu Trp Glu Pro Arg Val
        50                  55                  60

Glu Ala
65

<210> SEQ ID NO 27
<211> LENGTH: 31
<212> TYPE: DNA
<213> ORGANISM: Artificial Sequence
<220> FEATURE:
<223> OTHER INFORMATION: Forward primer

<400> SEQUENCE: 27
ttggcgcgca aatgccagcc gtactgctgt c                              31

<210> SEQ ID NO 28
<211> LENGTH: 28
<212> TYPE: DNA
<213> ORGANISM: Artificial Sequence
<220> FEATURE:
<223> OTHER INFORMATION: Reverse primer

<400> SEQUENCE: 28
ttgcggccgc aatcacagat catccacc                                  28

<210> SEQ ID NO 29
<211> LENGTH: 43
<212> TYPE: DNA
<213> ORGANISM: Artificial Sequence
<220> FEATURE:
<223> OTHER INFORMATION: oligonucleotide for performing mutagenesis

<400> SEQUENCE: 29
gggcctgctc gctcgttgta gcgtatctgg tgattcaatc tcc                 43

<210> SEQ ID NO 30
<211> LENGTH: 43
<212> TYPE: DNA
<213> ORGANISM: Artificial Sequence
<220> FEATURE:
<223> OTHER INFORMATION: oligonucleotide for performing mutagenesis

<400> SEQUENCE: 30
ggagattgaa tcaccagata cgctacaacg agcgagcagg ccc                 43
```

<210> SEQ ID NO 31
<211> LENGTH: 31
<212> TYPE: DNA
<213> ORGANISM: Artificial Sequence
<220> FEATURE:
<223> OTHER INFORMATION: Forward_VSV primer

<400> SEQUENCE: 31
cggctagcat gaagtgcctt ttgtacttag c                                  31

<210> SEQ ID NO 32
<211> LENGTH: 34
<212> TYPE: DNA
<213> ORGANISM: Artificial Sequence
<220> FEATURE:
<223> OTHER INFORMATION: Reverse_VSV primer

<400> SEQUENCE: 32
cccaagcttg ggagagctct tccaactact gaac                               34

<210> SEQ ID NO 33
<211> LENGTH: 64
<212> TYPE: DNA
<213> ORGANISM: Artificial Sequence
<220> FEATURE:
<223> OTHER INFORMATION: primer for adding an adaptor

<400> SEQUENCE: 33
gccggaattc cgaaggcaaa ccaatcccaa acccactgct gggcctggat ttgcggccgc   60
aaat                                                                64

<210> SEQ ID NO 34
<211> LENGTH: 64
<212> TYPE: DNA
<213> ORGANISM: Artificial Sequence
<220> FEATURE:
<223> OTHER INFORMATION: primer for adding an adaptor

<400> SEQUENCE: 34
atttgcggcc gcaaatccag gcccagcagt gggtttggga ttggtttgcc ttcggaattc   60
cggc                                                                64

<210> SEQ ID NO 35
<211> LENGTH: 8
<212> TYPE: PRT
<213> ORGANISM: Artificial Sequence
<220> FEATURE:
<223> OTHER INFORMATION: PreScission protease cleavage site

<400> SEQUENCE: 35

Leu Glu Val Leu Phe Gln Gly Pro
1               5

<210> SEQ ID NO 36
<211> LENGTH: 34
<212> TYPE: DNA
<213> ORGANISM: Artificial Sequence
<220> FEATURE:
<223> OTHER INFORMATION: Forward IC primer

<400> SEQUENCE: 36
ttgcggccgc aagaagatca cttgttggct tatc                               34

<210> SEQ ID NO 37
<211> LENGTH: 30

-continued

```
<212> TYPE: DNA
<213> ORGANISM: Artificial Sequence
<220> FEATURE:
<223> OTHER INFORMATION: Reverse IC primer

<400> SEQUENCE: 37
gcgtctagat tacgcttcca cacggggttc                                    30
```

PROTEIN MUNS THAT CAN FORM INCLUSIONS IN THE ENDOPLASMIC RETICULUM, METHODS FOR THE USE THEREOF AND USES OF SAME

CROSS-REFERENCE TO RELATED APPLICATIONS

This application is a U.S. national phase under the provisions of 35 U.S.C. § 371 of International Patent Application No. PCT/ES15/70639 filed Sep. 1, 2015, which in turn claims priority of Spanish Patent Application No. P201431378 filed Sep. 22, 2014. The disclosures of such international patent application and Spanish priority patent application are hereby incorporated herein by reference in their respective entireties, for all purposes.

TECHNICAL FIELD OF THE INVENTION

The invention relates to a polynucleotide encoding a polypeptide based on the minimum region of the Orthoreovirus muNS protein that can form inclusions in the endoplasmic reticulum, and to said polypeptide. The invention also relates to a purification method and a method for detecting interaction between two polypeptides based on the capacity of some regions of the Orthoreovirus muNS protein to incorporate themselves into the inclusions, together with a peptide of interest.

STATE OF THE ART

Avian reoviruses are members of the genus Orthoreovirus, one of the 12 genera of the Reoviridae family. These viruses are important pathogens in poultry and cause significant economic losses in the poultry farming industry. Avian reoviruses are viruses without a lipid envelope which replicate in the cytoplasm of infected cells and have a genome consisting of 10 double-stranded RNA segments surrounded by double concentric protein shell 85 nm in diameter. The genomic segments are divided into three classes depending on their electrophoretic mobility, three in class L (large), another three in class M (medium) and four in class S (small). With the exception of the segment S1 which is tricistronic, all the other genes are monocistronic. The genomic segments are transcribed by means of an RNA-dependent polymerase to produce messenger RNAs (mRNAs) with a nucleotide sequence identical to the nucleotide sequence of the positive strand of the double-stranded RNA segment. Viral mRNAs perform two functions in infected cells: they program viral protein synthesis in ribosomes and serve as a template for synthesizing the negative strands of the genomic segments.

The avian reovirus genome encodes at least 12 proteins, 8 of which are structural proteins (that are incorporated into the virion) and 4 non-structural proteins that are expressed in infected cells, but are not part of mature reovirions. Proteins encoded by class L genes are called lambda (λ), those encoded by class M genes are called mu (μ) and those encoded by class S genes are called sigma (σ). An alphabetical suffix (λA, λB, etc.) has been assigned to the structural proteins of each class according to their electrophoretic mobility. The reovirion contains at least 10 different structural proteins, 8 of which (λA, λB, λC, μA, μB, σA, σB and σC) are primary translation products of their mRNAs, whereas the other two, μBN and μBC, stem from the proteolytic processing of the μB precursor. In addition to the structural proteins, avian reoviruses express four non-structural proteins. In this sense, genes M3 and S4 express two major non-structural proteins called μNS and σNS, respectively, whereas p10 and p17 are encoded by the first two cistrons of gene S1.

Avian reoviruses replicate in globular cytoplasmic inclusions called viral factories or viroplasms, which contain structural and non-structural viral proteins but lack cell membranes and organelles. Individual expression of viral proteins in transfected cells revealed that the non-structural muNS protein is the only avian reovirus protein that can form inclusions when expressed in the absence of other viral factors (Touris-Otero et al., 2004; mentioned ad supra). This and the fact that globular cytoplasmic inclusions formed by muNS in transfected cells look very similar to the viral factories of infected cells suggest that muNS is the minimum viral factor required for forming viral factories in cells infected with the avian reovirus. The analysis of transfected cells co-expressing muNS and other viral proteins revealed that muNS plays an important role in early stages of virus morphogenesis and that the recruitment of avian reovirus proteins into viral factories is a temporally controlled, selective process.

Mammalian reoviruses also replicate in globular cytoplasmic inclusions. Like avian reoviruses, the non-structural muNS protein has been found to be involved in the formation of inclusions, as well as in the recruitment of other components into the inclusions for possible participation in genome replication and particle assembly.

Despite the fact that avian reovirus and mammalian muNS proteins show only 28.3% sequence identity, they both contain two regions at their C-terminal end with a high "coiled-coil" structure probability. On the other hand, the mammalian protein is 86 amino acids longer and can make more primary contacts with other structural and non-structural viral proteins than the avian protein can. Although muNS proteins of all mammalian reovirus (MRV) strains produce globular inclusions when expressed in transfected cells, most strains produce viral factories with a filamentous morphology during infection. The filamentous phenotype of mammalian reovirus factories has been attributed to protein mu2, due to its capacity to associate itself both with microtubules and with mammalian reovirus muNS. Expression of truncated versions of MRV muNS in transfected cells revealed that the segment between residues 471-721 is the smallest region of muNS required and sufficient for forming inclusions. It is predicted that this region contains two segments consisting of sequences with a high "coiled-coil" structure-forming probability which are bound by a region preceded by a section of about 50 residues and followed by a C-terminal tail.

There are several systems designed today for determining protein interaction, of which the double-hybrid system is the most popular. This system is based on the expression of two fusion proteins: one in which protein X is fused to the DNA-binding domain of transcription factor GCN4; and another in which protein Y is fused to the transcription activation domain of the same factor GCN4. It is thought that if X and Y interact with one another, they will reconstitute a functional GCN4 in the cell which will activate transcription of a reporter gene. The most obvious problems of this system include: i) even if X and Y do interact with one another, the architecture of said interaction does not often allow reconstructing a functional GCN4; ii) the fusions may change the structures of the different GCN4 domains or of the interaction domains of the test proteins.

A new system using the formation of inclusions by the mammalian reovirus muNS protein as a platform for detecting protein interactions in vivo in mammalian cells has been described, and it has also been adapted for use in yeasts. In this system, the test protein fuses with the muNS C-terminal area so that the fusion generates cytoplasmic inclusions and attracts the ligand of the test protein to said inclusions. In the yeast system, these authors demonstrate that their system is superior to the double-hybrid system in terms of the number and type of interactions detected, at least with the proteins tested in said work. However, this system has several problems, among which the following stand out: i) certain proteins may fold erroneously when being fused with muNS-Mi and lose their capacity to interact with their ligands; ii) some proteins may interfere with the muNS-Mi inclusion-forming capacity and do not form said inclusions at all or generate intracellular aggregates, greatly altering interaction detection; iii) the intracellular location of the test protein or the ligand may not be suitable to enable detection in cytoplasmic inclusions.

Patent document WO 2011/098652 describes a system using the formation of inclusions by the Orthoreovirus muNS protein as a platform for purifying proteins and for detecting protein interactions both in vivo and in vitro. This platform is based on the minimum region of an avian Orthoreovirus muNS protein that can form inclusions, which recruits a peptide tag into said inclusions and into the proteins bound thereto. The peptide tag comprises the minimum region of an Orthoreovirus muNS protein with the capacity of being incorporated into the inclusions formed by the muNS protein.

Nevertheless, none of the approaches available in the state of the art contemplates purifying post-translationally modified proteins in the endoplasmic reticulum since protein-inclusion interactions take place in the cytoplasm. Therefore, there is a need in the state of the art to develop a system having advantages with respect to existing systems, in which for example the protein fused to the inclusions does not alter the formation of said inclusions, the fused protein maintains its activity and several epitopes can be included in said inclusions.

DESCRIPTION OF THE INVENTION

In one aspect, the invention relates to a polynucleotide encoding a polypeptide, hereinafter first polynucleotide of the invention, comprising
(a) a first component comprising a secretory pathway signal peptide, and
(b) a second component comprising the minimum region of an Orthoreovirus muNS protein having the capacity to form inclusions when expressed in a cell or a functionally equivalent variant thereof,
wherein the first component is located in the N-terminal position with respect to the second component.

In another aspect, the invention relates to a polypeptide encoded by the polynucleotide of the invention and to a cell comprising said first polynucleotide of the invention or said polypeptide.

In another aspect, the invention relates to a polynucleotide encoding a fusion protein, hereinafter second polynucleotide of the invention, comprising:
(a) a first component comprising a secretory pathway signal peptide,
(b) a second component comprising a polypeptide of interest, and
(c) a third component comprising the minimum region of an Orthoreovirus muNS protein having the capacity to incorporate itself into inclusions formed by a protein comprising the minimum region of an Orthoreovirus muNS having the capacity to form inclusions when expressed in a cell or a functionally equivalent variant thereof,
wherein the first component is located in the N-terminal position with respect to the second and third components.

In another aspect, the invention relates to a fusion protein encoded by the second polynucleotide of the invention and to a cell comprising said second polynucleotide of the invention or said fusion protein.

In another aspect, the invention relates to a kit, hereinafter kit of the invention, comprising:
(a) component A selected from the group consisting of:
the first polynucleotide of the invention, and
a cell expressing the first polynucleotide of the invention; and
(b) component B comprising the second polynucleotide of the invention.

In another aspect, the invention relates to a purification method for purifying a polypeptide comprising the minimum region of an Orthoreovirus muNS protein having the capacity to form inclusions when expressed in a cell, hereinafter inclusion purification method of the invention, wherein said method comprises
(i) expressing in a cell a polynucleotide encoding a polypeptide comprising
(a) a first component comprising a secretory pathway signal peptide, and
(b) a second component comprising the minimum region of an Orthoreovirus muNS protein having the capacity to form inclusions when expressed in a cell or a functionally equivalent variant thereof,
wherein the first component is located in the N-terminal position with respect to the second component, and wherein the polypeptide further comprises a polypeptide of interest located in the C-terminal position with respect to the first component,
under conditions suitable for the translocation of the polypeptide to the secretory pathway and the formation of inclusions from said minimum region, and
(ii) purifying the inclusions formed in step (i).

In another aspect, the invention relates to a purification method for purifying a fusion protein comprising a polypeptide of interest and the minimum region of an Orthoreovirus muNS protein having the capacity to incorporate itself into the inclusions formed by a protein comprising the minimum region of an Orthoreovirus muNS having the capacity to form inclusions when expressed in a cell, hereinafter first fusion protein purification method of the invention, wherein said method comprises
(i) expressing in a cell a first polynucleotide, wherein said first polynucleotide encodes a polypeptide comprising
(a) a first component comprising a secretory pathway signal peptide, and
(b) a second component comprising the minimum region of an Orthoreovirus muNS protein having the capacity to form inclusions when expressed in a cell or a functionally equivalent variant thereof,
wherein the first component is located in the N-terminal position with respect to the second component,
under conditions suitable for the translocation of the polypeptide to the secretory pathway and the formation of inclusions from said minimum region,
(ii) expressing in said cell a second polynucleotide, wherein said second polynucleotide is a polynucleotide encoding a fusion protein comprising:
(a) a first component comprising a secretory pathway signal peptide, (b) a second component comprising a polypeptide of interest, and
(c) a third component comprising the minimum region of an Orthoreovirus muNS protein having the capacity to incorporate itself into inclusions formed by a protein comprising the minimum region of an Orthoreovirus muNS having the capacity to form inclusions when expressed in a cell or a functionally equivalent variant thereof
wherein the first component is located in the N-terminal position with respect to the second and third components, under conditions suitable for the translocation of the fusion protein to the secretory pathway and for the recruitment of the fusion protein into the inclusions formed in step (i), and
(iii) purifying the complexes comprising the inclusions formed in step (i) and the fusion proteins produced in step (ii),
wherein steps (i) and (ii) can be carried out in any order.

In another aspect, the invention relates to a method for purifying a fusion protein comprising
(a) a polypeptide of interest, and
(b) the minimum region of an Orthoreovirus muNS protein having the capacity to incorporate itself into inclusions formed by a protein comprising the minimum region of an Orthoreovirus muNS having the capacity to form inclusions when expressed in a cell,
from a composition containing said fusion protein, hereinafter second fusion protein purification method of the invention, wherein said method comprises:
(i) contacting said composition with inclusions formed by a polypeptide comprising the minimum region of an Orthoreovirus muNS protein having the capacity to form inclusions when expressed in a cell and lacking N-glycosylation consensus sequences under conditions suitable for the recruitment of the fusion protein into said inclusions;
(ii) purifying the complex formed between the inclusions and the fusion protein of step (i).

In another aspect, the invention relates to a method for purifying a fusion protein comprising
(a) a polypeptide of interest, and
(b) the minimum region of an Orthoreovirus muNS protein having the capacity to incorporate itself into inclusions formed by a protein comprising the minimum region of an Orthoreovirus muNS having the capacity to form inclusions when expressed in a cell, from a composition containing said fusion protein, hereinafter third fusion protein purification method of the invention, wherein said method comprises:
(i) contacting said composition with a polypeptide comprising the minimum region of an Orthoreovirus muNS protein having the capacity to form inclusions when expressed in a cell and lacking N-glycosylation consensus sequences with said composition; wherein said polypeptide with inclusion-forming capacity is in a soluble form, and wherein said contacting is performed in the presence of a divalent cation concentration suitable for forming inclusions from the polypeptide with inclusion-forming capacity and from the recruitment of the fusion protein into said inclusions,
(ii) purifying the complex formed between the inclusions and the fusion protein of step (i).

In another aspect, the invention relates to a method for detecting interaction between a first polypeptide and a second polypeptide, hereinafter first method for detecting interactions of the invention, comprising:
(i) expressing in a cell a polynucleotide encoding a polypeptide comprising
(a) a first component comprising a secretory pathway signal peptide, and
(b) a second component comprising the minimum region of an Orthoreovirus muNS protein having the capacity to form inclusions when expressed in a cell or a functionally equivalent variant thereof,
wherein the first component is located in the N-terminal position with respect to the second component, and wherein the polypeptide further comprises a polypeptide of interest located in the C-terminal position with respect to the first component, and
wherein the polypeptide of interest is the first polypeptide, and
keeping said cell under conditions suitable for forming inclusions;
(ii) expressing in said cell a polynucleotide encoding a fusion protein comprising a secretory pathway signal peptide and the second polypeptide, wherein the signal peptide is located in the N-terminal position with respect to the second polypeptide, and keeping said cell under conditions suitable for said second polypeptide to be expressed; and
(iii) determining if the second polypeptide is associated with the complex formed by the inclusions generated in step (i), wherein if the second polypeptide is detected it is indicative of the interaction between the first and second polypeptides, wherein steps (i) and (ii) are carried out in any order.

In another aspect, the invention relates to a method for detecting interaction between a first polypeptide and a second polypeptide, hereinafter second method for detecting interactions of the invention, comprising:
(i) expressing in a cell a first polynucleotide, wherein said first polynucleotide encodes a polypeptide comprising
(a) a first component comprising a secretory pathway signal peptide, and
(b) a second component comprising the minimum region of an Orthoreovirus muNS protein having the capacity to form inclusions when expressed in a cell or a functionally equivalent variant thereof,
wherein the first component is located in the N-terminal position with respect to the second component, and
keeping said cell under conditions suitable for forming inclusions;
(ii) expressing in said cell a second polynucleotide encoding a fusion protein comprising:
(a) a first component comprising a secretory pathway signal peptide,
(b) a second component comprising said first polypeptide, and
(c) a third component comprising the minimum region of an Orthoreovirus muNS protein having the capacity to incorporate itself into inclusions formed by a protein comprising the minimum region of an Orthoreovirus muNS having the capacity to form inclusions when expressed in a cell,
wherein the first component is located in the N-terminal position with respect to the second and third components, under conditions suitable for the fusion protein to be directed to the inclusions formed in step (i);
(iii) expressing in said cell a third polynucleotide encoding a fusion protein comprising a secretory pathway signal peptide and the second polypeptide, wherein the signal peptide is located in the N-terminal position with respect to the second polypeptide, and keeping said cell under conditions suitable for said second polypeptide to be expressed; and
(iv) determining if the second polypeptide is associated with the complex formed by the inclusions generated in step (i) and the fusion protein expressed in step (ii), wherein if the second polypeptide is detected it is indicative of the interaction between said first and second polypeptides, wherein steps (i), (ii) and (iii) are carried out in any order.

In another aspect, the invention relates to a method for detecting interaction between a first polypeptide and a second polypeptide, hereinafter third method for detecting interactions of the invention, wherein said method comprises
(i) contacting, with the second polypeptide, the inclusions formed by a fusion protein comprising the minimum region of an Orthoreovirus muNS protein having the capacity to form inclusions when expressed in a cell and lacking N-glycosylation consensus sequences and the first polypeptide; and
(ii) detecting the association of the second polypeptide with the inclusions,
wherein detection of the second polypeptide in the inclusions is indicative of the interaction between the first polypeptide and the second polypeptide.

In another aspect, the invention relates to a method for detecting interaction between a first polypeptide and a second polypeptide, hereinafter "fourth method for detecting interactions of the invention," comprising
(i) contacting
(a) inclusions formed by a fusion protein comprising the minimum region of an Orthoreovirus muNS protein having the capacity to form inclusions when expressed in a cell and lacking N-glycosylation consensus sequences,
(b) a fusion protein comprising the minimum region of an Orthoreovirus muNS protein having the capacity to incorporate itself into inclusions formed by a protein comprising the minimum region of an Orthoreovirus muNS having the capacity to form inclusions when expressed in a cell and the first polypeptide, and
(c) the second polypeptide, and
(ii) detecting the association of the second polypeptide with the inclusions,
wherein detection of the second polypeptide in the inclusions is indicative of the interaction between the first polypeptide and the second polypeptide.

In another aspect, the invention relates to the use, hereinafter in vitro use of the invention, of a polynucleotide encoding a fusion protein comprising:
(a) a first component comprising a secretory pathway signal peptide,
(b) a second component comprising said first polypeptide, and
(c) a third component comprising the minimum region of an Orthoreovirus muNS protein having the capacity to incorporate itself into inclusions formed by a protein comprising the minimum region of an Orthoreovirus muNS having the capacity to form inclusions when expressed in a cell,
wherein the first component is located in the N-terminal position with respect to the second and third components,
for incorporating the second component of the polypeptide encoded by said polynucleotide into the inclusions resulting from expression of the polynucleotide in a cell encoding a polypeptide comprising
(a) a first component comprising a secretory pathway signal peptide, and
(b) a second component comprising the minimum region of an Orthoreovirus muNS protein having the capacity to form inclusions when expressed in a cell or a functionally equivalent variant thereof,
wherein the first component is located in the N-terminal position with respect to the second component.

In another aspect, the invention relates to a polynucleotide encoding a polypeptide comprising
(a) a first component comprising a secretory pathway signal peptide, and
(b) a second component comprising the minimum region of an Orthoreovirus muNS protein having the capacity to form inclusions when expressed in a cell or a functionally equivalent variant thereof, and
(c) a third component comprising a polypeptide of interest, wherein the first component is located in the N-terminal position with respect to the second and third components, for use thereof in medicine, hereinafter first therapeutic use of the invention.

In another aspect, the invention relates to a polynucleotide encoding a fusion protein comprising:
(a) a first component comprising a secretory pathway signal peptide,
(b) a second component comprising a polypeptide of interest, and
(c) a third component comprising the minimum region of an Orthoreovirus muNS protein having the capacity to incorporate itself into inclusions formed by a protein comprising the minimum region of an Orthoreovirus muNS having the capacity to form inclusions when expressed in a cell,
wherein the first component is located in the N-terminal position with respect to the second and third components, for use thereof in medicine, hereinafter second therapeutic use of the invention.

In another aspect, the invention relates to the use of a polynucleotide encoding a polypeptide comprising
(a) a first component comprising a secretory pathway signal peptide, and
(b) a second component comprising the minimum region of an Orthoreovirus muNS protein having the capacity to form inclusions when expressed in a cell or a functionally equivalent variant thereof, and
(c) a third component comprising a polypeptide of interest, wherein the first component is located in the N-terminal position with respect to the second component and third component,
for preparing a medicinal product for the treatment of a disease in which expression of the polypeptide of interest is required, hereinafter third therapeutic use of the invention.

In another aspect, the invention relates to the use of a polynucleotide encoding a fusion protein comprising:
(a) a first component comprising a secretory pathway signal peptide,
(b) a second component comprising a polypeptide of interest, and
(c) a third component comprising the minimum region of an Orthoreovirus muNS protein having the capacity to incorporate itself into inclusions formed by a protein comprising the minimum region of an Orthoreovirus muNS having the capacity to form inclusions when expressed in a cell,
wherein the first component is located in the N-terminal position with respect to the second and third components, for preparing a medicinal product for the treatment of a disease in which the expression of the polypeptide of interest is required, hereinafter fourth therapeutic use of the invention.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The modalities shown in detail in the drawings are illustrated by way of non-limiting example:

FIG. 6 shows the immunofluorescence analysis of the expression of the Sec-muNS-Mi and Sec-muNS-Mi* proteins and their capacity for forming inclusions in the ER.

FIGS. 7A and 7B show the capture of VSV-IC* in microspheres in the ER. FIG. 7A shows a diagram of the domain composition of VSV glycoprotein G and the VSV-IC* construct. FIG. 7B shows the immunofluorescence of DF-1 cells co-transfected with the plasmids directing expression of the sec-muNS-Mi* and VSV-IC* proteins.

DETAILED DESCRIPTION OF THE INVENTION

Figure 1:
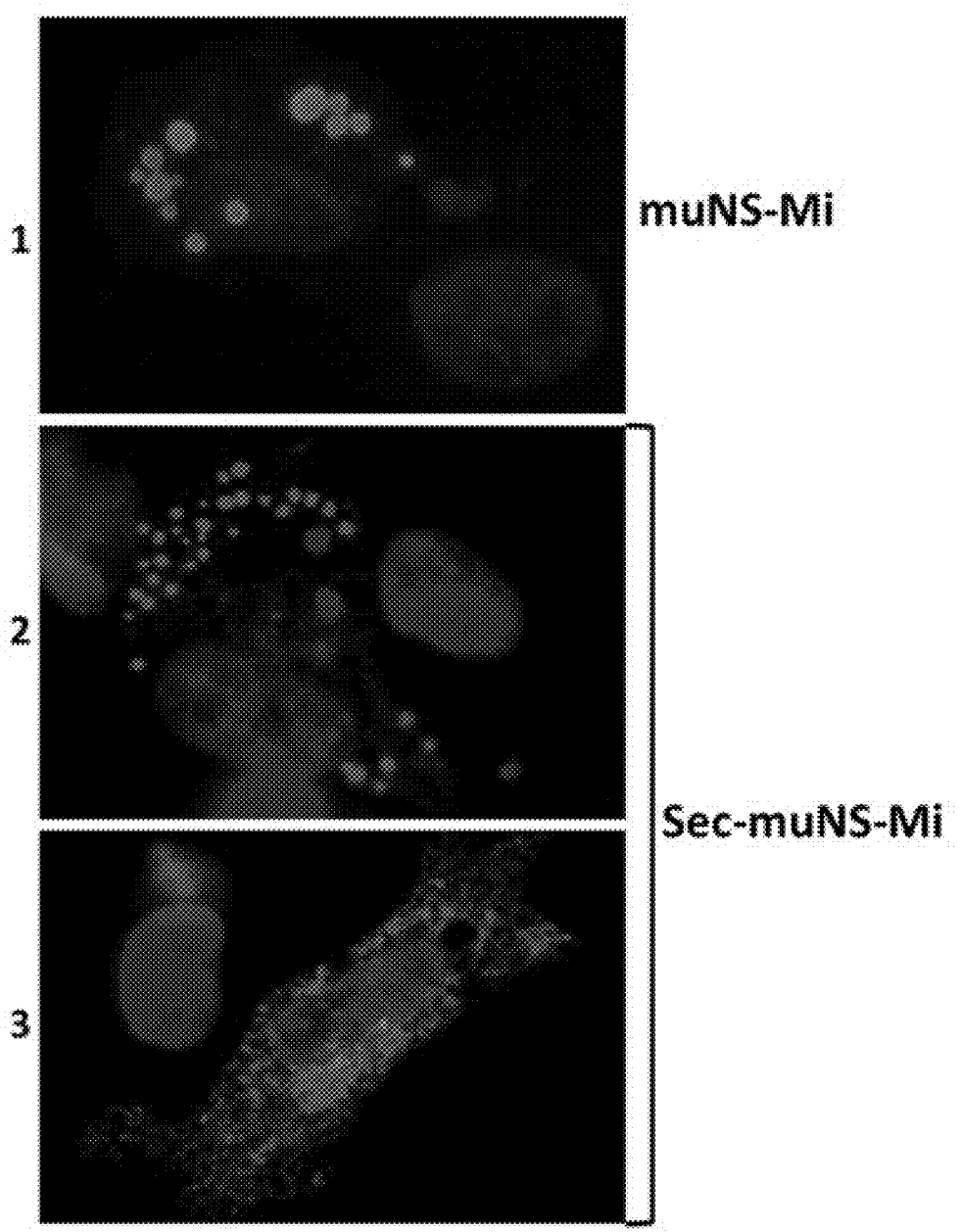
FIG. 1 shows the immunofluorescence detection of the expression of the muNS-Mi and Sec-muNS-Mi proteins.

The authors of the present invention have developed a platform based on directing the minimum region of an Orthoreovirus muNS protein with inclusion-forming capacity to the secretory pathway, which allows purifying post-translationally modified proteins that are fused to or incorporated into said inclusions. This platform further has the following advantages with respect to existing systems: the protein fused or directed to the inclusions does not alter the formation of said inclusions, the fused or directed protein maintains its activity and several epitopes can be included in said inclusions.

Minimum Region of the muNS Protein that can Form Inclusions in the Endoplasmic Reticulum (ER)

The authors of the present invention have clearly shown that the minimum region of the avian Orthoreovirus muNS protein with the capacity of the complete protein to form inclusions, corresponding to residues 448 to 635, conserves said capacity when said region is directed to the secretory pathway. This is demonstrated in Example 1, in which the capacity of this region to form inclusions in the endoplasmic reticulum (ER) is shown.

Therefore, in a first aspect the invention relates to a polynucleotide, hereinafter "first polynucleotide of the invention," encoding a polypeptide comprising
(a) a first component comprising a secretory pathway signal peptide, and
(b) a second component comprising the minimum region of an Orthoreovirus muNS protein having the capacity to form inclusions when expressed in a cell or a functionally equivalent variant thereof,
wherein the first component is located in the N-terminal position with respect to the second component.

As it is used herein, the term "polynucleotide" refers to a polymer formed by a variable number of monomers wherein the monomers are nucleotides, including both ribonucleotides and deoxyribonucleotides. The polynucleotides include monomers modified by means of methylation or non-modified forms as well. The terms "polynucleotide" and "nucleic acid" are used interchangeably herein and include mRNA, cDNA and recombinant polynucleotides.

The term "polypeptide," used interchangeably herein with protein, refers to a chain of amino acids of any length wherein the different amino acids are bound to one another by means of peptide bonds or disulfide bridges.

According to the present invention, the first polynucleotide of the invention comprises a first component comprising a secretory pathway signal peptide.

The term "secretory pathway signal peptide," used interchangeably herein with "signal sequence" or "signal peptide" or "localization signal peptide," refers to a short peptide (5-30 amino acids long) present at the N-terminal end directing the transport of secretory pathway proteins, whether they are proteins residing in certain organelles (ER, Golgi complex or endosomes), proteins secreted by the cell or proteins inserted in the cell membrane. The signal peptide directs the translocation of the protein to which it is bound to the ER. The signal peptide is cleaved by a signal peptidase during or after translocation, generating a free signal peptide and a mature protein.

Non-limiting examples of secretory pathway signal peptides include the signal peptides in major histocompatibility complex class I and II molecules, cytokine or immunoglobulin signal sequences, invariant chain or Lamp1, Tapasin, Erp57, Calreticulin, Calnexin protein signal sequences. In a particular embodiment, the secretory pathway directing sequence is selected from the group consisting of:

the sequence MGWSLILLFLVAVATGVHSQ (SEQ ID NO: 1);

the sequence MMSFVSLLLVGILFWATEAEQLTKCEVFQ (SEQ ID NO: 2);

human PTH1R signal peptide (MGTARIAPGLALLLCCPVLSSAYAL, SEQ ID NO: 3);

human cytochrome c oxidase VIII mitochondrial localization sequence (MSVLTPLLLRGLTGSARRLPVPRAK, SEQ ID NO: 4);

human mGluR5 signal peptide (MVLLLILSVLLLKEDVRGSA, SEQ ID NO: 5);

human GABAB2R signal peptide (MASPRSSGQPGPPPPPPPPPARLLLLLLLPLLLPLAPG, SEQ ID NO: 6);

human calreticulin signal peptide (MLLSVPLLLGLLGLAVA, SEQ ID NO: 7); and human Igγ2b heavy chain signal peptide, (MGWSCIILFLVATATGKGLTVAGLRSGHIYG, SEQ ID NO: 8).

In a preferred embodiment, the secretory pathway signal peptide comprises the sequence MGWSLILLFLVAVATGVHSQ (SEQ ID NO: 1).

The first polynucleotide of the invention comprises a first component which is located in the N-terminal position with respect to the second component.

According to the present invention, the first polynucleotide of the invention comprises a second component comprising the minimum region of an Orthoreovirus muNS protein having the capacity to form inclusions when expressed in a cell or a functionally equivalent variant thereof.

As it is used herein, the term "Orthoreovirus muNS protein" or "Orthoreovirus NS protein" refers to one of the non-structural proteins encoded by the M3 gene of the reovirus or Orthoreovirus, and it is the only Orthoreovirus protein that can form inclusions when expressed in the absence of other viral factors.

muNS proteins of different species are suitable for the purposes of the present invention. Therefore, in a particular embodiment, an Orthoreovirus muNS protein is selected from the group consisting of the avian Orthoreovirus muNS protein and the mammalian Orthoreovirus muNS protein.

In a preferred embodiment, the Orthoreovirus muNS protein is the avian Orthoreovirus muNS protein. It is a protein with 635 amino acids defined by accession number AY608700 (SEQ ID NO: 9) in the GenBank database as of 29 Aug. 2014. As it is used herein, the term "avian Orthoreovirus" or "avian reovirus" refers to one of the 12 genera of the Reoviridae virus family, and specifically to the group within the species which infects poultry. They have dsRNA genomes and are therefore group III viruses.

In another preferred embodiment, the Orthoreovirus muNS protein is the mammalian Orthoreovirus muNS protein. It is a protein with 721 amino acids defined by accession number ABP48918 (SEQ ID NO: 10) in the GenBank database as of 29 Aug. 2014. As it is used herein, the term "mammalian Orthoreovirus" or "mammalian reovirus" refers to one of the 12 genera of the Reoviridae virus family, and specifically to the group within the species which infects mammals. They have dsRNA genomes and are therefore group III viruses.

As it is used herein, the term "minimum region of an Orthoreovirus muNS protein having the capacity to form inclusions when expressed in a cell," or "muNS-Mi," refers to the minimum region of an Orthoreovirus muNS protein which conserves the capacity of the complete protein to form inclusions.

In the preferred embodiment in which the Orthoreovirus muNS protein is the avian Orthoreovirus muNS protein, the minimum region of said muNS protein having the capacity to form inclusions when expressed in a cell comprises the region corresponding to residues 448 to 635 (SEQ ID NO: 11). In an even more preferred embodiment, the minimum region of the avian Orthoreovirus muNS protein comprises the region corresponding to residues 448 to 635 (SEQ ID NO: 11) and up to 635 consecutive amino acids of the avian Orthoreovirus muNS protein, or up to 634 consecutive amino acids of the avian Orthoreovirus muNS protein, or up to 600 consecutive amino acids of the avian Orthoreovirus muNS protein, or up to 550 consecutive amino acids of the avian Orthoreovirus muNS protein, or up to 500 consecutive amino acids of the avian Orthoreovirus muNS protein, or up to 450 consecutive amino acids of the avian Orthoreovirus muNS protein, or up to 400 consecutive amino acids of the avian Orthoreovirus muNS protein, or up to 350 consecutive amino acids of the avian Orthoreovirus muNS protein, or up to 300 consecutive amino acids of the avian Orthoreovirus muNS protein, or up to 250 consecutive amino acids of the avian Orthoreovirus muNS protein, or up to 200 consecutive amino acids of the avian Orthoreovirus muNS protein, or up to 195 consecutive amino acids of the avian Orthoreovirus muNS protein, or up to 190 consecutive amino acids of the avian Orthoreovirus muNS protein, or 188 consecutive amino acids of the avian Orthoreovirus muNS protein.

In the preferred embodiment in which the Orthoreovirus muNS protein is the mammalian Orthoreovirus muNS protein, the minimum region of said muNS protein having the capacity to form inclusions when expressed in a cell comprises the region corresponding to residues 471 to 721 (SEQ ID NO: 12). In an even more preferred embodiment, the minimum region of the mammalian Orthoreovirus muNS protein comprises the region corresponding to residues 471 to 721 (SEQ ID NO: 12) and up to 721 consecutive amino acids of the mammalian Orthoreovirus muNS protein, or up to 720 consecutive amino acids of the mammalian Orthoreovirus muNS protein, or up to 700 consecutive amino acids of the mammalian Orthoreovirus muNS protein, or up to 650 consecutive amino acids of the mammalian Orthoreovirus muNS protein, or up to 600 consecutive amino acids of the mammalian Orthoreovirus muNS protein, or up to 550 consecutive amino acids of the mammalian Orthoreovirus muNS protein, or up to 500 consecutive amino acids of the mammalian Orthoreovirus muNS protein, or up to 450 consecutive amino acids of the mammalian Orthoreovirus muNS protein, or up to 400 consecutive amino acids of the mammalian Orthoreovirus muNS protein, or up to 350 consecutive amino acids of the mammalian Orthoreovirus muNS protein, or up to 300 consecutive amino acids of the mammalian Orthoreovirus muNS protein, or up to 275 consecutive amino acids of the mammalian Orthoreovirus muNS protein, or up to 270 consecutive amino acids of the mammalian Orthoreovirus muNS protein, or up to 265 consecutive amino acids of the mammalian Orthoreovirus muNS protein, or up to 260 consecutive amino acids of the mammalian Orthoreovirus muNS protein, or up to 255 consecutive amino acids of the mammalian Orthoreovirus muNS protein, or 251 consecutive amino acids of the mammalian Orthoreovirus muNS protein.

As it is used herein, the term "inclusion" refers to nuclear or cytoplasmic aggregates, normally protein aggregates. Specifically, the protein forming the inclusions in the genus Orthoreovirus is the muNS or µNS protein, which is one of the non-structural proteins encoded by the M3 gene and the only avian reovirus protein that can form inclusions when expressed in the absence of other viral factors.

"Functionally equivalent variant" of the minimum region of an Orthoreovirus muNS protein having the capacity to form inclusions when expressed in a cell is understood as all those polypeptides derived from said minimum region of muNS by means of modification, insertion and/or deletion of one or more amino acids, provided that the function of the aforementioned muNS proteins is substantially maintained. Specifically, the functionally equivalent variant shows at least one function related to the capacity to generate inclusions in a cell.

Variants suitable for use in the present invention include those showing at least 25%, at least 40%, at least 60%, at least 70%, at least 80%, at least 90%, at least 95%, at least 96%, at least 97%, at least 98% or at least 99% sequence identity with respect to the muNS sequences indicated above, and maintaining the capacity to form inclusions when expressed in a cell. The degree of identity between two amino acid sequences can be determined by conventional methods, for example, by means of standard sequence alignment algorithms known in the state of the art, such as BLAST (Altschul et al., 1990, J Mol Biol 215:403-10), for example. The person skilled in the art will understand that the amino acid sequences referred to in this description can be chemically modified, for example, by means of physiologically relevant chemical modifications, such as phosphorylations, acetylations, etc. Methods suitable for determining the capacity of muNS, muNS-Mi or the functionally equivalent variant of muNS-Mi to generate inclusions include, but are not limited to, the method described in Example 1 of patent document WO 2011/098652 based on the expression of muNS or muNS-Mi and on the detection of the inclusions by indirect immunofluorescence using anti-muNS polyclonal antibodies, incorporated herein by reference.

The polypeptide encoded by the first polynucleotide of the invention, comprising a first component and a second component, wherein the first component is located in the N-terminal position with respect to the second component, is synthesized in the cytoplasm and translocated to the ER by means of the signal peptide comprised in said first component. The translocation of the polypeptide entails cleaving the signal peptide. Once in the ER, the polypeptide can be post-translationally modified depending on if the polypeptide contains consensus sequences for said modifications.

The authors of the present invention have demonstrated that the polypeptide encoded by the first polynucleotide of the invention surprisingly generates inclusions in the ER in a particularly more efficient manner when the second component of the polypeptide does not contain N-glycosylations.

Therefore, in a particular embodiment the second component lacks N-glycosylation consensus sequences. As it is used herein, the term "N-glycosylation consensus sequence" refers to the sequence formed by -Asn-X-Ser/Thr, wherein X is not proline, which is the most representative consensus sequence, as well as to less abundant N-glycosylation consensus sequences, such as the -Asn-Gly-, -Asn-X-Cys and -Asn-X-Val sequences.

In a preferred embodiment, the second component comprises the sequence SEQ ID NO: 11 or a functionally equivalent variant thereof, wherein the amino acid in position 57 is not an Asn residue. In an even more preferred embodiment, the second component comprises the sequence SEQ ID NO: 13.

In another preferred embodiment, the second component comprises the sequence SEQ ID NO: 12 or a functionally equivalent variant thereof, wherein the amino acid in position 104 is not an Asn residue. In an even more preferred embodiment, the second component comprises the sequence SEQ ID NO: 14.

In another preferred embodiment, the second component comprises the sequence SEQ ID NO: 12 or a functionally equivalent variant thereof, wherein the amino acid in position 160 is not an Asn residue. In an even more preferred embodiment, the second component comprises the sequence SEQ ID NO: 15.

In another preferred embodiment, the second component comprises the sequence SEQ ID NO: 12 or a functionally equivalent variant thereof, wherein the amino acids in positions 104 and 160 are not Asn residues. In an even more preferred embodiment, the second component comprises the sequence SEQ ID NO: 16.

As will be obvious for the person skilled in the art, it may be beneficial for the polypeptide encoded by the first polynucleotide of the invention to further contain a tag for facilitating purification.

Therefore, in another particular embodiment the first polynucleotide of the invention encodes a polypeptide further comprising a peptide for facilitating purification located in the C-terminal position with respect to the first component.

As it is used herein, the term "peptide for facilitating purification" refers to a peptide which is useful for isolating or purifying the second component of the polypeptide encoded by the first polynucleotide of the invention and bound to the C-terminal end with respect to the first component. Therefore, said peptide can bind one or more ligands of an affinity matrix, such as an affinity chromatography. An example of said peptide is the histidine tag (His-tag) which can contain six histidine residues (His6 or H6), which can bind to a nickel or cobalt column with high affinity. Other examples of said peptides include, but are not limited to, Arg-tag, FLAG-tag, Strep-tag, an epitope that can be recognized by an antibody, such as c-myc-tag (recognized by an anti-c-myc antibody), SBP-tag, S-tag, calmodulin-binding peptide, cellulose-binding domain, chitin-binding domain, glutathione S-transferase-tag, maltose-binding protein, NusA, TrxA, DsbA, Avi-tag, etc. The person skilled in the art will understand that the peptides for facilitating purification are also useful for detecting the polypeptide to which they are bound. This can be carried out by means of conventional techniques, for example, techniques based on antibodies specifically recognizing the peptide for facilitating purification.

The peptide for facilitating purification can be located in the N- or C-terminal position with respect to the second component. In a preferred embodiment, the peptide for facilitating purification is located in the N-terminal position with respect to the second component. In another preferred embodiment, the peptide for facilitating purification is located in the C-terminal position with respect to the second component.

The polypeptide encoded by the first polynucleotide of the invention can further contain a polypeptide of interest.

In another particular embodiment, the first polynucleotide of the invention encodes a polypeptide further comprising a polypeptide of interest located in the C-terminal position with respect to the first component.

As it is used herein, the term "polypeptide of interest" refers to any polypeptide to be included in the polypeptide encoded by the first polynucleotide of the invention in the form of a fusion protein. As it is used herein, the term "fusion protein" refers to polypeptides comprising two or more regions from different or heterologous proteins. In a preferred embodiment, said polypeptide of interest can be a viral antigen, a bacterial antigen, a fungal antigen, an allergen or environmental antigen or a tumor antigen.

Viral antigens suitable as the first component of the fusion protein of the invention include antigens of HIV-1, (such as tat, nef, gp120 or gp160, gp40, p24, gag, env, vif, vpr, vpu, rev), human herpes virus, (such as gH, gL, gM, gB, gC, gK, gE or gD or derivatives thereof) or immediate early protein such as ICP27, ICP47, ICP4, ICP36 of VHS1 or VHS2, cytomegalovirus, particularly human, (such as gB or derivatives thereof), Epstein Barr virus (such as gp350 or derivatives thereof), varicella zoster virus (such as gpl, II, Ill and IE63), or a hepatitis virus such as hepatitis B virus (for example, hepatitis B surface antigen or hepatitis nuclear antigen), hepatitis C virus (for example, nuclear antigens, E1, NS3 or NS5), paramyxovirus such as respiratory syncytial virus (such as proteins F and G or derivatives thereof), parainfluenza virus, rubella virus (such as proteins E1 and E2), measles virus, mumps virus, human papillomavirus (for example, HPV6, 11, 16, 18, LI, L2, E1, E2, E3, E4, E5, E6, E7), flavivirus (for example, yellow fever virus, dengue virus, tick-borne encephalitis virus, Japanese encephalitis virus) or cells infected with influenza virus, such as proteins HA, NP, NA or M, or combinations thereof), rotavirus antigens (such as VP7sc and other rotavirus components), and the like.

Bacterial antigens suitable as the first component of the fusion protein of the invention include antigens of *Neisseria* spp, including N gonorrhea and *N. meningitidis* (transferrin-binding proteins, lactoferrin-binding proteins, PilC and adhesins); antigens of *S. pyogenes* (such as M proteins or fragments thereof and protease C5A); antigens of *S. agalactiae, S. mutans; H. ducreyi; Moraxella* spp, including *M. catarrhalis*, also known as *Branhamella catarrhalis* (such as high and low molecular weight adhesins and invasins); antigens of *Bordetella* spp, including *B. pertussis*) (for example, *B. parapertussis* and *B. bronchiseptica* (such as pertactin, pertussis toxin or derivatives thereof, filamentous hemagglutinin, adenylate cyclase, fimbriae); antigens of *Mycobacterium* spp., including *M. tuberculosis, M. bovis, M. leprae, M. avium, M. paratuberculosis, M. smegmatis; Legionella* spp, including *L. pneumophila* (for example, ESAT6, antigen 85A, -B or -C, MPT 44, MPT59, MPT45, HSPIO, HSP65, HSP70, HSP75, HSP90, PPD of 19 kDa [Rv3763], PPD of 38 kDa [Rv0934]); antigens of *Escherichia* spp, including enterotoxic *E. coli* (for example, colonization factors, thermolabile toxin or derivatives thereof, heat-stable toxin or derivatives thereof), antigens of enterohemorrhagic *E. coli* and enteropathogenic *E. coli* (for example, toxin similar to Shiga toxin or derivatives thereof); antigens of *Vibrio* spp, including *V. cholera* (for example, cholera toxin or derivatives thereof); antigens of *Shigella* spp, including *S. sonnei, S. dysenteriae, S. flexneri; Yersinia* spp, including *Y. enterocolitica* (for example, a Yop protein); antigens of *Y. pestis, Y. pseudotuberculosis; Campylobacter* spp, including *C. jejuni* (for example, toxins, adhesins and invasins); antigens of *Salmonella* spp, including *S. typhi, S. paratyphi, S. choleraesuis, S. enteritidis; Listeria* spp., including *L. monocytogenes; Helicobacter* spp, including *H. pylori* (for example, urease, catalase, vacuolating toxin); antigens of *Pseudomonas* spp, including *P. aeruginosa; Staphylococcus* spp., including *S. aureus, S. epidermidis; Enterococcus* spp., including *E. faecalis, E. faecium; Clostridium* spp., including *C. tetani* (for example, tetanus toxin and derivative thereof); antigens of *C. botulinum* (for example, botulinum toxin and derivative thereof), antigens of *C. difficile* (for example, *clostridium* toxins A or B and derivatives thereof); antigens of *Bacillus* spp., including *B. anthracis* (for example, anthrax toxin and derivatives thereof); *Corynebacterium* spp., including *C. diphtheriae* (for example, diphtheria toxin and derivatives thereof); antigens of *Borrelia* spp., including *B. burgdorferi* (for example, OspA, OspC, DbpA, DbpB); antigens of *B. garinii* (for example, OspA, OspC, DbpA, DbpB), *B. afzelii* (for example, OspA, OspC, DbpA, DbpB), antigens of *B. andersonii* (for example, OspA, OspC, DbpA, DbpB), antigens of *B. hermsii; Ehrlichia* spp., including *E. equi* and human granulocytic ehrlichiosis agent; *Rickettsia* spp, including *R. rickettsii; Chlamydia* spp., including *C. trachomatis* (for example, MOMP, heparin-binding proteins); antigens of *Chlamydia pneumoniae* (for example, MOMP, heparin-binding proteins), antigens of *C. psittaci*; Leptospira spp., including *L. interrogans; Treponema* spp., including *T. pallidum* (for example, rare outer membrane proteins), antigens of *T. denticola, T. hyodysenteriae; Toxoplasma* spp. and *T. gondii* (for example, SAG2, SAGS, Tg34); antigens of *M. tuberculosis* (such as Rv2557, Rv2558, RPFs: Rv0837c, Rv1884c, Rv2389c, Rv2450, Rv1009, aceA (Rv0467), PstS1, (Rv0932), SodA (Rv3846), Rv2031c of 16 kDal, Tb Ra12, Tb H9, Tb Ra35, Tb38-1, Erd 14, DPV, MTI, MSL, mTTC2 and hTCC1); antigens of *Chlamydia* (such as the high molecular weight protein (HWMP), ORF3 (patent document EP 366 412) and possible membrane proteins (Pmp); antigens of *Streptococcus* spp, including *S. pneumoniae* (PsaA, PspA, streptolysin, choline-binding proteins, pneumolysin protein antigen, and detoxified mutant derivatives thereof); antigens derived from *Haemophilus* spp., including *H. influenzae* type B (for example, PRP and conjugates thereof); antigens of *H. influenzae* that cannot be classified (such as OMP26, high molecular weight adhesins, P5, P6, D protein and lipoprotein D, and fimbrin and fimbrin-derived peptides, or multiple copy variants or the fusion proteins thereof).

Fungal antigens suitable as the first component of the fusion protein of the invention include, but are not limited to, for example, fungal antigen components of *Candida*; fungal antigens of *Histoplasma* such as heat shock protein 60 (HSP60) and other fungal antigen components of *Histoplasma; Pneumocystis* spp., including *P. carinii*; fungal antigens of cryptococci such as capsular polysaccharides and other fungal antigen components of cryptococci; fungal antigens of coccidia such as spherule antigens and other fungal antigen components of coccidia; antigens of *Candida* spp., including *C. albicans*; of *Cryptococcus* spp., including *C. neoformans*; and fungal antigens of Tinea such as trichophytin and other fungal antigen components of coccidia.

Protozoal antigens suitable as the first component of the fusion protein of the invention include, but are not limited to, antigens of *Plasmodium* spp., such as *P. falciparum* and antigens derived from *Plasmodium falciparum* (such as RTS.S, TRAP, MSP1, AMA1, MSP3, EBA, GLURP, RAP1, RAP2, sequestrin, PfEMP1, Pf332, LSA1, LSA3, STARP, SALSA, PfEXP1, Pfs25, Pfs28, PFS27/25, Pfs16, Pfs48/45, Pfs230 and the analogs thereof in *Plasmodium* spp.); as well as merozoite surface antigens, sporozoite surface antigens, circumsporozoite antigens, gametocyte/gamet surface antigens, blood-type antigen pf, 55/RESA and other components of plasmoid antigens; *Toxoplasma* antigens such as SAG-I, p30 and other *Toxoplasma* antigen components; schistosome antigens such as glutathione-S-transferase, paramyosin and other schistosome antigen components; the antigen of *Trichomonas* spp., including *T. vaginalis*; antigens of *Entamoeba* spp., including *E. histolytica; Babesia* spp., including *B. microti*; the *Leishmania* antigen and other *Leishmania* antigens such as gp63, lipophosphoglycan and its associated protein and other *Leishmania* antigen components; antigens of Giardia spp., including *G. lamblia*; and *Trypanosoma cruzi* antigens such as the 75-77 kDa antigen, the 56 kDa antigen and other *Trypanosoma* antigen components.

Environmental antigens or allergens suitable as the first component of the fusion protein of the invention include, but are not limited to an antigen derived from naturally occurring allergens such as pollen allergens (allergens from tree, herb plant, weed and grass pollen), insect allergens (inhalable allergens, allergens in saliva and venom), allergens from the dander and hair of animals, and food allergens. Important pollen, tree, grass and herb allergens come from the taxonomic orders of Fagales, Oleales, Pinales and Platanaceae including, among others, birch (*Betula*), alder (*Alnus*), hazel (*Corylus*), hornbeam (*Carpinus*) and olive (*Olea*), cedar (*Cryptomeria* and *Juniperus*), banana (*Platanus*), the order of Poales including, among others, grasses of the genera *Lolium, Phleum, Poa, Cynodon, Dactylis, Holcus, Phalaris, Secale* and Sorghum, the orders of Asterales and Urticales including, among others, grasses of the genera *Ambrosia, Artemisia* and *Parietaria*. Other allergenic antigens which can be used include allergens from house dust mites of the genera *Dermatophagoides* and *Euroglyphus*, storage mites, for example *Lepidoglyphus, Glycyphagus* and *Tyrophagus*, allergens from cockroaches, midges and fleas, for example *Blattella, Periplaneta, Chironomus* and *Ctenocephalides*, allergens from mammals such as cat, dog and horse, birds, allergens from venom including those originating from bites or stings of insects such as those of the taxonomic order of Hymenoptera including bees (Apidae superfamily), wasps and ants (Formicidae superfamily). Other allergenic antigens which can be used include allergens from the inhalation of fungi such as those of the genera *Alternaria* and *Cladosporium*.

Tumor antigens suitable as the first component of the fusion protein of the invention include, but are not limited to MAGE, MART-1/Mclan-A, gp100, dipeptidyl peptidase IV (DPPIV), adenosine deaminase-binding protein (ADAbp), cyclophilin b, colorectal associated antigen (CRC)-0017-1A/GA733, carcinoembryonic antigen (CEA) and its antigenic epitopes CAP-1 and CAP-2, etv6, aml1, prostate-specific antigen (PSA) and its antigenic epitopes PSA-1, PSA-2, and PSA-3, prostate-specific membrane antigen (PSMA), CD3-ç chain/T-cell receptor, MAGE family of tumor antigens (for example, MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, MAGE-Xp2 (MAGE-B2), MAGE-Xp3 (MAGE-B3), MAGE-Xp4 (MAGE-B4), MAGE-C1, MAGE-C2, MAGE-C3, MAGE-C4, MAGE-C5), GAGE family of tumor antigens (for example, GAGE-1, GAGE-2, GAGE-3, GAGE-4, GAGE-5, GAGE-6, GAGE-7, GAGE-8, GAGE-9), BAGE, RAGE, LAGE-1, NAG, GnT-V, MUM-1, CDK4, tyrosinase, p53, MUC family, HER2/neu, p21ras, RCAS1, α-fetoprotein, E-cadherin, α-catenin, 13-catenin, γ-catenin, p12Octn, gp100Pme1117, PRAME, NY-ESO-1, cdc27, adenomatous polyposis *coli* protein (APC), fodrin, connexin 37, Ig idiotype, p15, gp75, GM2 and GD2 gangliosides, viral products such as human papillomavirus proteins, Smad family of tumor antigens, Imp-1, P1A, EBV-encoded nuclear antigen (EBNA)-1, brain glycogen phosphorylase, SSX-1, SSX-2 (HOM-MEL-40), SSX-3, SSX-4, SSX-5, SCP-1 and CT-7, and c-erbB-2, acute lymphoblastic leukemia (etv6, aml1, cyclophilin b), B-cell lymphoma (Ig idiotype), glioma (E-cadherin, a-catenin, 13-catenin, 7-catenin, p120ctn), bladder cancer (p21ras), gall bladder cancer (p21ras), breast cancer (HER2/neu, c-erbB-2, MUC family), uterine cervix carcinoma (p53, p21ras), colon carcinoma (p21ras, HER2/neu, c-erbB-2, MUC family), colorectal cancer (colorectal associated antigen (CRC)-0017-1A/GA733, APC), choriocarcinoma (CEA), epithelial cell cancer (cyclophilin b), stomach cancer (HER2/neu, c-erbB-2, glycoprotein ga733), hepatocellular cancer, Hodgkin's lymphoma (Imp-1, EBNA-1), lung cancer (CEA, MAGE-3, NY-ESO-1), lymphoid cell-derived leukemia (cyclophilin b), melanoma (protein p15, gp75, oncofetal antigen, GM2 and GD2 gangliosides, Melan-A/MART-1, cdc27, MAGE-3, p21ras, gp100Pme1117), myeloma (MUC family, p21ras), non-small cell lung carcinoma (HER2/neu, c-erbB-2), nasopharyngeal cancer (Imp-1, EBNA-1), ovarian cancer (HER2/neu, c-erbB-2, MUC family), prostate cancer (prostate-specific antigen (PSA) and its antigenic epitopes PSA-1, PSA-2 and PSA-3, PSMA, HER2/neu, c-erbB-2, glycoprotein ga733), kidney cancer (HER2/neu, c-erbB-2), cervical and esophageal squamous cell cancers (viral products such as human papillomavirus proteins), testicular cancer (NY-ESO-1) and T-cell leukemia (VLTH-1 epitopes).

The polypeptide of interest can be located in the N- or C-terminal position with respect to the second component. In a preferred embodiment, the polypeptide of interest is located in the N-terminal position with respect to the second component. In another preferred embodiment, the polypeptide of interest is located in the C-terminal position with respect to the second component.

Additionally, the two or more components of the fusion protein, such as the polypeptide of interest and the second component, for example, can be connected by a peptide the sequence of which contains a cleavage target for a protease, which thereby allows separating the two components. The protease cleavage sites suitable for incorporation in the fusion protein of the invention include enterokinase (DDDDK cleavage site; SEQ ID NO: 17), factor Xa (IEDGR cleavage site; SEQ ID NO: 18), thrombin (LVPRGS cleavage site; SEQ ID NO: 19), TEV protease (ENLYFQG cleavage site; SEQ ID NO: 20), PreScission protease (LEVLFQGP cleavage site; SEQ ID NO: 35), inteins and the like.

The present invention also contemplates the polypeptide encoded by the first polynucleotide of the invention. Therefore, another aspect of the present invention relates to a polypeptide encoded by the first polynucleotide of the invention, hereinafter "first polypeptide of the invention." In another aspect, the invention contemplates the polypeptide encoded by the first polynucleotide of the invention in which the signal sequence has been removed.

The invention also relates to a cell comprising the first polynucleotide of the invention, and to a cell comprising the first polypeptide of the invention, hereinafter "first cell of the invention."

The cell of the invention can be any prokaryotic cell or any eukaryotic cell. Virtually any cell type can be used herein, as shown in the Examples in which DF-1 cells (chicken fibroblasts) were used. Any host cell which may be transformed with the polynucleotide of the invention or which may be transformed, transfected or infected by means of a recombinant vector containing the first polynucleotide of the invention, for example animal cells (such as mammalian cells, poultry cells, insect cells, etc.), plant cells, yeasts, bacteria, etc. The cells of the invention can be obtained by means of conventional methods known by persons skilled in the art.

Regions of the muNS Protein which are Specifically and Efficiently Recruited into the Inclusions Formed by muNS or by muNS-Mi in the ER The authors of the present invention have identified that the regions of the Orthoreovirus muNS protein determining the capacity of said protein to incorporate itself into the muNS inclusions found in cells in which said protein is expressed are capable of being recruited into the inclusions formed by muNS or by muNS-Mi in the ER, as shown in Example 7.

This finding allows extending the use of said regions to "tag" proteins and cause their integration into inclusions generated by muNS, muNS-Mi, or into their respective fusions with green fluorescent protein (GFP) to aid their tracking in the ER.

Therefore, in another aspect the invention relates to a polynucleotide encoding a fusion protein, hereinafter "second polynucleotide of the invention," comprising:
(a) a first component comprising a secretory pathway signal peptide,
(b) a second component comprising a polypeptide of interest, and
(c) a third component comprising the minimum region of an Orthoreovirus muNS protein having the capacity to incorporate itself into inclusions formed by a protein comprising the minimum region of an Orthoreovirus muNS having the capacity to form inclusions when expressed in a cell or a functionally equivalent variant thereof,
wherein the first component is located in the N-terminal position with respect to the second and third components.

The terms "polynucleotide," "fusion protein," "secretory pathway signal peptide," "polypeptide of interest," "Orthoreovirus muNS protein," "minimum region of an Orthoreovirus muNS having the capacity to form inclusions when expressed in a cell" and "inclusions" have already been described in detail in the context of the first polynucleotide of the invention and the definitions and particular embodiments thereof are incorporated herein by reference.

"The minimum region of an Orthoreovirus muNS protein having the capacity to incorporate itself into inclusions formed by a protein comprising the minimum region of an Orthoreovirus muNS having the capacity to form inclusions when expressed in a cell," according to the present invention, is understood as the minimum region of an Orthoreovirus muNS protein which conserves the capacity of the complete protein to incorporate itself into the inclusions formed by an Orthoreovirus muNS protein or by the minimum region of an Orthoreovirus muNS protein having the capacity to form inclusions when expressed in a cell.

The polypeptides which are part of the third component can correspond to several avian Orthoreovirus muNS protein fragments (381-448, 448-477 (Coil 1 or C1), 477-542 (Intercoil) or 539-605 (Coil 2 or C2)) or to the corresponding sequence of the mammalian Orthoreovirus muNS protein. Therefore, in the embodiment in which the Orthoreovirus muNS protein is the avian Orthoreovirus muNS protein, the third component comprising the minimum region of an Orthoreovirus muNS protein having the capacity to incorporate itself into inclusions formed by a protein comprising the minimum region of an Orthoreovirus muNS having the capacity to form inclusions when expressed in a cell or a functionally equivalent variant thereof is selected from the group consisting of:

a polypeptide comprising the sequence SEQ ID NO: 21 or a functionally equivalent variant thereof;

a polypeptide comprising the sequence SEQ ID NO: 22 or a functionally equivalent variant thereof;

a polypeptide comprising the sequence SEQ ID NO: 23 or a functionally equivalent variant thereof; and a polypeptide comprising the sequence SEQ ID NO: 24 or a functionally equivalent variant thereof.

On the other hand, in the embodiment in which the Orthoreovirus muNS protein is the mammalian Orthoreovirus muNS protein, the third component comprising the minimum region of an Orthoreovirus muNS protein having the capacity to incorporate itself into inclusions formed by a protein comprising the minimum region of an Orthoreovirus muNS having the capacity to form inclusions when expressed in a cell is selected from the group consisting of:

a polypeptide comprising the mammalian Orthoreovirus muNS protein sequence corresponding to the sequence SEQ ID NO: 21 of the avian Orthoreovirus muNS protein or a functionally equivalent variant thereof;

a polypeptide comprising the mammalian Orthoreovirus muNS protein sequence corresponding to the sequence SEQ ID NO: 22 of the avian Orthoreovirus muNS protein or a functionally equivalent variant thereof;

a polypeptide comprising the mammalian Orthoreovirus muNS protein sequence corresponding to the sequence SEQ ID NO: 23 of the avian Orthoreovirus muNS protein or a functionally equivalent variant thereof; and a polypeptide comprising the mammalian Orthoreovirus muNS protein sequence corresponding to the sequence SEQ ID NO: 24 of the avian Orthoreovirus muNS protein or a functionally equivalent variant thereof.

Said muNS protein fragments are capable of directing the second component bound or not bound to the first component, i.e., the polypeptide of interest bound or not bound to the secretory pathway signal sequence, to the inclusions since they specifically interact with other muNS proteins. In order to determine the mammalian Orthoreovirus muNS protein sequence corresponding to said avian Orthoreovirus muNS protein fragments, an alignment can be carried out between the avian muNS protein sequence and the mammalian muNS protein sequence. Said sequence alignment can be carried out by means of conventional methods known by the person skilled in the art. Optimum sequence alignments can be carried out, for example, with the Smith-Waterman local homology algorithm (Adv. Appl. Math., 1981, 2:482), Needleman-Wunsch homology alignment algorithm, (J. Mol. Biol., 1970, 48:443), by means of a similarity search with the Pearson-Lipman method, (Proc. Natl Acad. Sci. USA, 1988, 85:2444), computerized implementation of these algorithms (GAP, BESTFIT, FASTA, and TFASTA in the Wisconsin Genetics Software Package, Genetics Computer Group, 575 Science Dr., Madison, Wis.), or manual alignment and visual inspection (Current Protocols in Molecular Biology (Ausubel et al., eds. 1995 supplement).

The polypeptides which are part of the third component can refer to functionally equivalent variants of the mentioned Orthoreovirus muNS protein fragments. "Functionally equivalent variant" is understood as all those peptides derived from the muNS sequence by means of modification, insertion and/or deletion of one or more amino acids, provided that the function of the aforementioned muNS proteins is substantially maintained. Specifically, the functionally equivalent variant shows at least one function related to the capacity to incorporate itself into the inclusions formed by the complete protein or muNS-Mi in a cell. Methods suitable for determining the capacity to be incorporated into the inclusions include, but are not limited to the method described in Example 3 of patent document WO 2011/098652 based on the formation of inclusions and the expression of the protein of interest in the form of fusion protein associated with the fragments directing it to the inclusions, incorporated herein by reference. Indirect immunofluorescence would then be carried out using polyclonal antibodies specific against the HA epitope or the epitope of interest, the incorporation of said fragments into the inclusions being able to be confirmed. Variants suitable for use thereof in the present invention include those which shows at least 25%, at least 40%, at least 60%, at least 70%, at least 80%, at least 90%, at least 95%, at least 96%, at least 97%, at least 98% or at least 99% sequence identity with respect to the muNS sequences indicated above and which maintains the capacity of the muNS protein to incorporate itself into inclusions formed by a protein comprising the minimum region of an Orthoreovirus muNS having the capacity to form inclusions when expressed in a cell. The degree of identity between two amino acid sequences can be determined by conventional methods, for example, by means of standard sequence alignment algorithms known in the state of the art, such as BLAST, for example (Altschul S. F. et al., 1990, cited ad supra). The person skilled in the art will understand that the amino acid sequences referred to in this description can be chemically modified, for example, by means of physiologically relevant chemical modifications, such as phosphorylations, acetylations, etc.

In a particular embodiment, the minimum region of an Orthoreovirus muNS protein having the capacity to incorporate itself into inclusions formed by a protein comprising the minimum region of an Orthoreovirus muNS having the capacity to form inclusions when expressed in a cell or the functionally equivalent variant thereof lacks N-glycosylation consensus sequences. The term "N-glycosylation consensus sequence" has been described in detail in the context of the first polynucleotide of the invention and the definition and particular embodiments thereof similarly apply here.

In a preferred embodiment, the third component comprises the sequence SEQ ID NO: 25 (corresponding to amino acids 477-542 of the avian Orthoreovirus muNS protein, wherein position 28 of SEQ ID NO: 25 is any amino acid except Asn). In an even more preferred embodiment, the third component comprises the sequence SEQ ID NO: 26

(corresponding to amino acids 477-542 of the avian Orthoreovirus muNS protein, wherein position 28 of SEQ ID NO: 26 is Ser).

The first component comprising a secretory pathway signal sequence is located in the N-terminal position with respect to the second and third components. The second component comprising a polypeptide of interest can be located in the N- or C-terminal position with respect to the third component. In a preferred embodiment, the second component is located in the N-terminal position with respect to the third component. In another preferred embodiment, the second component is located in the C-terminal position with respect to the third component.

Additionally, in another particular embodiment the second and third components of the fusion protein are connected by a peptide the sequence of which contains a cleavage target for a protease, which thereby allows separating the two components. The protease cleavage sites suitable for incorporation in the fusion protein of the invention include enterokinase (SEQ ID NO: 17), factor Xa (SEQ ID NO: 18), thrombin (SEQ ID NO: 19), TEV protease (SEQ ID NO: 20), PreScission protease (SEQ ID NO: 35), inteins and the like.

As will be obvious for the person skilled in the art, it may be beneficial for the polypeptide encoded by the second polynucleotide of the invention to further contain a tag for facilitating purification.

Therefore, in another particular embodiment the second polynucleotide of the invention encodes a fusion protein further comprising a peptide for facilitating purification located in the C-terminal position with respect to the first component. In the particular embodiment in which the second and third components of the fusion protein are connected by a peptide the sequence of which contains a cleavage target for a protease, the peptide for facilitating purification is located in the C-terminal position with respect to the first component and in the N-terminal position with respect to the third component. Therefore, in a preferred embodiment the peptide for facilitating purification is located in the N-terminal position with respect to the second component. In another preferred embodiment, the peptide for facilitating purification is located in the C-terminal position with respect to the second component.

The term "peptide for facilitating purification" has already been described in detail in the context of the first polynucleotide of the invention and the definition and particular embodiments thereof similarly apply here.

The present invention also contemplates the fusion protein encoded by the second polynucleotide of the invention. Therefore, another aspect of the present invention relates to a fusion protein encoded by the second polynucleotide of the invention, hereinafter "fusion protein of the invention."

The invention also relates to a cell comprising the second polynucleotide of the invention, and to a cell comprising the fusion protein of the invention, hereinafter "second cell of the invention."

The cell that can be used for carrying out this aspect has been described in relation to the first polynucleotide of the invention, so reference will be made thereto in this aspect.

Kit of the Invention

The invention also provides kits which are suitable for putting the method of the invention into practice. Therefore, in another aspect the invention relates to a kit, hereinafter "kit of the invention," comprising:

(a) component A comprising
a polynucleotide encoding a polypeptide comprising
(i) component A1 comprising a secretory pathway signal peptide, and
(ii) component A2 comprising the minimum region of an Orthoreovirus muNS protein having the capacity to form inclusions when expressed in a cell or a functionally equivalent variant thereof,
wherein the first component is located in the N-terminal position with respect to the second component;
or
a cell expressing a polynucleotide encoding a polypeptide comprising
(i) component A1 comprising a secretory pathway signal peptide, and
(ii) component A2 comprising the minimum region of an Orthoreovirus muNS protein having the capacity to form inclusions when expressed in a cell or a functionally equivalent variant thereof,
wherein the first component is located in the N-terminal position with respect to the second component;
and
(b) component B comprising a polynucleotide encoding a fusion protein comprising:
component B1 comprising a secretory pathway signal peptide,
component B2 comprising a polypeptide of interest, and
component B3 comprising the minimum region of an Orthoreovirus muNS protein having the capacity to incorporate itself into inclusions formed by a protein comprising the minimum region of an Orthoreovirus muNS having the capacity to form inclusions when expressed in a cell or a functionally equivalent variant thereof,
wherein the first component is located in the N-terminal position with respect to the second and third components.

As it used herein, the term "kit" is used to refer to a combination of components facilitating a process, method, assay, analysis or handling of a sample. These kits provide the materials required for carrying out the methods described in the present invention.

The kit of the invention comprises component A comprising a polynucleotide encoding a polypeptide comprising component A1 comprising a secretory pathway signal peptide, and component A2 comprising the minimum region of an Orthoreovirus muNS protein having the capacity to form inclusions when expressed in a cell or a functionally equivalent variant thereof, wherein the first component is located in the N-terminal position with respect to the second component. In other words, the first component of the kit of the invention comprises the first polynucleotide of the invention. Likewise, the kit can comprise, as the first component, the cell expressing said first polynucleotide of the invention.

The first polynucleotide of the invention has been described in detail above, and the definitions and particular embodiments thereof are incorporated herein by reference.

The kit comprises, as the second component, component B comprising a polynucleotide encoding a fusion protein comprising component B1 comprising a secretory pathway signal peptide, component B2 comprising a polypeptide of interest, and component B3 comprising the minimum region of an Orthoreovirus muNS protein having the capacity to incorporate itself into inclusions formed by a protein comprising the minimum region of an Orthoreovirus muNS having the capacity to form inclusions when expressed in a cell or a functionally equivalent variant thereof, wherein the first component is located in the N-terminal position with respect to the second and third components. In other words, the second component of the kit of the invention comprises the second polynucleotide of the invention.

The second polynucleotide of the invention has been described in detail above, and the definitions and particular embodiments thereof are incorporated herein by reference.

Additionally, the kit of the invention can comprise a cell suitable for putting the kit into practice. Said cell can be a prokaryotic cell or a eukaryotic cell. Virtually any host cell that may be transformed with the polynucleotides of the invention or that may be transformed, transfected or infected by means of a recombinant vector containing the first polynucleotide, the second polynucleotide or both polynucleotides of the invention can be used in the kit of the invention, for example animal cells (such as mammalian cells, poultry cells, insect cells, etc.), plant cells, yeasts, etc. The cells of the invention can be obtained by means of conventional methods known by persons skilled in the art.

Purification Methods for Purifying Inclusions Formed by muNS-Mi in the ER

The inclusions generated by the expression of the polynucleotide encoding a polypeptide comprising a first component comprising a secretory pathway signal peptide, and a second component comprising the minimum region of an Orthoreovirus muNS protein having the capacity to form inclusions when expressed in a cell or a functionally equivalent variant thereof, wherein the first component is located in the N-terminal position with respect to the second component, i.e., the first polynucleotide of the invention, can be readily purified by means of the method described in the "Methods" section of the examples of patent document WO 2011/098652 incorporated herein by reference.

Therefore, in another aspect the present invention relates to a purification method for purifying a polypeptide comprising the minimum region of an Orthoreovirus muNS protein having the capacity to form inclusions when expressed in a cell, hereinafter "inclusion purification method of the invention," wherein said method comprises (i) expressing in a cell a polynucleotide encoding a polypeptide comprising
(a) a first component comprising a secretory pathway signal peptide, and
(b) a second component comprising the minimum region of an Orthoreovirus muNS protein having the capacity to form inclusions when expressed in a cell or a functionally equivalent variant thereof,
wherein the first component is located in the N-terminal position with respect to the second component, and wherein the polypeptide further comprises a polypeptide of interest located in the C-terminal position with respect to the first component,
under conditions suitable for the translocation of the polypeptide to the secretory pathway and the formation of inclusions from said minimum region, and
(ii) purifying the inclusions formed in step (i).

The terms "polypeptide," "minimum region of an Orthoreovirus muNS protein having the capacity to form inclusions when expressed in a cell," "inclusion," "cell," "polynucleotide," "secretory pathway signal peptide" and "polypeptide of interest" have been described in detail in the context of the first polynucleotide of the invention and the definitions and particular embodiments thereof similarly apply here.

In a first step (i), the inclusion purification method of the invention comprises expressing in a cell a polynucleotide encoding a polypeptide comprising a first component comprising a secretory pathway signal peptide, and a second component comprising the minimum region of an Orthoreovirus muNS protein having the capacity to form inclusions when expressed in a cell or a functionally equivalent variant thereof, wherein the first component is located in the N-terminal position with respect to the second component, and wherein the polypeptide further comprises a polypeptide of interest located in the C-terminal position with respect to the first component, under conditions suitable for the translocation of the polypeptide to the secretory pathway and the formation of inclusions from said minimum region. In other words, in a first step the first purification method comprises expressing in a cell the first polynucleotide of the invention wherein the polypeptide further comprises a polypeptide of interest located in the C-terminal position with respect to the first component, under conditions suitable for the translocation of the polypeptide to the secretory pathway and the formation of inclusions from said minimum region. The first polynucleotide of the invention has been described in detail above, and the definitions and particular embodiments thereof also apply to the inclusion purification method of the invention.

As will be obvious for the person skilled in the art, the inclusion purification method of the invention is particularly advantageous for purifying a polypeptide of interest. Therefore, to carry out this method the first polynucleotide of the invention must encode a polypeptide further comprising a polypeptide of interest located in the C-terminal position with respect to the first component.

The polynucleotide encoding a polypeptide comprising a first component comprising a secretory pathway signal peptide, and a second component comprising the minimum region of an Orthoreovirus muNS protein having the capacity to form inclusions when expressed in a cell or a functionally equivalent variant thereof, wherein the first component is located in the N-terminal position with respect to the second component, and wherein the polypeptide further comprises a polypeptide of interest located in the C-terminal position with respect to the first component, can be introduced into host cells using well-known techniques such as infection, transduction, transfection, transvection, electroporation and transformation. Such methods are described in many standard laboratory manuals. The vector can be, for example, a phage, a plasmid, viral or retroviral vector. The cells comprising the gene construct may have been transitorily or stably transfected, for which the transfection of the gene construct is carried out simultaneously with a gene providing resistance to a specific antibiotic, such that those cell lines which have incorporated the DNA into the genome of those cell lines in which the DNA is located in an extrachromosomal position can be selected. The gene which allows selecting the cells can be provided forming part of the same vector containing the construct object of the invention, or alternatively, they can be provided separately by means of co-transfection with a second plasmid containing said resistance gene. The process of selecting cells containing some or all the DNA constructs of the components of the first complex of the invention stably integrated into the genome is carried out by means of a selection process. To that end, the cells are transfected with the vector or mixtures of vectors, and after a recovery period, they are left to grow in a selective medium (either a medium containing the antibiotic against which the reporter gene confers resistance or a minimum medium containing the antimetabolite against which the reporter gene confers resistance). The cell colonies growing in the selective medium are isolated and again left to grow in a selective medium.

In order to successfully generate the inclusions in a cell, said cell must be kept under suitable conditions so that the translocation of the polypeptide to the secretory pathway and the formation of inclusions are favored. As it is used herein, the term "conditions suitable for the translocation of the polypeptide to the secretory pathway and the formation of inclusions" refers to the cell culture conditions which allow the polypeptide to be translocated into the ER simultaneously with respect to the translation thereof, or post-translationally, and to spontaneously form inclusions. The translocation is mediated by the secretory pathway signal peptide comprised in the first component of the polypeptide encoded by the first polynucleotide of the invention, said signal peptide being cleaved, whereas the formation of inclusions is mediated by the minimum region of an Orthoreovirus muNS protein having the capacity to form inclusions when expressed in a cell comprised in the second component. The conditions suitable for the translocation of the polypeptide to the secretory pathway and the formation of inclusions include, without limitation, the culture conditions suitable for the cell. A person skilled in the art would know what type of conditions is optimum for each cell type in which the inclusions are expressed in the ER. The selection of said media and culture conditions will depend on the microorganism or cell line selected for producing the inclusions in the ER. The culture conditions suitable for the cell include pH, temperature, gas concentration, carbon source, nitrogen source, culture time and stirring conditions. For example, the culture conditions for insect cell line Sf9 comprise Grace's insect medium supplemented, 100% air, at 28° C. and 120 rpm for 3 days.

The person skilled in the art would know what methods to use in order to check if the inclusions have been suitably formed. Methods suitable for determining if the inclusions have been generated include, but are not limited to, the detection thereof by indirect immunofluorescence using anti-muNS polyclonal antibodies.

Once the inclusions have been formed in the cell, the second step consists of purifying said inclusions. To that end, the first step would be to cause lysis of the cell by sonication or by any other method known by the person skilled in the art such as by means of several passes in a French press, by means of homogenization using a Polytron. The inclusions are obtained after centrifuging the pellet or precipitate which will subsequently be resuspended in a suitable buffer. Methods suitable for separating the aggregates from the other components present in the sample include, without limitation, differential centrifugation, sedimentation, filtration, density gradient separation and the like. In a preferred embodiment, the inclusion purification method is the method described in patent document WO 2011/098652, incorporated herein by reference.

In a particular embodiment, the second component of the polypeptide encoded by the polynucleotide comprises the minimum region of the avian Orthoreovirus muNS protein having the capacity to form inclusions when expressed in a cell corresponding to the sequence of SEQ ID NO: 11 or a functionally equivalent variant thereof.

In another particular embodiment, the second component of the polypeptide encoded by the polynucleotide comprises the minimum region of the mammalian Orthoreovirus muNS protein having the capacity to form inclusions when expressed in a cell corresponding to the sequence of SEQ ID NO: 12 or a functionally equivalent variant thereof.

In order to make use of the unexpected greater inclusion-forming efficiency of the minimum region of an Orthoreovirus muNS protein when it lacks N-glycosylations, the use of a polynucleotide encoding a polypeptide the second component of which lacks or does not contain N-glycosylations is particularly advantageous for the inclusion purification method of the invention.

Therefore, in another particular embodiment the second component lacks N-glycosylation consensus sequences. The term "N-glycosylation consensus sequence" has been defined in detail in the context of the first polynucleotide of the invention and the definition and particular embodiments thereof are included herein by reference.

In a preferred embodiment, the second component comprises the sequence SEQ ID NO: 11 or a functionally equivalent variant thereof, wherein the amino acid in position 57 is not an Asn residue. In an even more preferred embodiment, the second component comprises the sequence SEQ ID NO: 13.

In another preferred embodiment, the second component comprises the sequence SEQ ID NO: 12 or a functionally equivalent variant thereof, wherein the amino acid in position 104 is not an Asn residue. In an even more preferred embodiment, the second component comprises the sequence SEQ ID NO: 14.

In another preferred embodiment, the second component comprises the sequence SEQ ID NO: 12 or a functionally equivalent variant thereof, wherein the amino acid in position 160 is not an Asn residue. In an even more preferred embodiment, the second component comprises the sequence SEQ ID NO: 15.

In another preferred embodiment, the second component comprises the sequence SEQ ID NO: 12 or a functionally equivalent variant thereof, wherein the amino acids in position 104 and 160 are not Asn residues. In an even more preferred embodiment, the second component comprises the sequence SEQ ID NO: 16.

As will be obvious for the person skilled in the art, it may be beneficial for the polypeptide to further contain a tag for facilitating purification. Therefore, in another particular embodiment the first polynucleotide of the invention encodes a polypeptide further comprising a peptide for facilitating purification located in the C-terminal position with respect to the first component. The term "peptide for facilitating purification" has been defined in detail in the context of the first polynucleotide of the invention and the definition and particular embodiments thereof are included herein by reference.

In another particular embodiment, the polypeptide of interest and the second component comprising the minimum region of an Orthoreovirus muNS protein having the capacity to form inclusions when expressed in a cell or a functionally equivalent variant thereof are connected by a peptide the sequence of which contains a cleavage target for a protease.

This embodiment allows incubating the purified inclusions with a protease specific for said target sequence. The result is the cleavage of the polypeptide of interest from the inclusion. Finally, the polypeptide of interest can be purified by techniques suitable for purification which depend on the nature of the polypeptide of interest and will be known by the person skilled in the art. Polypeptide purification techniques are widely known in the art and include, without limitation, affinity chromatography, exclusion chromatography, ion exchange chromatography, adsorption chromatography, immunoprecipitation, etc.

Purification Methods for Purifying Fusion Proteins
1. First Fusion Protein Purification Method of the Invention The inclusions generated by muNS-Mi in the ER can be readily purified with the inclusion purification method of the invention, so if a protein is selectively directed to said inclusions in the ER said protein could also be purified in a simple and efficient manner. Furthermore, said purified protein maintains its biological activity.

Therefore, in another aspect the invention relates to a purification method for purifying a fusion protein comprising a polypeptide of interest and the minimum region of an Orthoreovirus muNS protein having the capacity to incorporate itself into the inclusions formed by a protein comprising the minimum region of an Orthoreovirus muNS having the capacity to form inclusions when expressed in a cell, hereinafter "first fusion protein purification method of the invention" wherein said method comprises
(i) expressing in a cell a first polynucleotide, wherein said first polynucleotide encodes a polypeptide comprising
(a) a first component comprising a secretory pathway signal peptide, and
(b) a second component comprising the minimum region of an Orthoreovirus muNS protein having the capacity to form inclusions when expressed in a cell or a functionally equivalent variant thereof,
wherein the first component is located in the N-terminal position with respect to the second component,
under conditions suitable for the translocation of the polypeptide to the secretory pathway and the formation of inclusions from said minimum region,
(ii) expressing in said cell a second polynucleotide, wherein said second polynucleotide is a polynucleotide encoding a fusion protein comprising:
(a) a first component comprising a secretory pathway signal peptide,
(b) a second component comprising a polypeptide of interest, and
(c) a third component comprising the minimum region of an Orthoreovirus muNS protein having the capacity to incorporate itself into inclusions formed by a protein comprising the minimum region of an Orthoreovirus muNS having the capacity to form inclusions when expressed in a cell or a functionally equivalent variant thereof,
wherein the first component is located in the N-terminal position with respect to the second and third components, under conditions suitable for the translocation of the fusion protein to the secretory pathway and for the recruitment of the fusion protein into the inclusions formed in step (i), and
(iii) purifying the complexes comprising the inclusions formed in step (i) and the fusion proteins produced in step (ii),
wherein steps (i) and (ii) can be carried out in any order.

The terms "fusion protein," "polypeptide," "minimum region of an Orthoreovirus muNS protein having the capacity to form inclusions when expressed in a cell," "inclusion," "cell," "polynucleotide," "secretory pathway signal peptide," "polypeptide of interest," "polypeptide," "minimum region of an Orthoreovirus muNS protein having the capacity to incorporate itself into inclusions formed by a protein comprising the minimum region of an Orthoreovirus muNS having the capacity to form inclusions when expressed in a cell" and "conditions suitable for the translocation of the polypeptide to the secretory pathway and the formation of inclusions" have been described in detail in the context of the first polynucleotide of the invention and the definitions and particular embodiments thereof similarly apply here.

In a first step (i), the first fusion protein purification method of the invention comprises expressing in a cell a first polynucleotide, wherein said first polynucleotide encodes a polypeptide comprising a first component comprising a secretory pathway signal peptide, and a second component comprising the minimum region of an Orthoreovirus muNS protein having the capacity to form inclusions when expressed in a cell or a functionally equivalent variant thereof, wherein the first component is located in the N-terminal position with respect to the second component, under conditions suitable for the translocation of the polypeptide to the secretory pathway and the formation of inclusions from said minimum region. In other words, in a first step the first fusion protein purification method of the invention comprises expressing the first polynucleotide of the invention under conditions suitable for the translocation of the polypeptide to the secretory pathway and the formation of inclusions from said minimum region. The first polynucleotide of the invention has been described in detail above and the definitions and particular embodiments thereof also apply to the first fusion protein purification method of the invention.

The person skilled in the art will see that the first step of the first fusion protein purification method of the invention is the same as the first step of the inclusion purification method of the invention described in detail above. Therefore, the definitions and particular embodiments of the first step of the inclusion purification method of the invention are included herein by reference.

In a second step (ii), the first fusion protein purification method of the invention comprises expressing in a cell a second polynucleotide, wherein said second polynucleotide is a polynucleotide encoding a fusion protein comprising a first component comprising a secretory pathway signal peptide, a second component comprising a polypeptide of interest, and a third component comprising the minimum region of an Orthoreovirus muNS protein having the capacity to incorporate itself into inclusions formed by a protein comprising the minimum region of an Orthoreovirus muNS having the capacity to form inclusions when expressed in a cell or a functionally equivalent variant thereof, wherein the first component is located in the N-terminal position with respect to the second and third components, under conditions suitable for the translocation of the fusion protein to the secretory pathway and for the recruitment of the fusion protein into the inclusions produced in step (i). In other words, in a second step the first fusion protein purification method of the invention comprises expressing the second polynucleotide of the invention under conditions suitable for the translocation of the fusion protein to the secretory pathway and for the recruitment of the fusion protein into the inclusions formed in step (i). The second polynucleotide of the invention has been described in detail above and the definitions and particular embodiments thereof also apply to the first fusion protein purification method of the invention.

The second polynucleotide of the invention can be introduced into host cells using well-known techniques such as infection, transduction, transfection, transvection, electroporation and transformation. Such methods are described in many standard laboratory manuals. The vector can be, for example, a phage, a plasmid, viral or retroviral vector. The cells comprising the gene construct may have been transitorily or stably transfected, for which the transfection of the gene construct is carried out simultaneously with a gene providing resistance to a specific antibiotic, such that those cell lines which have incorporated the DNA into the genome of those cell lines in which the DNA is located in an extrachromosomal position can be selected. The gene which allows selecting the cells can be provided forming part of the same vector containing the construct object of the invention, or alternatively, they can be provided separately by means of co-transfection with a second plasmid containing said resistance gene. The process of selecting cells containing some or all the DNA constructs of the components of the first complex of the invention stably integrated into the genome is carried out by means of a selection process. To that end, the cells are transfected with the vector or mixtures of vectors, and after a recovery period, they are left to grow in a selective medium (either a medium containing the antibiotic against which the reporter gene confers resistance or a minimum medium containing the antimetabolite against which the reporter gene confers resistance). The cell colonies growing in the selective medium are isolated and again left to grow in a selective medium.

In order to successfully incorporate the fusion protein into the inclusions formed in the ER in step (i), said cell must be kept under suitable conditions so that the translocation of the polypeptide to the secretory pathway and the incorporation into the inclusions are favored. As it is used herein, the term "conditions suitable for the translocation of the fusion protein to the secretory pathway and for the recruitment of the fusion protein into the inclusions" refers to the cell culture conditions which allow the fusion protein to be translocated into the ER simultaneously with respect to the translation thereof, or post-translationally, and to be spontaneously incorporated into the existing inclusions. The translocation is mediated by the secretory pathway signal peptide comprised in the first component of the fusion protein encoded by the second polynucleotide of the invention, said signal peptide being cleaved, whereas the incorporation of the fusion protein into the inclusions is mediated by the minimum region of an Orthoreovirus muNS protein having the capacity to incorporate itself into inclusions formed by a protein comprising the minimum region of an Orthoreovirus muNS having the capacity to form inclusions when expressed in a cell comprised in the third component of the fusion protein. The conditions suitable for the translocation of the polypeptide to the secretory pathway and for incorporation into the inclusions include, without limitation, the culture conditions suitable for the cell. A person skilled in the art would know what type of conditions is optimum for each cell type in which the inclusions are expressed in the ER. The selection of said media and culture conditions will depend on the microorganism or cell line selected for producing the inclusions in the ER. The culture conditions suitable for the cell include pH, temperature, gas concentration, carbon source, nitrogen source, culture time and stirring conditions. For example, the culture conditions for insect cell line Sf9 comprise Grace's insect medium supplemented, 100% air, at 28° C. and 120 rpm for 3 days.

The person skilled in the art would know what methods to use in order to check if the inclusions have been formed and if the fusion protein has been suitably incorporated into the inclusions. Methods suitable for determining if the inclusions have been generated include, but are not limited to, the detection thereof by indirect immunofluorescence using anti-muNS polyclonal antibodies. Similarly, methods suitable for determining if the fusion protein has been incorporated into the inclusions include, but are not limited to, the detection thereof by indirect immunofluorescence using polyclonal antibodies against the polypeptide of interest comprised in the fusion protein.

The result of the first and second steps (i) and (ii) of the first fusion protein purification method of the invention will be the formation of complexes between the fusion protein and the inclusions through one of the regions described above having affinity for the inclusions.

Steps (i) and (ii) of the first fusion protein purification method of the invention can be carried out in any order. Therefore, in a particular embodiment the order of the steps is (i), (ii) and (iii). In another particular embodiment, the order of the steps is (ii), (i) and (iii).

Once the inclusions have been formed in the ER and the fusion protein incorporated therein, the third step (iii) consists of purifying the complexes comprising the inclusions formed in step (i) and the fusion proteins produced in step (ii).

Purification of the complexes first requires the cells to be lysed and the complexes to be released into the medium. Once the complexes have been released into the medium, they are purified using conventional methods for purifying inclusion bodies, as described above in the context of the inclusion purification method of the invention. Methods suitable for separating the aggregates from the other components present in the sample include, without limitation, differential centrifugation, sedimentation, filtration, density gradient separation and the like.

Once a preparation consisting of complexes formed by the inclusions and the fusion protein is available, the fusion protein can be separated from the inclusions. Therefore, in another particular embodiment the first fusion protein purification method of the invention further comprises separating the fusion protein from the inclusions.

To that end, the inclusions can be solubilized using chaotropic agents such as, without limitation, urea (4 M to 8 M), formamide (at least 80% v/v) and guanidinium hydrochloride (4 M to 8 M). Some solvents which are capable of solubilizing aggregates include, for example, SDS and formic acid, although the use thereof is unsuitable due to the lack of immunogenicity and/or activity. Once the protein bodies have been solubilized, the fusion proteins can be recovered by means of removing (by means of dialysis, for example) or diluting the denaturing agent, the formation of immunologically active or biologically active fusion proteins thereby being allowed. Likewise, the separation of the fusion protein from the inclusions can be carried out in the presence of a hypertonic buffer using a NaCl concentration of about 0.5 M, obtaining the fusion protein in solution with a high purity. In a particular embodiment, said hypertonic buffer does not have divalent ions.

In a particular embodiment, the polypeptide of interest and the third component comprised in the fusion protein are connected by a peptide the sequence of which contains a cleavage target for a protease. This embodiment allows incubating the purified inclusions with a protease specific for said target sequence. The protease cleavage sites suitable for incorporation in the polypeptides of the invention include enterokinase (SEQ ID NO: 17), factor Xa (SEQ ID NO: 18), thrombin (SEQ ID NO: 19), TEV protease (SEQ ID NO: 20), PreScission protease (SEQ ID NO: 35), inteins and the like. A person skilled in the art would know the specific cleavage conditions of each of the proteases.

The result is the cleavage of the polypeptide of interest from the fusion protein incorporated in the inclusion. Finally, the polypeptide of interest can be purified by techniques suitable for purification which depend on the nature of the polypeptide of interest and will be known by the person skilled in the art. Polypeptide purification techniques are widely known in the art and include, without limitation, affinity chromatography, exclusion chromatography, ion exchange chromatography, adsorption chromatography, immunoprecipitation, etc.

In order to make use of the unexpected greater inclusion-forming efficiency of the minimum region of an Orthoreovirus muNS protein when it lacks N-glycosylations, the use of a polynucleotide encoding a polypeptide the second component of which lacks or does not contain N-glycosylations is particularly advantageous for the inclusion purification method of the invention.

Therefore, in another particular embodiment the second component of the first polynucleotide of the invention lacks N-glycosylation consensus sequences. The term "N-glycosylation consensus sequence" has been defined in detail in the context of the first polynucleotide of the invention and the definition and particular embodiments thereof are included herein by reference.

2. Second Fusion Protein Purification Method of the Invention

Alternatively, the fusion protein can be purified using preformed inclusions. Therefore, in another aspect the invention relates to a method for purifying a fusion protein comprising
(a) a polypeptide of interest, and
(b) the minimum region of an Orthoreovirus muNS protein having the capacity to incorporate itself into inclusions formed by a protein comprising the minimum region of an Orthoreovirus muNS having the capacity to form inclusions when expressed in a cell,
from a composition containing said fusion protein, hereinafter "second fusion protein purification method of the invention," wherein said method comprises:
(i) contacting said composition with inclusions formed by a polypeptide comprising the minimum region of an Orthoreovirus muNS protein having the capacity to form inclusions when expressed in a cell and lacking N-glycosylation consensus sequences under conditions suitable for the recruitment of the fusion protein into said inclusions;
(ii) purifying the complex formed between the inclusions and the fusion protein of step (i).

The terms "fusion protein," "polypeptide of interest," "minimum region of an Orthoreovirus muNS protein having the capacity to incorporate itself into inclusions formed by a protein which comprises the minimum region of an Orthoreovirus muNS having the capacity to form inclusions when expressed in a cell," "inclusion," "cell," "polypeptide," "minimum region of an Orthoreovirus muNS protein having the capacity to form inclusions when expressed in a cell and lacking N-glycosylation consensus sequences under conditions suitable for the recruitment of the fusion protein into said inclusions" have been described in detail in the context of the first polynucleotide of the invention and the definitions and particular embodiments thereof similarly apply here.

In the context of the second fusion protein purification method of the invention, the term "composition comprising the fusion protein" is used to refer to the fact that the fusion protein is not pure and can be found in a cell extract or forming part of a mixture of proteins or other components, preferably originating from cell lysis.

In a first step (i), the second fusion protein purification method of the invention comprises contacting a composition containing said fusion protein with inclusions formed by a polypeptide comprising the minimum region of an Orthoreovirus muNS protein having the capacity to form inclusions when expressed in a cell and lacking N-glycosylation consensus sequences under conditions suitable for the recruitment of the fusion protein into said inclusions. In other words, the inclusions preformed by the first polypeptide of the invention lacking N-glycosylation consensus sequences are used in the first step (i) under conditions suitable for the recruitment of the fusion protein into said inclusions. The first polynucleotide of the invention lacking N-glycosylation consensus sequences under conditions suitable for the recruitment of the fusion protein into said inclusions has been described in detail above and the definitions and particular embodiments thereof also apply to the second fusion protein purification method of the invention. The fusion protein of the invention is also used in step (i). The fusion protein of the invention has been described in detail above and the definitions and particular embodiments thereof also apply to the second fusion protein purification method of the invention.

As it is used herein, the term "conditions suitable for the recruitment of the fusion protein into inclusions" refers to the conditions which allow incorporating the fusion protein into the inclusions formed by a polypeptide comprising the minimum region of an Orthoreovirus muNS protein having the capacity to form inclusions when expressed in a cell and lacking N-glycosylation consensus sequences. The conditions suitable for the recruitment of the fusion protein into inclusions include the buffer suitable for the fusion protein and temperature and at least one divalent cation at a concentration of at least 0.5 mM should be included. A person skilled in the art would know what type of conditions is optimum for each type of fusion protein. The selection of said buffers will depend on the fusion protein selected for purification. For example, the conditions for the recruitment of the fusion protein into inclusions can comprise PBS buffer at 25° C.

As it is used herein, the term "divalent cation" refers to a positively charged ion of any metal from the periodic table having a valence of 2. Divalent cations suitable for use in the present invention include, without limitation, the divalent cations of Mg, Cd, Ca, Co, Cu, Fe, Mn, Ni, Sr and Zn. In a preferred embodiment, the divalent cation is $Mg^{2+}$. Divalent cation concentrations suitable for inducing the formation of muNS protein aggregates are, for example, at least 0.01 mM, at least 0.1 mM, at least 1 mM, at least 2 mM, at least 3 mM, at least 4 mM, at least 5 mM or higher.

Step (i) is carried out for the time required for the formation of complexes to take place from the inclusions formed by a polypeptide comprising the minimum region of an Orthoreovirus muNS protein having the capacity to form inclusions when expressed in a cell and lacking N-glycosylation consensus sequences and the fusion protein. This can be determined, for example, by means of conventional techniques for determining if a protein is in a soluble form at a specific concentration, such as turbidimetric methods, such as nephelometry, filtration and the like.

The person skilled in the art would know what methods to use in order to check if the fusion protein has been suitably incorporated into the inclusions. Methods suitable for determining if the fusion protein has been incorporated into the inclusions include, but are not limited to, the detection thereof by indirect immunofluorescence using polyclonal antibodies against the polypeptide of interest comprised in the fusion protein.

The result of the first step (i) of the second fusion protein purification method of the invention will be the formation of complexes between the fusion protein and the preformed inclusions through one of the regions described above having affinity for the inclusions.

In a second step (ii), the second fusion protein purification method comprises purifying the complex formed between the inclusions and the fusion protein of step (i). In particular, if the fusion protein came from a crude cell extract in which said protein had been expressed, this step allows separating the aggregates from the other components present in the cell extract (polypeptides, nucleic acids, cell wall residues, etc.). Methods suitable for separating the aggregates from the other components present in the sample include, without limitation, differential centrifugation, sedimentation, filtration, density gradient separation and the like.

The person skilled in the art will see that the second step (ii) of the second fusion protein purification method of the invention is the same as the third step (iii) of the first fusion protein purification method of the invention described in detail above. Therefore, the definitions and particular embodiments of the third step (iii) of the first fusion protein purification method of the invention are included herein by reference.

Once a preparation consisting of complexes formed by the inclusions and the fusion protein is available, the fusion protein can be separated from the inclusions. Therefore, in another particular embodiment the first fusion protein purification method of the invention further comprises separating the fusion protein from the inclusions.

Methods for separating the fusion protein from the inclusions have been described in detail in the context of the second fusion protein purification method and are included herein by reference.

In a particular embodiment, the polypeptide of interest and the third component comprised in the fusion protein are connected by a peptide the sequence of which contains a cleavage target for a protease. This embodiment allows incubating the purified inclusions with a protease specific for said target sequence. The protease cleavage sites suitable for incorporation in the polypeptides of the invention include enterokinase (SEQ ID NO: 17), factor Xa (SEQ ID NO: 18), thrombin (SEQ ID NO: 19), TEV protease (SEQ ID NO: 20), PreScission protease (SEQ ID NO: 21), inteins and the like. A person skilled in the art would know the specific cleavage conditions of each of the proteases.

The result is the cleavage of the polypeptide of interest from the fusion protein incorporated in the inclusion. Finally, the polypeptide of interest can be purified by techniques suitable for purification which depend on the nature of the polypeptide of interest and will be known by the person skilled in the art. Polypeptide purification techniques are widely known in the art and include, without limitation, affinity chromatography, exclusion chromatography, ion exchange chromatography, adsorption chromatography, immunoprecipitation, etc.

In another particular embodiment, the first polynucleotide of the invention encodes a polypeptide further comprising a peptide for facilitating purification located in the C-terminal position with respect to the first component. The term "peptide for facilitating purification" has been defined in detail in the context of the first polynucleotide of the invention and the definition and particular embodiments thereof are included herein by reference.

In order to make use of the unexpected greater inclusion-forming efficiency of the minimum region of an Orthoreovirus muNS protein when it lacks N-glycosylations, the use of a polynucleotide encoding a polypeptide the second component of which lacks or does not contain N-glycosylations is particularly advantageous for the inclusion purification method of the invention.

Therefore, in another particular embodiment the second component lacks N-glycosylation consensus sequences. The term "N-glycosylation consensus sequence" has been defined in detail in the context of the first polynucleotide of the invention and the definition and particular embodiments thereof are included herein by reference.

3. Third Fusion Protein Purification Method of the Invention

In another aspect, the invention relates to a method for purifying a fusion protein comprising (a) a polypeptide of interest, and
(b) the minimum region of an Orthoreovirus muNS protein having the capacity to incorporate itself into inclusions formed by a protein comprising the minimum region of an Orthoreovirus muNS having the capacity to form inclusions when expressed in a cell,
from a composition containing said fusion protein, hereinafter "third fusion protein purification method of the invention," wherein said method comprises:
(i) contacting said composition with a polypeptide comprising the minimum region of an Orthoreovirus muNS protein having the capacity to form inclusions when expressed in a cell and lacking N-glycosylation consensus sequences with said composition; wherein said polypeptide with inclusion-forming capacity is in a soluble form, and
wherein said contacting is performed in the presence of a divalent cation concentration suitable for forming inclusions from the polypeptide with inclusion-forming capacity and from the recruitment of the fusion protein into said inclusions,
(ii) purifying the complex formed between the inclusions and the fusion protein of step (i).

The terms "fusion protein," "polypeptide of interest," "minimum region of an Orthoreovirus muNS protein having the capacity to incorporate itself into inclusions formed by a protein comprising the minimum region of an Orthoreovirus muNS having the capacity to form inclusions when expressed in a cell," "inclusion," "cell," "composition containing said fusion protein," "polypeptide," "minimum region of an Orthoreovirus muNS protein having the capacity to form inclusions when expressed in a cell" and "divalent cation" have been described in detail in the context of the first polynucleotide of the invention and the definitions and particular embodiments thereof similarly apply here.

In a first step (i), the third fusion protein purification method of the invention comprises contacting a composition containing said fusion protein with a polypeptide comprising the minimum region of an Orthoreovirus muNS protein having the capacity to form inclusions when expressed in a cell and lacking N-glycosylation consensus sequences with said composition; wherein said polypeptide with inclusion-forming capacity is in a soluble form, and wherein said contacting is performed in the presence of a divalent cation concentration suitable for forming inclusions from the polypeptide with inclusion-forming capacity and from the recruitment of the fusion protein into said inclusions. In other words, the first polypeptide of the invention lacking N-glycosylation consensus sequences is used in the first step (i) under conditions suitable for the recruitment of the fusion protein into said inclusions. The first polynucleotide of the invention lacking N-glycosylation consensus sequences under conditions suitable for the recruitment of the fusion protein into said inclusions has been described in detail above and the definitions and particular embodiments thereof also apply to the second fusion protein purification method of the invention. The fusion protein of the invention is also used in step (i). The fusion protein of the invention has been described in detail above and the definitions and particular embodiments thereof also apply to the second fusion protein purification method of the invention.

To carry out step (i) of the third method of the invention, the polypeptide comprising the minimum region of an Orthoreovirus muNS protein having the capacity to form inclusions when expressed in a cell and lacking N-glycosylation consensus sequences with said composition; wherein said polypeptide with inclusion-forming capacity is in a soluble form, or in other words, polypeptide comprising the minimum region of an Orthoreovirus muNS protein having the capacity to form inclusions when expressed in a cell and lacking N-glycosylation consensus sequences with said composition; wherein said polypeptide with inclusion-forming capacity does not form inclusions.

The contacting of step (i) is performed in the presence of a divalent cation concentration suitable for forming inclusions from the polypeptide with inclusion-forming capacity and from the recruitment of the fusion protein into said inclusions.

Preferably, the polypeptide comprising the minimum region of an Orthoreovirus muNS protein having the capacity to form inclusions when expressed in a cell and lacking N-glycosylation consensus sequences with said solubilized composition is prepared from aggregates formed by the expression of the polypeptide comprising the minimum region of an Orthoreovirus muNS protein having the capacity to form inclusions when expressed in a cell and lacking N-glycosylation consensus sequences with said composition or from fragments of the polypeptide comprising the minimum region of an Orthoreovirus muNS protein having the capacity to form inclusions when expressed in a cell and lacking N-glycosylation consensus sequences with said composition or from inclusions, followed by solubilization thereof in a medium in the absence of divalent cations.

In an even more preferred embodiment, the fusion protein is in a buffer containing divalent cations at a concentration in excess with respect to the concentration suitable for the formation of aggregates of the polypeptide comprising the minimum region of an Orthoreovirus muNS protein having the capacity to form inclusions when expressed in a cell and lacking N-glycosylation consensus sequences with said composition, such that upon mixing the muNS preparation with the mixture containing the fusion protein suitable concentrations are reached in the sample of divalent cations so as to allow the muNS protein to form aggregates or inclusions incorporating the fusion protein. Therefore, if the optimum divalent cation concentration is 5 mM, the mixture containing the fusion protein can contain up to 10 mM of said cations, such that upon combining a volume of the solution containing the soluble muNS protein and a volume of the mixture containing the fusion protein in the absence of divalent cations, a final concentration of 5 mM, which is suitable for the formation of aggregates of the muNS protein, is obtained. The skilled person can calculate the divalent cation concentration required in the mixture containing the fusion protein such that, upon combining it with the composition comprising the muNS protein or the variant thereof, final divalent cation concentrations for the inclusions to be formed are reached.

Step (i) is carried out for the time required for the formation of complexes to take place from the polypeptide comprising the minimum region of an Orthoreovirus muNS protein having the capacity to form inclusions when expressed in a cell and lacking N-glycosylation consensus sequences and from the fusion protein. This can be determined, for example, by means of conventional techniques for determining if a protein is in a soluble form at a specific concentration, such as turbidimetric methods, such as nephelometry, filtration and the like.

In a second step (i), the second method of the invention comprises (ii) purifying the complex formed between the inclusions and the fusion protein of step (i). In particular, if the fusion protein came from a crude cell extract in which said protein had been expressed, this step allows separating the aggregates from the other components present in the cell extract (polypeptides, nucleic acids, cell wall residues, etc.). Methods suitable for separating the aggregates from the other components present in the sample include, without limitation, differential centrifugation, sedimentation, filtration, density gradient separation and the like.

Once a preparation consisting of complexes formed by the inclusions and the fusion protein is available, the fusion protein can be separated from the inclusions. Therefore, in another particular embodiment the first fusion protein purification method of the invention further comprises separating the fusion protein from the inclusions.

Methods for separating the fusion protein from the inclusions have been described in detail in the context of the second fusion protein purification method and are included herein by reference.

In a particular embodiment, the polypeptide of interest and the third component comprised in the fusion protein are connected by a peptide the sequence of which contains a cleavage target for a protease. This embodiment allows incubating the purified inclusions with a protease specific for said target sequence. The protease cleavage sites suitable for incorporation in the polypeptides of the invention include enterokinase (SEQ ID NO: 17), factor Xa (SEQ ID NO: 18), thrombin (SEQ ID NO: 19), TEV protease (SEQ ID NO: 20), PreScission protease (SEQ ID NO: 35), inteins and the like. A person skilled in the art would know the specific cleavage conditions of each of the proteases.

The result is the cleavage of the polypeptide of interest from the fusion protein incorporated in the inclusion. Finally, the polypeptide of interest can be purified by techniques suitable for purification which depend on the nature of the polypeptide of interest and will be known by the person skilled in the art. Polypeptide purification techniques are widely known in the art and include, without limitation, affinity chromatography, exclusion chromatography, ion exchange chromatography, adsorption chromatography, immunoprecipitation, etc.

In another particular embodiment, the first polynucleotide of the invention encodes a polypeptide further comprising a peptide for facilitating purification located in the C-terminal position with respect to the first component. The term "peptide for facilitating purification" has been defined in detail in the context of the first polynucleotide of the invention and the definition and particular embodiments thereof are included herein by reference.

Methods for Identifying Protein-Protein Interactions

The possibility of expressing the proteins of interest in inclusions formed by muNS-Mi and directing the proteins of interest to the inclusions formed by muNS-Mi in the ER has several potential applications in addition to protein purification. One of them is to identify post-translationally modified protein interactions in the ER. Therefore, if a polypeptide of interest is tagged with one of the domains described above for directing it to the inclusion bodies, this polypeptide of interest may attract other polypeptides interacting strongly with it in the ER and relocating them in the inclusions.

Therefore, in another aspect the invention relates to a method for detecting interaction between a first polypeptide and a second polypeptide, hereinafter "first method for detecting interactions of the invention," comprising:

(i) expressing in a cell a polynucleotide encoding a polypeptide comprising (a) a first component comprising a secretory pathway signal peptide, and (b) a second component comprising the minimum region of an Orthoreovirus muNS protein having the capacity to form inclusions when expressed in a cell or a functionally equivalent variant thereof, wherein the first component is located in the N-terminal position with respect to the second component, and wherein the polypeptide further comprises a polypeptide of interest located in the C-terminal position with respect to the first component, and wherein the polypeptide of interest is the first polypeptide, and keeping said cell under conditions suitable for forming inclusions;

(ii) expressing in said cell a polynucleotide encoding a fusion protein comprising a secretory pathway signal peptide and the second polypeptide, wherein the signal peptide is located in the N-terminal position with respect to the second polypeptide, and keeping said cell under conditions suitable for said second polypeptide to be expressed; and (iii) determining if the second polypeptide is associated with the complex formed by the inclusions generated in step (i), wherein if the second polypeptide is detected it is indicative of the interaction between the first and second polypeptides, wherein steps (i) and (ii) are carried out in any order.

As the person skilled in the art will see, step (i) of the first method for detecting interactions of the invention uses the first polynucleotide of the invention. The first polynucleotide of the invention has been described in detail above and the definitions and particular embodiments thereof also apply to the first method for detecting interactions of the invention.

The first step (i) of the first method for detecting interactions of the invention coincides with the first step (i) of the purification method of the invention, so reference is made herein to said step.

Once the inclusions comprising the polypeptide of interest or first polypeptide have been expressed, the second polynucleotide encoding a fusion protein comprising a secretory pathway signal peptide and the second polypeptide, wherein the signal peptide is located in the N-terminal position with respect to the second polypeptide, is expressed in said cell. The term "secretory pathway signal peptide" has been described in detail in the context of the first polynucleotide of the invention and the definitions and particular embodiments thereof are included herein by reference.

Likewise, the order of steps (i) and (ii) can vary, such that the second polynucleotide is expressed first instead of the inclusions. The expression of the second polynucleotide encoding a fusion protein comprising a secretory pathway signal peptide and the second polypeptide, wherein the signal peptide is located in the N-terminal position with respect to the second polypeptide, will be carried out in a manner similar to the first polypeptide, such that reference is made to the first step (i) of the purification method of the invention.

The last step of the first method for detecting interactions of the invention consists of determining if the second polypeptide is associated with the first polypeptide comprised in the inclusions generated in step (i), wherein if the second polypeptide is detected, it is indicative of there being an interaction between the first and second polypeptides.

Methods for detecting the interaction between two polypeptides are known by the person skilled in the art, and include, without limitation electrophoresis under native conditions, size exclusion chromatography under conditions suitable for detecting the interaction, gradient centrifugation, immunoprecipitation, etc. In a preferred embodiment, the detection of the association between the first and second polypeptides is carried out by means of detection by means of immunofluorescence or fluorescence microscopy.

Said method for detecting polypeptide interaction can include detecting the interaction of more than two polypeptides. Therefore, the assembly of supramolecular complexes in cells for structural study could be favored by means of the system of interaction through the inclusions. Many molecular complexes formed by several proteins are difficult to obtain by means of the conventional protein expression systems. The possible dispersion of their individual components in the cell can possibly make the formation of said complexes difficult. Virions of reoviruses are supramolecular complexes that naturally assemble themselves in an extremely efficient manner in the infected cell. To increase said efficiency, virion components are recruited into the muNS inclusions in an ordered and selective manner. So, by concentrating in the same compartment, they increase the possibilities of finding suitable ligands. The present method for detecting polypeptide interaction allows simulating reovirus morphogenesis, but with exogenous proteins which can be selectively directed to the muNS or muNS-Mi inclusions in the ER. To that end, said polypeptides can be tagged with one of the aforementioned domains and several proteins can be directed to the inclusions in a simple manner and their possibilities of finding suitable ligands for the assembly of complexes can thereby be increased.

In another aspect, the invention relates to a method for detecting interaction between a first polypeptide and a second polypeptide, hereinafter "second method for detecting interactions of the invention," comprising:

(i) expressing in a cell a first polynucleotide, wherein said first polynucleotide encodes a polypeptide comprising (a) a first component comprising a secretory pathway signal peptide, and (b) a second component comprising the minimum region of an Orthoreovirus muNS protein having the capacity to form inclusions when expressed in a cell or a functionally equivalent variant thereof, wherein the first component is located in the N-terminal position with respect to the second component, and keeping said cell under conditions suitable for forming inclusions;

(ii) expressing in said cell a second polynucleotide encoding a fusion protein comprising:

(a) a first component comprising a secretory pathway signal peptide, (b) a second component comprising said first polypeptide, and (c) a third component comprising the minimum region of an Orthoreovirus muNS protein having the capacity to incorporate itself into inclusions formed by a protein comprising the minimum region of an Orthoreovirus muNS having the capacity to form inclusions when expressed in a cell, wherein the first component is located in the N-terminal position with respect to the second and third components, under conditions suitable for the fusion protein to be directed to the inclusions formed in step (i);

(iii) expressing in said cell a third polynucleotide encoding a fusion protein comprising a secretory pathway signal peptide and the second polypeptide, wherein the signal peptide is located in the N-terminal position with respect to the second polypeptide, and keeping said cell under conditions suitable for said second polypeptide to be expressed; and (iv) determining if the second polypeptide is associated with the complex formed by the inclusions generated in step (i) and the fusion protein expressed in step (ii), wherein if the second polypeptide is detected it is indicative of the interaction between said first and second polypeptides, wherein steps (i), (ii) and (iii) are carried out in any order.

As the person skilled in the art will see, step (i) of the second method for detecting interactions of the invention uses the first polynucleotide of the invention, and step (ii) of the second method for detecting interactions of the invention uses the second polynucleotide of the invention. The first and the second polynucleotides of the invention have been described in detail above and the definitions and particular embodiments thereof also apply to the first method for detecting interactions of the invention.

The first two steps (i) and (ii) of the second method for detecting interactions of the invention coincide with the first two steps of the first fusion protein purification method of the invention, so reference is made herein to said steps.

The expression of the third polynucleotide encoding a fusion protein comprising a secretory pathway signal peptide and the second polypeptide, wherein the signal peptide is located in the N-terminal position with respect to the second polypeptide, will be carried out in a manner similar to the first and second polynucleotides, such that reference is made to the first step (i) of the purification method of the invention.

The last step of the second method for detecting interactions of the invention consists of determining if the second polypeptide is associated with the first polypeptide comprised in the inclusions generated in step (i), wherein if the second polypeptide is detected, it is indicative of there being an interaction between the first and second polypeptides. The last step of the second method for detecting interactions of the invention coincides with the last step of the first method for detecting interactions of the invention, so reference is made herein to said step.

Alternatively, given that it is possible for the inclusions formed by the muNS protein or by the minimum region of said protein to assemble and disassemble at will depending on the presence or absence of divalent cations in the mixture, the invention contemplates a third method for detecting interaction between a first polypeptide and a second polypeptide, hereinafter "third method for detecting interactions of the invention," wherein said method comprises,
(i) contacting, with the second polypeptide, the inclusions formed by a fusion protein comprising the minimum region of an Orthoreovirus muNS protein having the capacity to form inclusions when expressed in a cell and lacking N-glycosylation consensus sequences and the first polypeptide, and
(ii) detecting the association of the second polypeptide with the inclusions, wherein detection of the second polypeptide in the inclusions is indicative of the interaction between the first polypeptide and the second polypeptide.

In another aspect, the invention relates to a method for detecting interaction between a first polypeptide and a second polypeptide, hereinafter "fourth method for detecting interactions of the invention," comprising
(i) contacting
(a) inclusions formed by a fusion protein comprising the minimum region of an Orthoreovirus muNS protein having the capacity to form inclusions when expressed in a cell and lacking N-glycosylation consensus sequences,
(b) a fusion protein comprising the minimum region of an Orthoreovirus muNS protein having the capacity to incorporate itself into inclusions formed by a protein comprising the minimum region of an Orthoreovirus muNS having the capacity to form inclusions when expressed in a cell and the first polypeptide, and
(c) the second polypeptide; and
(ii) detecting the association of the second polypeptide with the inclusions,
wherein detection of the second polypeptide in the inclusions is indicative of the interaction between the first polypeptide and the second polypeptide.

The terms "polypeptide," "inclusion," "fusion protein," "minimum region of an Orthoreovirus muNS protein having the capacity to form inclusions when expressed in a cell and lacking N-glycosylation consensus sequences" and "minimum region of an Orthoreovirus muNS protein having the capacity to incorporate itself into inclusions formed by a protein comprising the minimum region of an Orthoreovirus muNS having the capacity to form inclusions when expressed in a cell and the first polypeptide" have been described in detail above and the definitions and particular embodiments thereof are included in the context of the third and fourth methods for detecting interactions of the invention by reference.

The last step of the third and fourth methods for detecting interactions of the invention consists of determining if the second polypeptide is associated with the first polypeptide comprised in the inclusions formed in step (i), wherein if the second polypeptide is detected, it is indicative of there being an interaction between the first and second polypeptides. The last step of the second method for detecting interactions of the invention coincides with the last step of the first method for detecting interactions of the invention, so reference is made herein to said step.

In Vitro Uses of the First and Second Polynucleotides of the Invention

In another aspect, the invention relates to the use, hereinafter in vitro use of the invention, of a polynucleotide encoding a fusion protein comprising:
(a) a first component comprising a secretory pathway signal peptide,
(b) a second component comprising said first polypeptide, and
(c) a third component comprising the minimum region of an Orthoreovirus muNS protein having the capacity to incorporate itself into inclusions formed by a protein comprising the minimum region of an Orthoreovirus muNS having the capacity to form inclusions when expressed in a cell,
wherein the first component is located in the N-terminal position with respect to the second and third components for incorporating the second component of the polypeptide encoded by said polynucleotide into the inclusions resulting from the expression of the polynucleotide in a cell encoding a polypeptide comprising
(a) a first component comprising a secretory pathway signal peptide, and
(b) a second component comprising the minimum region of an Orthoreovirus muNS protein having the capacity to form inclusions when expressed in a cell or a functionally equivalent variant thereof,
wherein the first component is located in the N-terminal position with respect to the second component.

As the person skilled in the art will see, the in vitro use of the first and second polynucleotides of the invention uses the first polynucleotide of the invention, and step (ii) of the second method for detecting interactions of the invention uses the second polynucleotide of the invention. The first and the second polynucleotides of the invention have been described in detail above and the definitions and particular embodiments thereof also apply here.

Therapeutic Uses of the First and Second Polynucleotides of the Invention

In another aspect, the invention relates to a polynucleotide encoding a polypeptide comprising
(a) a first component comprising a secretory pathway signal peptide, and
(b) a second component comprising the minimum region of an Orthoreovirus muNS protein having the capacity to form inclusions when expressed in a cell or a functionally equivalent variant thereof, and
(c) a third component comprising a polypeptide of interest wherein the first component is located in the N-terminal position with respect to the second and third components, for use thereof in medicine, hereinafter "first therapeutic use of the invention."

As the person skilled in the art will see, the first therapeutic use of the invention uses the first polynucleotide of the invention. The first polynucleotide of the invention has been described in detail above and the definitions and particular embodiments thereof also apply here.

In another aspect, the invention relates to a polynucleotide encoding a fusion protein comprising:
(a) a first component comprising a secretory pathway signal peptide,
(b) a second component comprising a polypeptide of interest, and
(c) a third component comprising the minimum region of an Orthoreovirus muNS protein having the capacity to incorporate itself into inclusions formed by a protein comprising the minimum region of an Orthoreovirus muNS having the capacity to form inclusions when expressed in a cell,
wherein the first component is located in the N-terminal position with respect to the second and third components, for use thereof in medicine, hereinafter "second therapeutic use of the invention."

As the person skilled in the art will see, the second therapeutic use of the invention uses the second polynucleotide of the invention. The second polynucleotide of the invention has been described in detail above and the definitions and particular embodiments thereof also apply here.

In another aspect, the invention relates to the use of a polynucleotide encoding a polypeptide comprising
(a) a first component comprising a secretory pathway signal peptide, and
(b) a second component comprising the minimum region of an Orthoreovirus muNS protein having the capacity to form inclusions when expressed in a cell or a functionally equivalent variant thereof, and
(c) a third component comprising a polypeptide of interest wherein the first component is located in the N-terminal position with respect to the second component and third component,
for preparing a medicinal product for the treatment of a disease in which the expression of the polypeptide of interest is required, hereinafter "third therapeutic use of the invention."

As the person skilled in the art will see, the third therapeutic use of the invention uses the first polynucleotide of the invention. The first polynucleotide of the invention has been described in detail above and the definitions and particular embodiments thereof also apply here.

In another aspect, the invention relates to the use of a polynucleotide encoding a fusion protein comprising:
(a) a first component comprising a secretory pathway signal peptide,
(b) a second component comprising a polypeptide of interest, and
(c) a third component comprising the minimum region of an Orthoreovirus muNS protein having the capacity to incorporate itself into inclusions formed by a protein comprising the minimum region of an Orthoreovirus muNS having the capacity to form inclusions when expressed in a cell,
wherein the first component is located in the N-terminal position with respect to the second and third components, for preparing a medicinal product for the treatment of a disease in which the expression of the polypeptide of interest is required, hereinafter "fourth therapeutic use of the invention."

As the person skilled in the art will see, the fourth therapeutic use of the invention uses the second polynucleotide of the invention. The second polynucleotide of the invention has been described in detail above and the definitions and particular embodiments thereof also apply here.

As it is used herein, the term "disease in which the expression of the polypeptide of interest is required" refers to diseases in which the expression of the fusion protein can eliminate or reduce the symptoms of the disease. Preferably, the disease is a disease requiring the generation of an immune response against the polypeptide of interest and includes diseases such as diseases caused by viral infections if the polypeptide of interest is a viral antigen, diseases caused by bacterial infections if the polypeptide of interest is a bacterial antigen, diseases caused by fungal infections if the polypeptide of interest is a fungal antigen, allergies if the polypeptide of interest is an allergen, diseases caused by a parasitic infestation if the polypeptide of interest is a parasitic antigen and/or a tumor if the polypeptide of interest is a tumor cell-specific antigen.

Diseases caused by viral infections which can be treated with the fusion protein include, without limitation, diseases caused by the infections by HIV-1 virus (AIDS), human herpesvirus such as herpes simplex virus (herpes simplex, genital herpes), cytomegalovirus (mononucleosis, retinitis, hepatitis), Epstein Barr virus (infectious mononucleosis, Burkitt's lymphoma and nasopharyngeal carcinoma) and varicella zoster virus (chicken pox, herpes zoster); hepatitis virus infection such as hepatitis B virus or hepatitis C virus, paramyxovirus such as respiratory syncytial virus, parainfluenza virus, rubella virus, measles virus, mumps virus, human papillomavirus; flavivirus such as yellow fever virus, dengue virus, tick-borne encephalitis virus or the Japanese encephalitis virus and rotavirus. Another type of viral infections which can be treated are described in detail in Fundamental Virology, second edition, eds. Fields, B. N. and Knipe, D. M. (Raven Press, New York, 1991).

Diseases caused by bacterial infections which can be treated with the fusion protein include, without limitation, diseases caused by microorganisms of the genus *Escherichia, Enterobacter, Salmonella, Staphylococcus, Shigella, Listeria, Aerobacter, Helicobacter, Klebsiella, Proteus, Pseudomonas, Streptococcus, Chlamydia, Mycoplasma, Pneumococcus, Neisseria, Clostridium, Bacillus, Corynebacterium, Mycobacterium, Campylobacter, Vibrio, Serratia, Providencia, Chromobacterium, Brucella, Yersinia, Haemophilus* or *Bordetella*.

Diseases caused by fungal infections which can be treated with the fusion protein include, without limitation, candidiasis, aspergillosis, histoplasmosis, cryptococcal meningitis and the like.

Parasitic infestations which can be treated with the fusion protein include, without limitation, malaria, *Pneumocystis jirovecii* infection, pneumonia, sleeping sickness, leishmaniasis, cryptosporidiosis, toxoplasmosis and *trypanosoma*.

Allergic disorders which can be treated with the fusion protein include, without limitation, allergies caused by exposure to pollen (pollen allergens from trees, herb plant, weed and grass), allergies caused by exposure to allergens in insects (inhalable allergens, allergens in saliva and venom), to allergens from the dander and hair of animals and to allergens in food.

The fusion protein is also suitable for the treatment of hyperproliferative diseases. As it is used herein, the expression "proliferative disease" refers to diseases which are caused by or result from inappropriately high levels of cell division, inappropriately low levels of apoptosis or both and includes both primary tumors and metastases. The term "primary tumor" refers to a tumor located in the primary site in which said tumor originated. As it is used herein, the term "metastasis" refers to the process through which a tumor spreads to body tissues different than the primary site of tumor origin.

In the context of the invention, "treatment of a hyperproliferative disease" or "treatment of a tumor" is understood as the administration of the fusion protein for preventing or delaying the onset of symptoms, complications or biochemical indications of the cancer or tumor, for alleviating its symptoms or for stopping or inhibiting its development and progress such as the onset of metastasis, for example. The treatment can be a prophylactic treatment for delaying the onset of the disease or for preventing the manifestation of its clinical or subclinical symptoms or a therapeutic treatment for eliminating or alleviating the symptoms after the manifestation of the disease or in relation to its surgical or radiotherapy treatment.

The following examples serve to illustrate the invention and must not be considered as limiting of the scope of the invention.

EXAMPLES

Materials and Methods
Solutions and Buffers

Dapi: prepared at 100 µg/ml in sterile water and sterilized through a 0.22 µm filter.

Mounting medium: 6 g of glycerol; 2.4 g of Mowiol; 6 ml of $H_2O$ and 12 ml of 0.2 M Tris-HCl (pH 8.5).

PBS-BSA: 137 mM NaCl; 2.7 mM KCl; 8 mM $Na_2PO_4$; 1.2 mM $KH_2PO_4$ and 2% BSA.

PBS-Paraformaldehyde: 137 mM NaCl; 2.7 mM KCl; 8 mM $Na_2PO_4$; 1.2 mM $KH_2PO_4$ and 4% depolymerized paraformaldehyde PBS: 137 mM NaCl; 2.7 mM KCl; 8 mM $Na_2PO_4$; 1.2 mM $KH_2PO_4$ PBST-Milk: 137 mM NaCl; 2.7 mM KCl; 8 mM $Na_2PO_4$; 1.2 mM $KH_2PO_4$; 0.05% Tween-20 and 5% skimmed milk Electrophoresis buffer for 1×SDS-PAGE (Tris-glycine-SDS): 25 mM Tris-HCl (pH 8.3); 192 mM glycine and 0.1% SDS.

Laemmli sample buffer: 60 mM Tris-HCl (pH 6.8), 2% SDS, 10% glycerol, 5% β-mercaptoethanol and 0.024% bromophenol blue.

Transfer buffer: 25 mM Tris-HCl (pH 8.3); 192 mM glycine and 20% methanol.

Plasmids

The plasmids pCINeo-M3 (448-635), pCDNA 3.1/Zeo-muNS(477-542) and pGEFP-C1-M3(477-542) were obtained as described in patent document WO 2011/098652.
Constructing the pcDNA-secmuNS-Mi Plasmid For constructing this plasmid, the sequence corresponding to muNS-Mi was amplified from the template pCINeo-M3 (448-635) using the primers:

```
Forward
                            (SEQ ID NO: 27)
5'-TTGGCGCGCAAATGCCAGCCGTACTGCTGTC-3'

Reverse
                            (SEQ ID NO: 28)
5'-TTGCGGCCGCAATCACAGATCATCCACC-3'.
```

The amplified sequence was introduced in the pcDNA 3 expression plasmid in the C-terminal position after the endoplasmic reticulum-entry sequence (signal peptide) that already contained the plasmid.
Constructing the pcDNA-secmuNS-Mi* Plasmid For constructing same, the pcDNA-secmuNS-Mi plasmid was used and mutagenesis was caused using the following oligonucleotides:

```
                            (SEQ ID NO: 29)
5'-GGGCCTGCTCGCTCGTTGTAGCGTATCTGGTGATTCAATCTCC-3'

(SEQ ID NO: 30)
5'-GGAGATTGAATCACCAGATACGCTACAACGAGCGAGCAGGCCC-3'
```

A mutation is thereby introduced in position 57 of muNS-Mi or position 504 of muNS, changing Asn for Ser (N57S or N504S) and eliminating the glycosylation target.

The mutagenesis was performed following the protocol of the kit used: QuikChange Site-Directed Mutagenesis Kit (Qiagen)
Constructing the pGEFP-IC* Plasmid For constructing this plasmid, the pGEFP-C1-M3(477-542) plasmid was used and mutagenesis was caused using the following oligonucleotides;

```
                            (SEQ ID NO: 29)
5'-GGGCCTGCTCGCTCGTTGTAGCGTATCTGGTGATTCAATCTCC-3'

(SEQ ID NO: 30)
5'-GGAGATTGAATCACCAGATACGCTACAACGAGCGAGCAGGCCC-3'
```

A mutation is thereby introduced in position 57 of muNS-Mi or position 504 of muNS changing Asn for Ser (N57S or N504S) and eliminating the glycosylation target.

The mutagenesis was performed following the protocol of the kit used: QuikChange Site-Directed Mutagenesis Kit (Qiagen)
Constructing the pcDNA-VSVg-SV5-IC* Plasmid The ectodomain located at the N-terminal end of glycoprotein G of the lipid envelope of vesicular stomatitis virus (VSV) having its own signal peptide was obtained from the RNA of the VSV by means of a RT-PCR using the following primers:

```
Forward_VSV:
                            (SEQ ID NO: 31)
5'-CGGCTAGCATGAAGTGCCTTTTGTACTTAGC-3'

Reverse_VSV:
                            (SEQ ID NO: 32)
5'-CCCAAGCTTGGGAGAGCTCTTCCAACTACTGAAC-3'.
```

The amplified sequence was introduced in the pcDNA3.1 Zeo+ expression plasmid, obtaining the pcDNA-VSVg plasmid as a result. To enable detecting the protein by immunofluorescence and by Western blot, the SV5 epitope was added to the C-terminal end of VSV truncated glycoprotein G. To that end, an adaptor was generated, hybridizing the following oligonucleotides:

(SEQ ID NO: 33)
5'-GCCGGAATTCCGAAGGCAAACCAATCCCAAACCCACTGCTGGGCCTGGAT
TTGCGGCCGCAAAT-3'

(SEQ ID NO: 34)
5'-ATTTGCGGCCGCAAATCCAGGCCCAGCAGTGGGTTTGGGATTGGTTTGCC
TTCGGAATTCCGGC-3'

After digesting the adaptor with EcoRI and NotI, it was inserted in the pcDNA-VSVg plasmid previously digested with the same enzymes for generating the pcDNA-VSVg-SV5 plasmid.

The IC* domain (with mutation N28S corresponding to mutation N504 of the complete muNS protein sequence) was obtained by means of PCR using pcDNAmuNS-Mi* (containing mutation N504S) as template and the following primers:

Forward IC:
(SEQ ID NO: 36)
5'-TTGCGGCCGCAAGAAGATCACTTGTTGGCTTATC-3'

Reverse IC:
(SEQ ID NO: 37)
5'-GCGTCTAGATTACGCTTCCACACGGGGTTC-3'

The IC* sequence was introduced in the C-terminal position of the SV5 domain in the pcDNA-VSVg-SV5 plasmid, generating the pcDNA-VSVg-SV5-IC* plasmid.

Transfection

For transfection, cells were grown in monolayer in a 12-well multiwell. A D-MEM stock medium was used in which the plasmid was incubated with lipofectamine for 15 minutes. This mixture was added to the cells adhered on the multiwell with D-MEM stock and incubated from 3 to 5 hours at 37° C., after which the medium was removed and D-MEM medium supplemented with FBS, antibiotics and glutamine was added.

Immunofluorescence

DF-1 cells were transfected with the plasmids directing the expression of the proteins to the ER. After 24 hours of incubation, the cells were fixed with 4% paraformaldehyde in PBS for 30 minutes, after which they were washed 3 times with PBS and blocked for 1 hour with 2% bovine serum albumin (BSA) in PBS. After permeabilizing with 0.5% TritonX-100 in PBS, they were incubated for 1 hour with anti-muNS protein primary antibodies. After washing 3 times with PBS, they were incubated with secondary antibody (Alexa Fluor® 594 Goat Anti-Rabbit IgG Sigma #A11012#) for 1 h, mounted with Mowiol and observed under an Olympus BX51 fluorescence microscope. The images were obtained with a DP-71 digital camera.

In the case of VSV-IC*, after 24 hours of incubation the cells were fixed with methanol at −20° C. for 15 minutes, after which they were washed 3 times with PBS and blocked for 30 minutes with 2% bovine serum albumin (BSA) in PBS. They were then incubated with (rabbit) anti-muNS protein primary antibodies and (mouse) anti-SV5 epitope primary antibodies for 1 hour. After washing 3 times with PBS, they were incubated with Alexa Fluor 594 (goat anti-mouse) secondary antibodies and Alexa Fluor 488 (goat anti-rabbit) secondary antibodies for 30 minutes and mounted with Mowiol for subsequently being observed under an Olympus BX51 fluorescence microscope. The images were obtained with a DP-71 digital camera.

Post-Translational Modification Analysis

DF-1 cells were transfected with the plasmids directing the expression of the proteins to the ER. After 24 hours of incubation, the cells were lysed in RIPA* buffer (50 mM of TrisHCl (pH 8.0), 150 mM of NaCl, 0.2% SDS, protease inhibitor) and incubated with N-glycosidase for 1 hour at 37° C. The cell extracts were then analyzed by SDS-PAGE and Western blot using antibodies obtained against the viral muNS protein. Peroxidase-conjugated anti-Rabbit IgGs (Sigma #A0545#) were used as secondary antibody.

Mutagenesis

The mutagenesis was carried out using the QuikChange Site-Directed Mutagenesis Kit (QIAGEN), following the manufacturer's instructions.

Example 1: Formation of muNS-Mi Inclusions in the Endoplasmic Reticulum (ER)

To express muNS-Mi in the endoplasmic reticulum (ER), a signal sequence was added to the amino terminal end of the sequence encoding for muNS-Mi. To that end, the following endoplasmic reticulum-entry signal sequence was used: MGWSLILLFLVAVATGVHSQ (SEQ ID NO: 1). The resulting plasmid was called pcDNA-secmuNS-Mi and it directs the expression of a fusion between the signal sequence and muNS-Mi, which will theoretically cause the con-translational introduction thereof in the ER.

To check if the generated fusion protein was capable of forming inclusions or microspheres in the ER, DF-1 cells were transfected with the pcDNA-secmuNS-Mi plasmid, allowing the protein to be expressed for 24 hours, after which the cells were fixed and the presence of muNS-Mi was detected by immunofluorescence using anti-muNS protein antibodies. In parallel, cells were transfected with pcDNA 3.1/Zeo-muNS(477-542), encoding muNS-Mi, in order to compare the expression of the two versions of the viral protein.

It was confirmed that the protein with the signal sequence produced microspheres in the transfected cells, although they were rather smaller than those produced by the cytosolic protein (FIG. 1). However, microsphere formation efficiency in the ER is lower than in the cytosol: while virtually all the detected cytosolic protein was found to form microspheres (FIG. 1, image 1), less than 50% of the cells expressing the protein in the ER formed microspheres.

Figure 2:
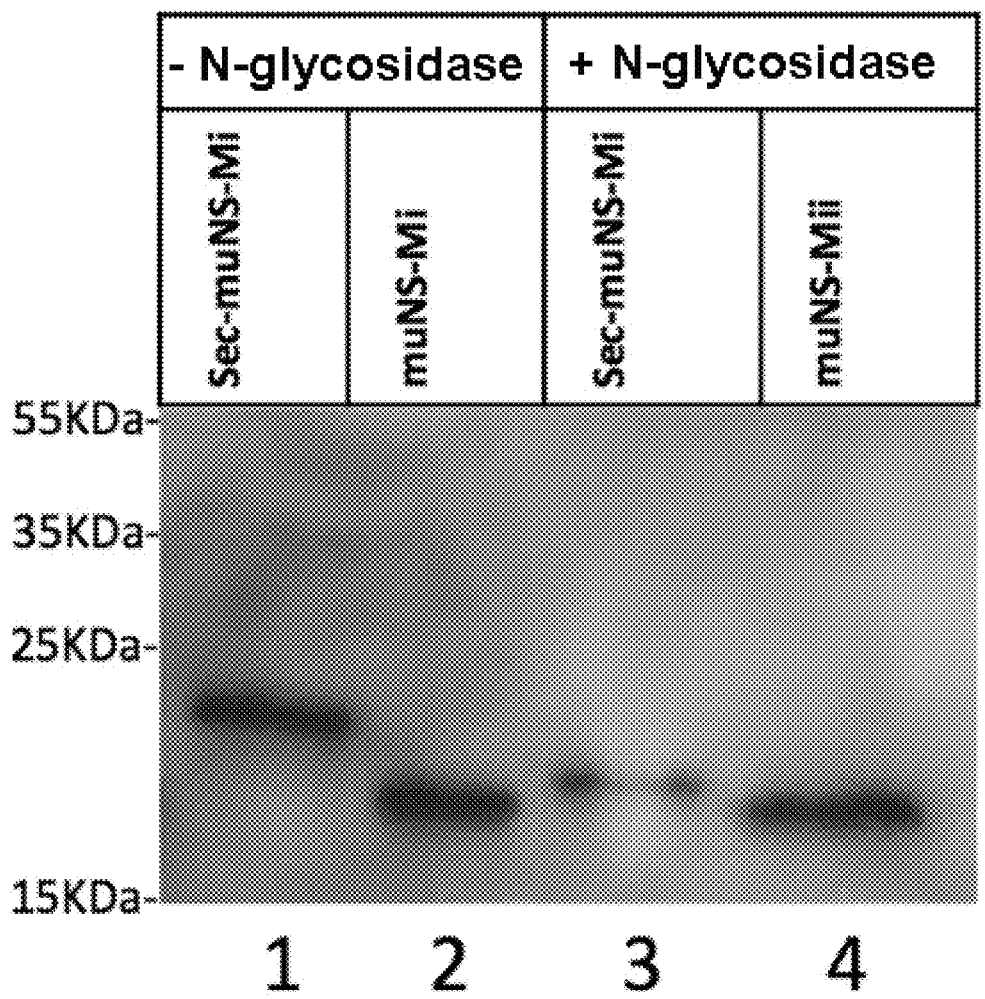
FIG. 2 shows the analysis of the glycosylation state of the muNS-Mi and Sec-muNS-Mi proteins.

To check if the protein containing the signal sequence was incorporated into the ER and if this translated to a type of post-translational modification, the presence of possible glycosylations and/or disulfide bonds, typical modifications in the ER, was analyzed. Digestion with N-glycosidase revealed that the protein with signal sequence has an apparent molecular weight slightly greater than that of the cytosolic protein (FIG. 2). However, the size of the protein with signal sequence becomes smaller after treating it with N-glycosidase, whereas the size of the cytosolic protein treated in the same way does not change at all (FIG. 2), which confirms the presence of glycosylations in Sec-muNS-Mi. These results unequivocally confirm that the protein with signal sequence enters the ER where it forms microspheres in an inefficient manner.

Example 2: Sec-MuNS-Mi Mutation for Eliminating N-Glycosylations

Those glycosylations may possibly affect microsphere formation efficiency in the ER because they are very bulky groups that may affect the interaction between muNS monomers for constructing said structures. The native cytosolic avian reovirus muNS protein is not glycosylated. In view of these results, the presence of N-glycosylation targets in the muNS-Mi amino acid sequence was analyzed. As a result, the NVS sequence was identified in positions 504-506 of the avian Orthoreovirus muNS protein sequence, i.e., within the IC domain which is crucial for microsphere formation.

To check if glycosylation in position 504 is responsible for the lower inclusion formation efficiency in the ER, a point mutation was carried out in the NVS sequence both of muNS-Mi and of Sec-MuNS-Mi. To that end, the Asn in position 504 was modified to a Ser. The presence of the mutation was confirmed by sequencing.

Figure 3:
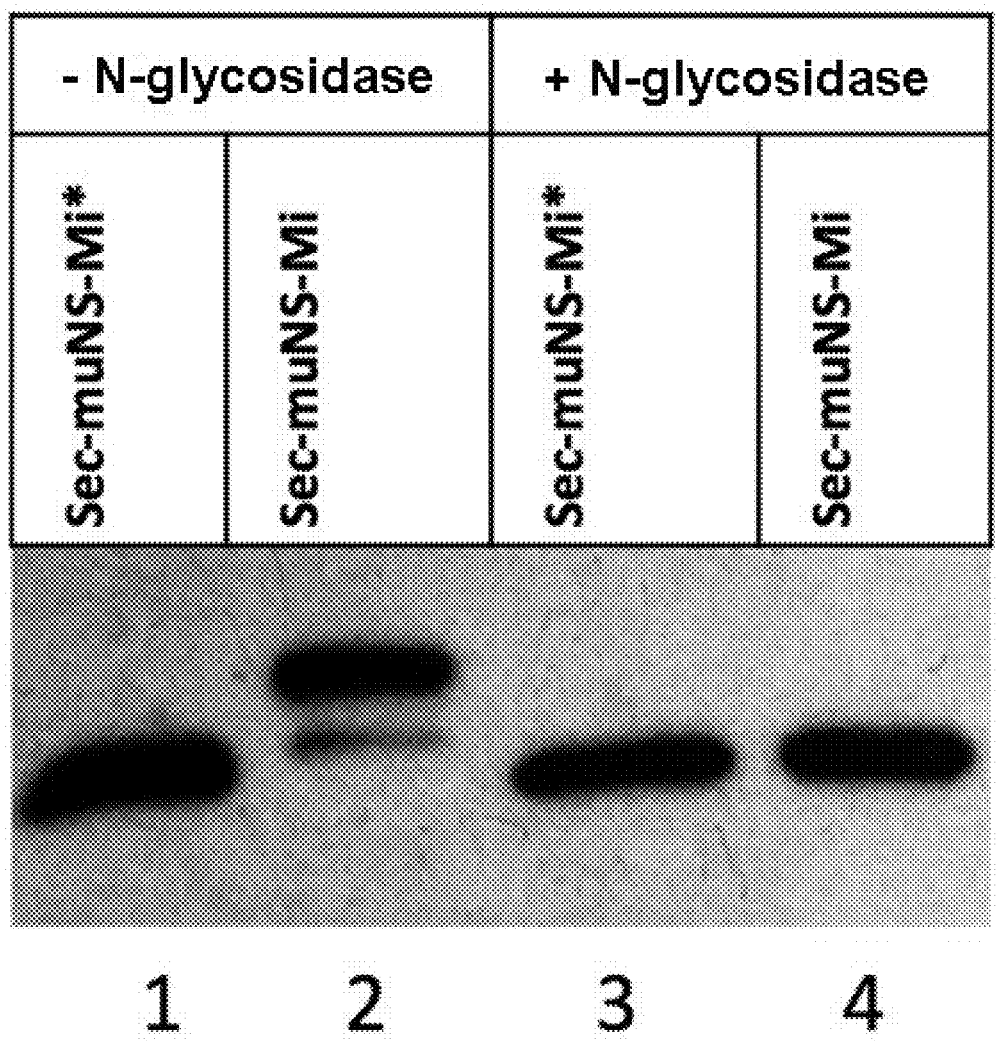
FIG. 3 shows the analysis of the glycosylation state of the Sec-muNS-Mi and Sec-muNS-Mi* proteins.

DF-1 cells were then transfected with the generated plasmids, allowing the protein to be expressed for 24 hours, after which the cells were fixed and the presence of muNS-Mi was detected by immunofluorescence using anti-muNS protein antibodies. The Western blot result revealed different electrophoretic patterns for the Sec-mNS-Mi protein and the mutated version (Sec-muNS-Mi*), Sec-muNS-Mi* having a smaller apparent molecular weight than Sec-muNS-Mi (FIG. 3). The molecular weight of Sec-muNS-Mi* corresponds with the molecular weight of Sec-muNS-Mi after being digested with N-glycosidase (FIG. 3). These results demonstrate that the Asn in position 504 was in fact N-glycosylated in the ER and that the Ser in position 504 of the mutated protein was not.

Example 3: Formation of muNS-Mi* Inclusions in the Cytosol

Figure 4:
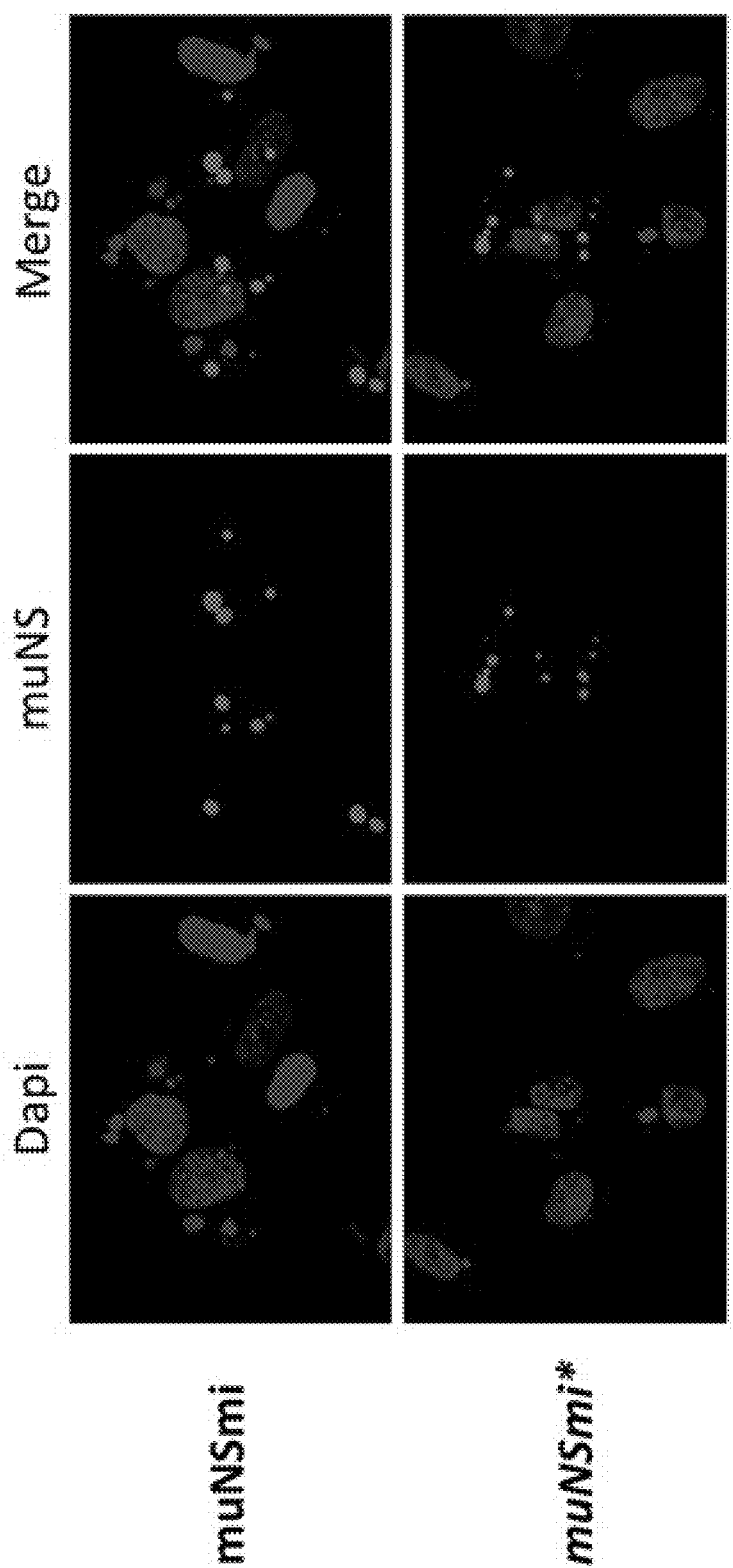
FIG. 4 shows the immunofluorescence analysis of the expression and inclusion-forming capacity of the muNS-Mi and muNS-Mi* proteins.

Since mutation N504S is within the IC domain which is essential for forming inclusions, if this change affects the formation of cytosolic inclusions was checked. To that end, DF-1 cells were transfected with the plasmids directing the expression of muNS-Mi and muNS-Mi* proteins for comparing the inclusion formation efficiency of both in the cytosol. The transfected cells were incubated for 24 hours, after which the cells were fixed and the presence of muNS-Mi was detected by immunofluorescence using anti-muNS protein antibodies. Surprisingly, muNS-Mi and muNS-Mi* generated similar cytosolic inclusions in an efficient manner (FIG. 4).

Example 4: Incorporation of GFP Protein into muNS-Mi* Inclusions in the Cytosol

To check if mutation N504S affected the recruitment of proteins with IC tag into the inclusions formed by muNS-Mi and muNS-Mi*, the corresponding N28S mutation in the IC region of the GFP-IC fusion protein was carried out to obtain GFP-IC*.

Figure 5:
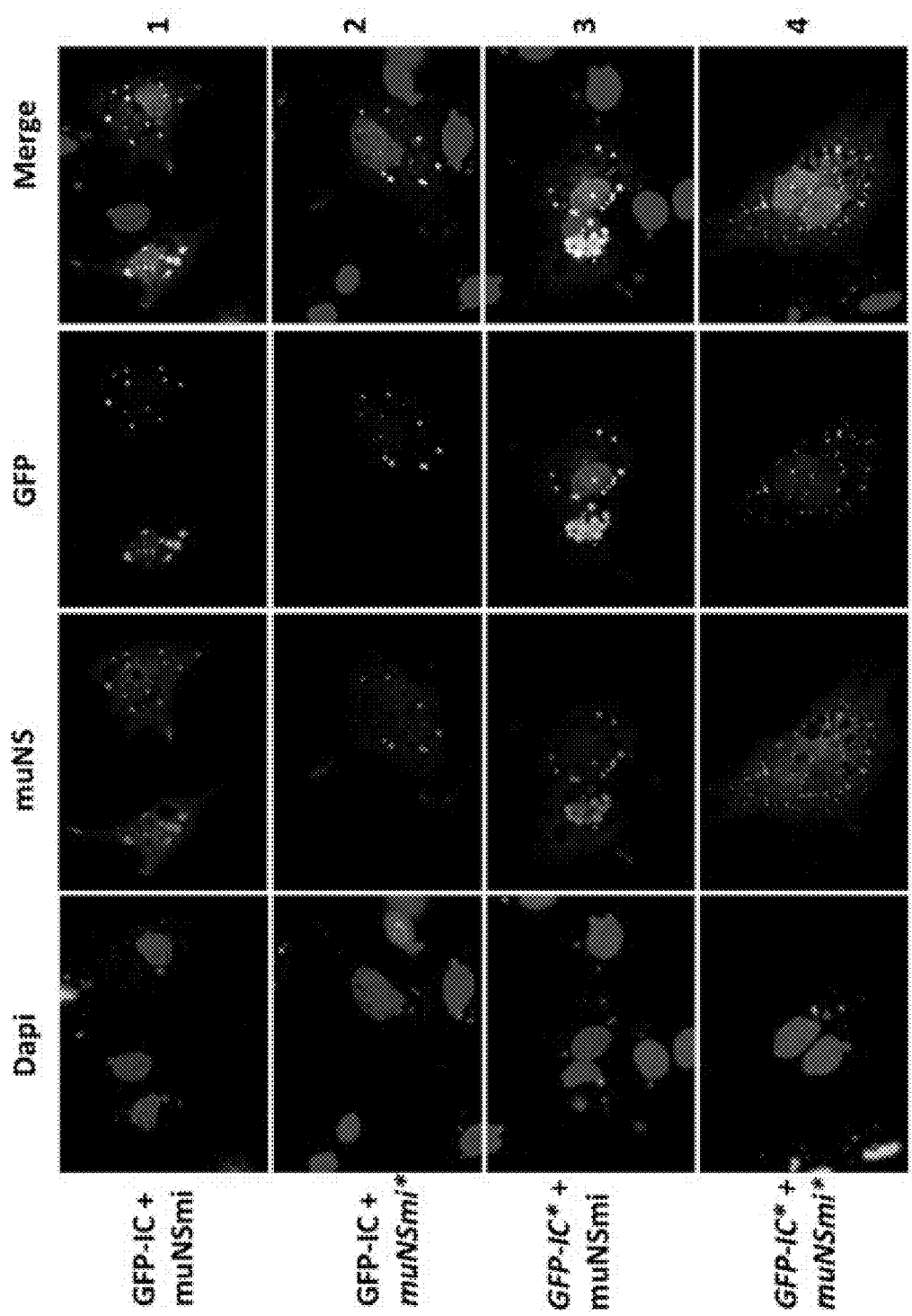
FIG. 5 shows the immunofluorescence analysis of the expression of the muNS-Mi and muNS-Mi* proteins and their capacity to recruit GFP-IC or GFP-IC*.

DF-1 cells were then co-transfected with different combinations of plasmids for targeting muNS-Mi and muNS-Mi* with the GFP-IC- and GFP-IC*-tagged GFP protein (FIG. 5). The transfected cells were incubated for 24 hours, after which the cells were fixed and the presence of muNS-Mi was detected by immunofluorescence using anti-muNS protein antibodies. The results shown in FIG. 5 clearly demonstrate that muNS-Mi* is capable of recruiting both GFP-IC (line 2) and GFP-IC* (line 4) with the same efficiency as it does with muNS-Mi (lines 1 and 3).

Example 5: Formation of muNS-Mi* Inclusions in the ER

To check if N504S mutation is capable of increasing the inclusion formation efficiency in the ER, DF-1 cells were transfected with Sec-muNS-Mi or Sec-muNS-Mi* for determining the capacity of both to form inclusions in the ER by immunofluorescence.

Figure 6:
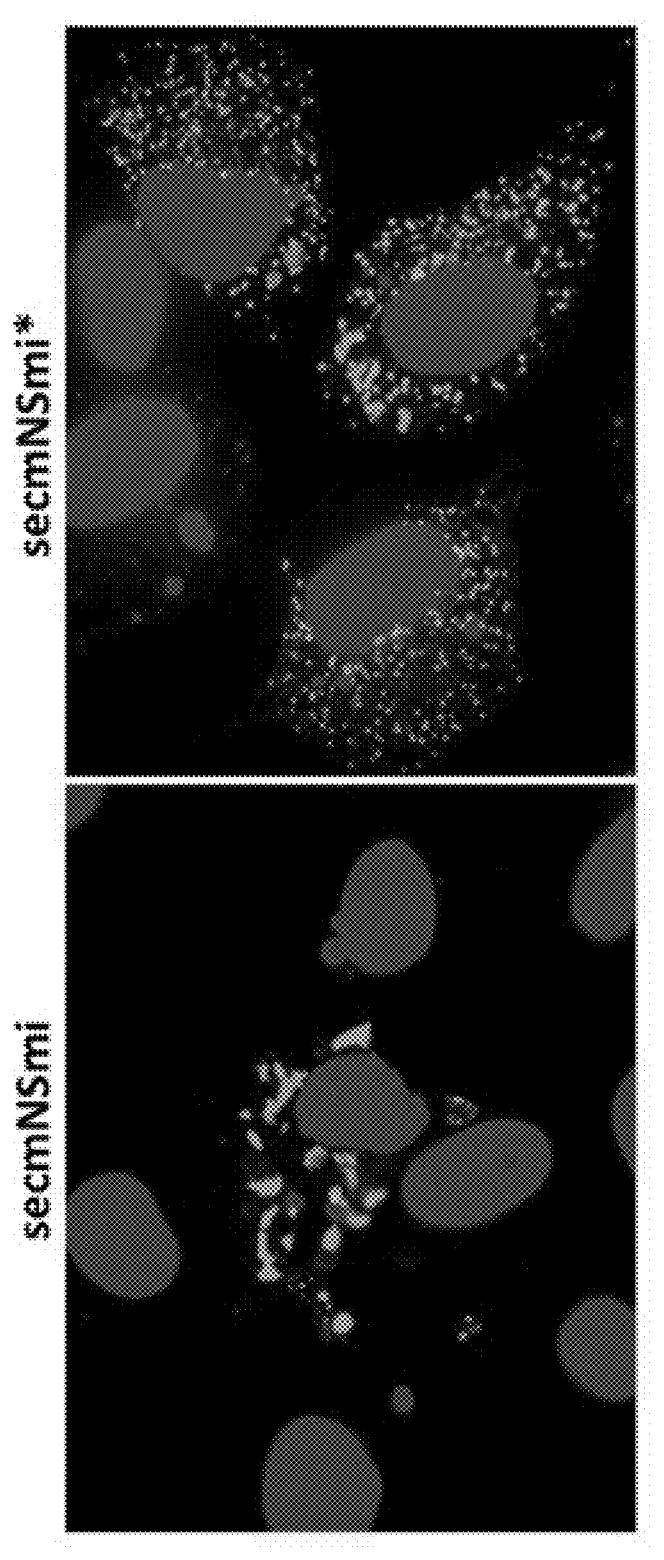

The analysis and comparison of the expression of both proteins demonstrated that they indeed form inclusions in the ER in a much more efficient manner as virtually all the cells contain inclusions (FIG. 6). Furthermore, the inclusions formed by Sec-muNS-Mi* have a morphology different from inclusions formed by the non-mutated Sec-muNS-Mi version as they are visibly smaller than these. This may indicate that the spheres seen in cells expressing the non-mutated protein may not be real ordered inclusions, but merely protein accumulates in vesicles of the secretory system (FIG. 1).

Example 6: Incorporation of Vesicular Stomatitis Virus (VSV) Glycoprotein G into muNS-Mi* Inclusions in the ER DF-1 cells were co-transfected with pcDNA-secmuNS-Mi* and pcDNA-VSVg-SV5-IC*. The co-transfected cells were incubated for 24 hours, after which the cells were fixed and the presence of muNS-Mi was detected by immunofluorescence using (rabbit) anti-muNS protein antibodies and (mouse) anti-SV5 antibodies. Alexa Fluor 594 goat anti-mouse (A-11005) and Alexa Fluor 488 goat anti-rabbit (A-11008) were used as secondary antibodies.

Figure 7:
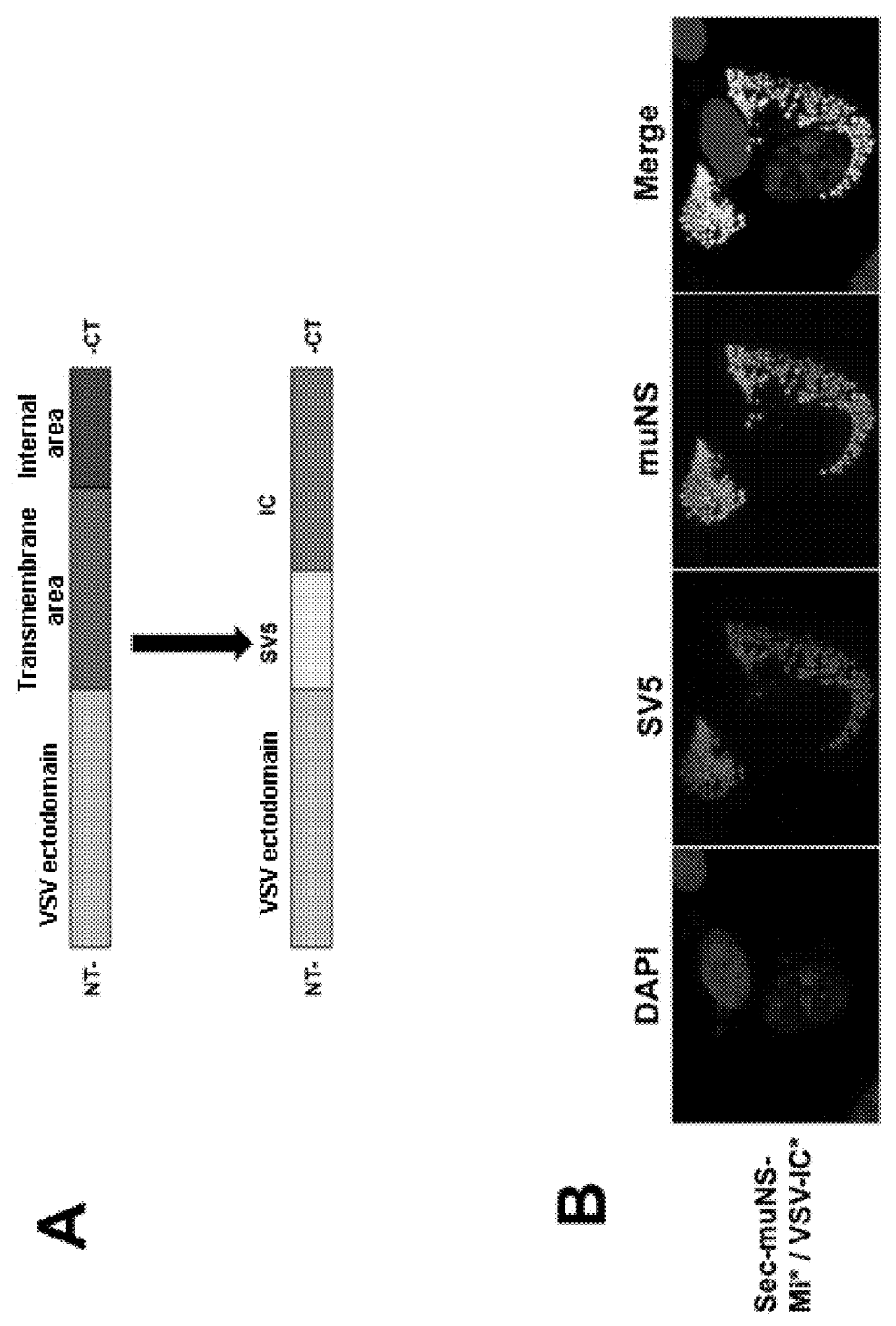

The results shown in FIGS. 7A and 7B reveal that the ectodomain of IC-tagged VSV glycoprotein G is efficiently incorporated into muNS-Mi* microspheres in the ER.

The invention claimed is:

1. A product selected from the group consisting of:

(a) a polynucleotide encoding a polypeptide comprising:

(i) a first component comprising a secretory pathway signal peptide, and (ii) a second component comprising the minimum region of an Orthoreovirus muNS protein set forth in the amino acid sequence of SEQ ID NO: 11 or SEQ ID NO: 12 or a functionally equivalent variant thereof having at least 90% sequence identity to the amino acid sequence of SEQ ID NO: 11 or SEQ ID NO: 12, wherein said second component has the capacity to form inclusions in the endoplasmic reticulum when expressed in a cell, and wherein said second component lacks N-glycosylation consensus sequences, wherein said first component is located in the N-terminal position with respect to said second component;

(b) a polypeptide encoded by the polynucleotide of (a);

(c) a polynucleotide encoding a fusion protein comprising:

(i) a first component comprising a secretory pathway signal peptide, (ii) a second component comprising a polypeptide of interest, and (iii) a third component comprising the minimum region of an Ortheovirus muNS protein set forth in the amino acid sequence of SEQ ID NO: 21-24 or a functionally equivalent variant thereof having at least 90% sequence identity to the amino acid sequence of SEQ ID NO: 21-24, wherein said third component has the capacity to incorporate itself into inclusions formed in the endoplasmic reticulum by a protein comprising the minimum region of an Orthoreovirus muNS having the capacity to form inclusions in the endoplasmic reticulum when expressed in a cell, and wherein said third component lacks N-glycosylation consensus sequences, wherein said first component is located in the N-terminal position with respect to said second and third components; and (d) a fusion protein encoded by the polynucleotide of (c).

2. The product of claim 1, wherein said first component of the polypeptide defined in (a) or said first component of the fusion protein defined in (c) comprises the amino acid sequence of SEQ ID NO: 1.

3. The product of claim 1, wherein said second component of the polypeptide defined in (a) comprises an amino acid sequence selected from the group consisting of the amino acid sequence of SEQ ID NO: 13, 14, 15, and 16.

4. The product of claim 1, wherein said polypeptide encoded by the polynucleotide defined in (a) or said fusion protein encoded by the polynucleotide defined in (c) further comprises a peptide for facilitating purification located in the C-terminal position with respect to said first component.

5. The product of claim 1, wherein said polypeptide encoded by the polynucleotide defined in (a) further comprises a polypeptide of interest located in the C-terminal position with respect to said first component.

6. The product of claim 1, wherein said third component of the fusion protein defined in (c) comprises the amino acid sequence of SEQ ID NO: 25.

7. The product of claim 1, wherein said third component of the fusion protein defined in (c) comprises the amino acid sequence of SEQ ID NO: 26.

8. A cell comprising the polynucleotide, the polypeptide, or the fusion protein of claim 1.

9. A kit comprising:

(i) component A selected from the group consisting of:

the polynucleotide of item (a) of claim 1; and a cell expressing the polynucleotide of item (a) of claim 1; and (ii) component B comprising the polynucleotide of item (c) of claim 1.

10. A purification method for purifying a polypeptide comprising the minimum region of an Orthoreovirus muNS protein having the capacity to form inclusions when expressed in a cell, wherein said method comprises:

(i) expressing in a cell the polynucleotide of claim 5/under conditions suitable for the translocation of said polypeptide to the secretory pathway and the formation of inclusions from said minimum region, and (ii) purifying the inclusions formed in step (i).

11. A method for purifying a fusion protein comprising a polypeptide of interest and the minimum region of an Orthoreovirus muNS protein having the capacity to incorporate itself into inclusions formed by a protein having the minimum region of an Orthoreovirus muNS having the capacity to form inclusions when expressed in a cell, wherein said method comprises:

(i) expressing in a cell the polynucleotide of item (a) of claim 1, under conditions for the translocation of the polypeptide to the secretory pathway and the formation of inclusion from said minimum region, (ii) expressing in said cell the polynucleotide of item (c) of claim 1, under conditions suitable for the translocation of the polypeptide to the secretory pathway and for the recruitment of the fusion protein into the inclusions produced in step (i), and (iii) purifying said inclusions formed in step (i) and said fusion proteins produced in step (ii), wherein steps (i) and (ii) can be carried out in any order.

12. The method of claim 11, further comprising separating said fusion protein from said inclusions.

13. A method for detecting the interaction between a first polypeptide and a second polypeptide, said method comprises:

(i) expressing in a cell the polynucleotide of claim 5, wherein said polypeptide of interest is the first polypeptide and keeping said cell under conditions suitable for forming inclusions;

(ii) expressing in said cell a polynucleotide encoding a fusion protein comprising a secretory pathway signal peptide and said second polypeptide and keeping said cell under conditions suitable for said second polypeptide to be expressed; and
(iii) determining if said second polypeptide is associated with said inclusions generated in step (i), wherein if said second polypeptide is detected it is indicative of the interaction between said first and second polypeptides;

wherein steps (i) and (ii) are carried out in any order.

* * * * *